US012448449B2

(12) United States Patent
Grewal et al.

(10) Patent No.: US 12,448,449 B2
(45) **Date of Patent: *Oct. 21, 2025**

(54) IMMUNE TARGETING MOLECULES AND USES THEREOF

(71) Applicant: JANSSEN BIOTECH, INC., Horsham, PA (US)

(72) Inventors: Iqbal S. Grewal, Newtown, PA (US); Michael Riis Hansen, Broomall, PA (US); Rajkumar Ganesan, Blue Bell, PA (US); Sanjaya Singh, Blue Bell, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/472,186

(22) Filed: Sep. 10, 2021

(65) Prior Publication Data

US 2022/0089736 A1 Mar. 24, 2022

Related U.S. Application Data

(60) Provisional application No. 63/237,974, filed on Aug. 27, 2021, provisional application No. 63/165,050, (Continued)

(51) Int. Cl.
*C07K 16/28* (2006.01)

(52) U.S. Cl.
CPC ...... *C07K 16/2818* (2013.01); *C07K 16/2809* (2013.01); *C07K 16/2878* (2013.01); (Continued)

(58) Field of Classification Search
CPC ............ C07K 16/2818; C07K 16/2809; C07K 16/2878; C07K 2317/24; C07K 2317/31; C07K 2317/92
See application file for complete search history.

(56) References Cited

U.S. PATENT DOCUMENTS 6,084,087 A 7/2000 Friedman
6,221,352 B1 4/2001 Howell et al.
(Continued)

FOREIGN PATENT DOCUMENTS

WO 2006028936 3/2006
WO 2006116269 A2 11/2006
(Continued)

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

(Continued)

*Primary Examiner* — Aurora M Fontainhas
*Assistant Examiner* — Selam Berhane

(57) ABSTRACT

Provided herein, in certain aspects, are antibodies that bind to CD28, as well as recombinant cells containing the vectors, and compositions comprising the antibodies. Also provided herein, in certain aspects, are multispecific antibodies that bind to CD28, as well as recombinant cells containing the vectors, and compositions comprising the antibodies. Methods of making and using the antibodies are also provided.

5 Claims, 23 Drawing Sheets

Specification includes a Sequence Listing.

Related U.S. Application Data filed on Mar. 23, 2021, provisional application No. 63/077,458, filed on Sep. 11, 2020.

(52) U.S. Cl.
CPC ...... *C07K 2317/24* (2013.01); *C07K 2317/31* (2013.01); *C07K 2317/92* (2013.01)

(56) References Cited

U.S. PATENT DOCUMENTS

| | | | | |
|---|---|---|---|---|
| 6,413,516 | B1 | 7/2002 | Chang et al. | |
| 6,521,427 | B1 | 2/2003 | Evans | |
| 6,670,127 | B2 | 12/2003 | Evans | |
| 6,737,056 | B1 | 5/2004 | Presta | |
| 9,168,314 | B2 * | 10/2015 | Satijn | A61K 45/06 |
| 2006/0286104 | A1 | 12/2006 | Hanke | |
| 2009/0182127 | A1 | 7/2009 | Kjaergaard | |
| 2010/0015133 | A1 | 1/2010 | Igawa | |
| 2010/0028637 | A1 | 2/2010 | Tavsanli | |
| 2011/0123532 | A1 | 5/2011 | Gurney | |
| 2012/0149876 | A1 | 6/2012 | Von Kreudenstein | |
| 2013/0195849 | A1 | 8/2013 | Spreter Von Kreudenstein | |
| 2013/0230540 | A1 | 9/2013 | Holmes | |
| 2014/0088295 | A1 | 3/2014 | Smith et al. | |
| 2016/0053020 | A1 | 2/2016 | Verploegen | |
| 2016/0347858 | A1 | 12/2016 | Sakamoto | |
| 2017/0015738 | A1 | 1/2017 | Pedersen | |
| 2017/0088620 | A1 | 3/2017 | Nioi | |
| 2017/0355756 | A1 * | 12/2017 | Julien | C07K 16/18 |
| 2022/0089731 | A1 | 3/2022 | Ganesan et al. | |
| 2022/0089737 | A1 * | 3/2022 | Ganesan | C07K 16/2818 |

FOREIGN PATENT DOCUMENTS

| | | | | |
|---|---|---|---|---|
| WO | WO-2008068048 | A2 * | 6/2008 | A61P 31/10 |
| WO | 2009139822 | A1 | 11/2009 | |
| WO | 2011014469 | A1 | 2/2011 | |
| WO | 2011131746 | A2 | 10/2011 | |
| WO | 2014159531 | A1 | 10/2014 | |
| WO | 2016014535 | A1 | 1/2016 | |
| WO | 2016073845 | | 5/2016 | |
| WO | 2017019957 | A2 | 2/2017 | |
| WO | 2018015340 | | 1/2018 | |
| WO | 2018187799 | A1 | 10/2018 | |
| WO | 2018223002 | | 12/2018 | |
| WO | 2019091384 | | 5/2019 | |
| WO | WO 2019/246286 | A1 | 12/2019 | |
| WO | 2020010250 | | 1/2020 | |
| WO | WO 2020/010250 | A2 | 1/2020 | |
| WO | 2020142672 | | 7/2020 | |
| WO | 2020183245 | A2 | 9/2020 | |
| WO | 2020257760 | A1 | 12/2020 | |
| WO | 2021064671 | A1 | 4/2021 | |
| WO | 2021173896 | A1 | 9/2021 | |

OTHER PUBLICATIONS

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Kussie, Paul H., "A Single Engineered Amino Acid Substitution Changes Antibody Fine Specificity", 1994, Journal of Immunology 152(1): pp. 146-152. (Year: 1994).*

Al-Lazikani et al., "Standard conformations for the canonical structures of immunoglobulins", J. Mol. Biol. 273:927-948 (1997).

Atwell et al. "Stable Heterodimers from Remodeling the Domain Interface of a Homodimer using a Phage Display Library," Journal of Molecular Biology, vol. 270, 1997, 26-35.

Brown et al., "A Study of the Interactions Between an IgG-Binding Domain Based on the B Domain of staphylococcal Protein A and Rabbit IgG", Mol. Biotech. 10:9-16, 1998.

Ferrara et al., "Modulation of Therapeutic Antibody Effector Functions by Glycosylation Engineering: Influence of Golgi Enzyme Localization Domain and Co-Expression of Heterolgous B1, 4-N-acetylglucosaminyltransferase III and Golgi m-mannodsidase II", Biotechnol Bioeng 93:851-861, 2006.

Ferrara et al., "The carbohydrate at FCYRIIIa Asn-162; An element required for high affinity binding to non-fucosylated IgG glycoforms", J Biol Chem 281:5032-5036, 2006.

Fransson J, et al. "Human framework adaptation of a mouse anti-human IL-13 antibody", J. Mol. Biol. 2010; 398:214-231.

Kabat et al., "Unusual distributions of amino acids in complementarity-determining (hypervariable) segments of heavy and light chains of immunoglobulins and their possible roles in specificity of antibody-combining sites", J. Biol. Chem. 252:6609-6616 (1977).

Kabat, Elivin A. "The Structural Basis of Antibody Complementarity," Adv. Prot. Chem. 32:1-75 (1978).

Kawasaki et al., "Presence of four major haplotypes in human BCMA gene: lack of association with systemic lupus erythematosus and rheumatoid arthritis", Genes Immun. 2:276-9, 2001.

Konno et al., "Fucose content of monoclonal antibodies can be controlled by culture medium osmolality for high antibody-dependent cellular cytotoxicity", Cytotechnology 64:249-65, 2012.

Lefranc et al., "IMGT unique numbering for immunoglobulin and T cell receptor variable domains and Ig superfamily V-like domains", Dev. Comp. Immunol. 27(1):55-77 (2003).

Morea et al., "Antibody Modeling: Implications for Engineering and Design," Methods, vol. 20, 2000; pp. 267-279.

Mori et al., "Engineering Chinese hamster ovary cells to maximize effector function of produced antibodies using FUT8 SiRNA", Biotechnol Bioeng 88:901-908, 2004.

Olivier et al., "EB66 cell line, a duck embryonic stem cell-derived substrate for the industrial production of therapeutic monoclonal antibodies with enhanced ADCC activity", MAbs; 2(4), 2010.

Osborn, et al., "High-Affinity IgG antibodies develop naturally in Ig-knockout rats carrying germline human IgH/Igk/Igy loci bearing the rat CH region", J Immunol, 2013, 190(4): 1481-90.

Shields et al., "Lack of fucose on human lgG1 N-Linked oligosaccharide improves binding to human FCYRIII and antibody-dependent cellular toxicity", J Biol Chem 277:26733-26740, 2002.

Shinkawa et al., "The absence of fucose but not the presence of galactose or bisection N-Acetylglucosamine of human IgG1 complex-type oligosaccharides shows the critical role of enhancing antibody-dependent cellular cytotoxicity", J Biol Chem 278:3466-3473, 2003.

Zhou et al., "Development of a simple and rapid method for producing non-fucosylated oligomannose containing antibodies with increased effector function", Biotechnol Bioeng 99:652-65, 2008.

* cited by examiner

SEQUENCE LISTING

```
<160> NUMBER OF SEQ ID NOS: 136

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Ala Met Ser
1               5
```

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2

```
Ala Ile Ser Gly Ser Gly Gly Arg Thr Tyr Tyr Ala Asp Ser Val Lys
1               5                   10                  15

Gly
```

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

```
Gly Ala Gly Tyr Trp Tyr Phe Asp Leu
1               5
```

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

```
Arg Ala Ser Gln Ser Val Ser Ser Tyr Leu Ala
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

```
Asp Ala Ser Asn Arg Ala Thr
1               5
```

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

```
Gln Gln Arg Ser Asn Trp Pro Leu Thr
1               5
```

<210> SEQ ID NO 7
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 7

Glu Phe Thr Phe Thr Ser Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gly Ser Gly Gly Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ala Gly Tyr Trp Tyr Phe Asp
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Gln Ser Val Ser Ser Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ala Ser
1

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Asn Trp Pro Leu
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Glu Phe Thr Phe Thr Ser Tyr Ala Met Ser
1 5 10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Ala Ile Ser Gly Ser Gly Gly Arg Thr Tyr
1 5 10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Gly Ala Gly Tyr Trp Tyr Phe Asp Leu
1 5

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Arg Ala Ser Gln Ser Val Ser Ser Tyr Leu Ala
1 5 10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Asp Ala Ser Asn Arg Ala Thr
1 5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Gln Gln Arg Ser Asn Trp Pro Leu Thr
1 5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Thr Ser Tyr Ala Met Ser
1 5

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Trp Val Ser Ala Ile Ser Gly Ser Gly Gly Arg Thr Tyr
1 5 10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Ala Lys Gly Ala Gly Tyr Trp Tyr Phe Asp
1 5 10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Ser Ser Tyr Leu Ala Trp Tyr
1 5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Leu Leu Ile Tyr Asp Ala Ser Asn Arg Ala
1 5 10

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Gln Gln Arg Ser Asn Trp Pro Leu
1 5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Glu Phe Thr Phe Thr Ser Tyr Ala
1 5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Ile Ser Gly Ser Gly Gly Arg Thr
1 5

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Ala Lys Gly Ala Gly Tyr Trp Tyr Phe Asp Leu
1 5 10

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Gln Ser Val Ser Ser Tyr
1 5

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Asp Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Gln Gln Arg Ser Asn Trp Pro Leu Thr
1 5

<210> SEQ ID NO 31
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Glu Val Gln Leu Leu Glu Ser Gly Gly Gly Leu Gly Gln Pro Gly Gly
1 5 10 15

Ser Leu Arg Leu Ser Cys Ala Ala Ser Glu Phe Thr Phe Thr Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Ala Gly Tyr Trp Tyr Phe Asp Leu Trp Gly Arg Gly Thr
100 105 110

Leu Val Thr Val Ser Ser
115

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Glu Ile Val Leu Thr Gln Ser Pro Ala Thr Leu Ser Leu Ser Pro Gly
1 5 10 15

Glu Arg Ala Ile Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Leu
85 90 95

Thr Phe Gly Gly Gly Thr Lys Val Glu Ile Lys 100 105

<210> SEQ ID NO 33
<211> LENGTH: 449
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

Glu Val Gln Leu Leu Glu Ser Gly Gly Gly Leu Gly Gln Pro Gly Gly
1 5 10 15

Ser Leu Arg Leu Ser Cys Ala Ala Ser Glu Phe Thr Phe Thr Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Gly Ala Gly Tyr Trp Tyr Phe Asp Leu Trp Gly Arg Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Ala Ala Gly Ala Ser
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser Ala Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ser Ser Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Leu Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 34
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Val Leu Thr Gln Ser Pro Ala Thr Leu Ser Leu Ser Pro Gly
1               5                   10                  15

Glu Arg Ala Ile Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 5
<212> TYPE: PRT
<213> ORGANISM: Artificial Sequence
<220> FEATURE:

<223> OTHER INFORMATION: Description of Artificial Sequence: Synthetic peptide

<400> SEQUENCE: 35

Ser Tyr Trp Met His
1 5

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Asn Ile Tyr Pro Gly Ser Gly Arg Thr Asn Tyr Asp Glu Lys Phe Lys
1 5 10 15

Ser

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Glu His Tyr Gly Ser Asn Ser His Pro Met Asp Tyr
1 5 10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gly Ala Ser Glu Asn Ile Tyr Gly Ser Leu Asn
1 5 10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gly Ala Thr Asn Leu Ala Asp
1 5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Gln Asn Leu Leu Ser Thr Pro Tyr Thr
1 5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Gly Tyr Thr Phe Thr Ser Tyr
1 5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Tyr Pro Gly Ser Gly Arg
1 5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Glu His Tyr Gly Ser Asn Ser His Pro Met Asp
1 5 10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Ser Glu Asn Ile Tyr Gly Ser
1 5

<210> SEQ ID NO 45
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Gly Ala Thr
1

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Leu Leu Ser Thr Pro Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Tyr Thr Phe Thr Ser Tyr Trp Met His
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asn Ile Tyr Pro Gly Ser Gly Arg Thr Asn
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu His Tyr Gly Ser Asn Ser His Pro Met Asp Tyr
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ala Ser Glu Asn Ile Tyr Gly Ser Leu Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Ala Thr Asn Leu Ala Asp
1               5

<210> SEQ ID NO 52
<211> LENGTH: 9

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Gln Asn Leu Leu Ser Thr Pro Tyr Thr
1 5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Thr Ser Tyr Trp Met His
1 5

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Trp Ile Gly Asn Ile Tyr Pro Gly Ser Gly Arg Thr Asn
1 5 10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Thr Arg Glu His Tyr Gly Ser Asn Ser His Pro Met Asp
1 5 10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Tyr Gly Ser Leu Asn Trp Tyr
1 5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Leu Leu Ile Tyr Gly Ala Thr Asn Leu Ala 1 5 10

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Gln Asn Leu Leu Ser Thr Pro Tyr
1 5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Gly Tyr Thr Phe Thr Ser Tyr Trp
1 5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ile Tyr Pro Gly Ser Gly Arg Thr
1 5

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Thr Arg Glu His Tyr Gly Ser Asn Ser His Pro Met Asp Tyr
1 5 10

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Glu Asn Ile Tyr Gly Ser
1 5

<210> SEQ ID NO 63
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Gly Ala Thr
1

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

```
Gln Asn Leu Leu Ser Thr Pro Tyr Thr
1               5
```

<210> SEQ ID NO 65
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

```
Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg His Gly Gln Gly Leu Glu Trp Ile
        35                  40                  45

Gly Asn Ile Tyr Pro Gly Ser Gly Arg Thr Asn Tyr Asp Glu Lys Phe
    50                  55                  60

Lys Ser Lys Gly Thr Leu Thr Val Asp Thr Ser Ser Arg Thr Ala Tyr
65                  70                  75                  80

Met His Leu Ser Ser Leu Thr Ser Glu Asp Ser Ala Val Tyr Tyr Cys
                85                  90                  95

Thr Arg Glu His Tyr Gly Ser Asn Ser His Pro Met Asp Tyr Trp Gly
            100                 105                 110

Gln Gly Thr Ser Val Thr Val Ser Ser
        115                 120
```

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 66

```
Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ser
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60
```

Ser Gly Ser Gly Arg Gln Phe Ser Leu Lys Ile Ser Ser Leu His Pro
65 70 75 80

Asp Asp Val Ala Thr Tyr Tyr Cys Gln Asn Leu Leu Ser Thr Pro Tyr
85 90 95

Thr Phe Gly Gly Gly Thr Lys Leu Glu Leu Lys
100 105

<210> SEQ ID NO 67
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Gln Val Gln Leu Gln Gln Pro Gly Ser Glu Leu Val Arg Pro Gly Ala
1 5 10 15

Ser Val Lys Leu Ser Cys Lys Ala Ser Gly Tyr Thr Phe Thr Ser Tyr
20 25 30

Trp Met His Trp Val Lys Gln Arg His Gly Gln Gly Leu Glu Trp Ile
35 40 45

Gly Asn Ile Tyr Pro Gly Ser Gly Arg Thr Asn Tyr Asp Glu Lys Phe
50 55 60

Lys Ser Lys Gly Thr Leu Thr Val Asp Thr Ser Ser Arg Thr Ala Tyr
65 70 75 80

Met His Leu Ser Ser Leu Thr Ser Glu Asp Ser Ala Val Tyr Tyr Cys
85 90 95

Thr Arg Glu His Tyr Gly Ser Asn Ser His Pro Met Asp Tyr Trp Gly
100 105 110

Gln Gly Thr Ser Val Thr Val Ser Ser Ala Ser Thr Lys Gly Pro Ser
115 120 125

Val Phe Pro Leu Ala Pro Cys Ser Arg Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

Lys Pro Ser Asn Thr Lys Val Asp Lys Thr Val Glu Arg Lys Cys Cys
210 215 220

Val Glu Cys Pro Pro Cys Pro Ala Pro Pro Val Ala Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys
305 310 315 320

```
Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Leu Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 68
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ser
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Phe Ser Leu Lys Ile Ser Ser Leu His Pro
65                  70                  75                  80

Asp Asp Val Ala Thr Tyr Tyr Cys Gln Asn Leu Leu Ser Thr Pro Tyr
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Tyr Tyr Trp Ser
1               5

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Ile Asn His Ser Gly Asn Thr Asn Phe Asn Pro Ser Leu Lys Ser
1               5                   10                  15

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Glu Ala Trp Phe Asp Pro
1               5

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ala Ser Gln Ser Val Arg Ser Asn Leu Asp
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Ala Ser Thr Arg Ala Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Tyr Asn Asn Trp Pro Leu Thr
1 5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Gly Gly Ser Phe Ser Gly Tyr
1 5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Asn His Ser Gly Asn
1 5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Gly Glu Ala Trp Phe Asp
1 5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Ser Gln Ser Val Arg Ser Asn
1 5

<210> SEQ ID NO 79
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Gly Ala Ser
1

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Tyr Asn Asn Trp Pro Leu
1 5

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Gly Gly Ser Phe Ser Gly Tyr Tyr Trp Ser
1 5 10

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Asp Ile Asn His Ser Gly Asn Thr Asn
1 5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Gly Glu Ala Trp Phe Asp Pro
1 5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Arg Ala Ser Gln Ser Val Arg Ser Asn Leu Asp
1 5 10

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Gly Ala Ser Thr Arg Ala Thr
1 5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Gln Gln Tyr Asn Asn Trp Pro Leu Thr
1 5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Ser Gly Tyr Tyr Trp Ser
1 5

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Trp Ile Gly Asp Ile Asn His Ser Gly Asn Thr Asn
1 5 10

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Ala Lys Gly Glu Ala Trp Phe Asp
1 5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Arg Ser Asn Leu Asp Trp Tyr
1 5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Leu Leu Ile Tyr Gly Ala Ser Thr Arg Ala
1 5 10

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Gln Gln Tyr Asn Asn Trp Pro Leu
1 5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Gly Gly Ser Phe Ser Gly Tyr Tyr
1 5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Ile Asn His Ser Gly Asn Thr
1 5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Ala Lys Gly Glu Ala Trp Phe Asp Pro
1 5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Gln Ser Val Arg Ser Asn
1 5

<210> SEQ ID NO 97
<211> LENGTH: 3
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 97

Gly Ala Ser
1

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Gln Gln Tyr Asn Asn Trp Pro Leu Thr
1 5

<210> SEQ ID NO 99
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 99

Gln Val Gln Leu Gln Gln Trp Gly Ala Gly Leu Leu Lys Pro Ser Glu
1 5 10 15

Thr Leu Ser Leu Ile Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Asp Ile Asn His Ser Gly Asn Thr Asn Phe Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Lys Gly Glu Ala Trp Phe Asp Pro Trp Gly Gln Gly Ile Met Val Thr
100 105 110

Val Ser Ser
115

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 100

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Arg Ser Asn
20 25 30

Leu Asp Trp Tyr Gln Gln Lys Pro Gly Gln Ala Pro Arg Leu Leu Ile
35 40 45

```
Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105


<210> SEQ ID NO 101
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Gln Gln Trp Gly Ala Gly Leu Leu Lys Pro Ser Glu
1               5                   10                  15

Thr Leu Ser Leu Ile Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Asp Ile Asn His Ser Gly Asn Thr Asn Phe Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Gly Glu Ala Trp Phe Asp Pro Trp Gly Gln Gly Ile Met Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Ala Ala Ala Ser Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Ala Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300
```

Gln Asp Trp Leu Asn Gly Lys Glu Tyr Lys Cys Lys Val Ser Asn Lys
305 310 315 320

Gly Leu Pro Ser Ser Ile Glu Lys Thr Ile Ser Lys Thr Lys Gly Gln
325 330 335

Pro Arg Glu Pro Gln Val Tyr Thr Leu Pro Pro Ser Arg Glu Glu Met
340 345 350

Thr Lys Asn Gln Val Ser Leu Thr Cys Leu Val Lys Gly Phe Tyr Pro
355 360 365

Ser Asp Ile Ala Val Glu Trp Glu Ser Asn Gly Gln Pro Glu Asn Asn
370 375 380

Tyr Lys Thr Thr Pro Pro Met Leu Asp Ser Asp Gly Ser Phe Leu Leu
385 390 395 400

Tyr Ser Lys Leu Thr Val Asp Lys Ser Arg Trp Gln Gln Gly Asn Val
405 410 415

Phe Ser Cys Ser Val Met His Glu Ala Leu His Asn His Tyr Thr Gln
420 425 430

Lys Ser Leu Ser Leu Ser Pro Gly Lys
435 440

<210> SEQ ID NO 102
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Arg Ser Asn
20 25 30

Leu Asp Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys

210

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Gly Tyr Tyr Trp Asn
1 5

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Glu Ile Asn His Ser Gly Thr Thr Asn Tyr Asn Pro Ser Leu Lys Ser
1 5 10 15

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Gly Glu Ala Val Ala Leu Tyr
1 5

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Arg Ala Ser Gln Ser Val Asn Ser Asn Leu Ala
1 5 10

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

Gly Ala Ser Ala Arg Ala Thr
1 5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Gln Gln Tyr Tyr Asn Trp Pro Leu Thr
1 5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Gly Gly Ser Phe Ser Gly Tyr
1 5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Asn His Ser Gly Thr
1 5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Gly Glu Ala Val Ala Leu
1 5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Ser Gln Ser Val Asn Ser Asn
1 5

<210> SEQ ID NO 113
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Gly Ala Ser
1

<210> SEQ ID NO 114

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Tyr Tyr Asn Trp Pro Leu
1               5


<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Gly Ser Phe Ser Gly Tyr Tyr Trp Asn
1               5                   10


<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Glu Ile Asn His Ser Gly Thr Thr Asn
1               5


<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Glu Ala Val Ala Leu Tyr
1               5


<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Ala Ser Gln Ser Val Asn Ser Asn Leu Ala
1               5                   10


<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119
```

Gly Ala Ser Ala Arg Ala Thr
1 5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Gln Gln Tyr Tyr Asn Trp Pro Leu Thr
1 5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Ser Gly Tyr Tyr Trp Asn
1 5

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Trp Ile Gly Glu Ile Asn His Ser Gly Thr Thr Asn
1 5 10

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Ala Arg Gly Glu Ala Val Ala Leu
1 5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

Asn Ser Asn Leu Ala Trp Tyr
1 5

<210> SEQ ID NO 125
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 125

Leu Leu Ile Tyr Gly Ala Ser Ala Arg Ala
1               5                   10

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Gln Tyr Tyr Asn Trp Pro Leu
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Gly Ser Phe Ser Gly Tyr Tyr
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Asn His Ser Gly Thr Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Arg Gly Glu Ala Val Ala Leu Tyr
1               5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Ser Val Asn Ser Asn
1               5

<210> SEQ ID NO 131
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Gly Ala Ser
1

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Gln Gln Tyr Tyr Asn Trp Pro Leu Thr
1 5

<210> SEQ ID NO 133
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Asn Trp Ile Arg Gln Pro Pro Gly Lys Gly Leu Gln Trp Ile
35 40 45

Gly Glu Ile Asn His Ser Gly Thr Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Leu Thr Ala Ala Asp Thr Ala Val Tyr Tyr Cys Ala
85 90 95

Arg Gly Glu Ala Val Ala Leu Tyr Trp Gly Gln Gly Thr Leu Val Thr
100 105 110

Val Ser Ser
115

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Asn Ser Asn
20 25 30

```
Leu Ala Trp Tyr Gln Gln Lys Pro Gly Gln Ala Pro Arg Leu Leu Ile
        35                  40                  45

Tyr Gly Ala Ser Ala Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asn Trp Pro Leu
                85                  90                  95

Thr Phe Gly Gly Gly Thr Lys Val Glu Ile Lys
            100                 105


<210> SEQ ID NO 135
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Gln Trp Ile
        35                  40                  45

Gly Glu Ile Asn His Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Leu Thr Ala Ala Asp Thr Ala Val Tyr Tyr Cys Ala
                85                  90                  95

Arg Gly Glu Ala Val Ala Leu Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Ala Ala Ala Ser Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Ala Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285
```

```
Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Leu Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 136
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ala Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

-continued

```
Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
210
```

IMMUNE TARGETING MOLECULES AND USES THEREOF

CROSS-REFERENCE TO RELATED APPLICATIONS

This application claims the benefit of U.S. Ser. No. 63/077,458 filed Sep. 11, 2020; U.S. Ser. No. 63/165,050 filed Mar. 23, 2021; and U.S. Ser. No. 63/237,974 filed Aug. 27, 2021, the disclosure of each of which is incorporated by reference herein in its entirety.

FIELD

Provided herein, in certain aspects, are antibodies that bind to CD28, as well as recombinant cells containing the vectors, and compositions comprising the antibodies. Also provided herein, in certain aspects, are multispecific antibodies that bind to CD28, as well as recombinant cells containing the vectors, and compositions comprising the antibodies. Methods of making and using the antibodies are also provided.

REFERENCE TO SEQUENCE LISTING SUBMITTED ELECTRONICALLY

This application contains a sequence listing, which is submitted electronically via EFS-Web as an ASCII formatted sequence listing with a file "14620-553-999_SL.txt" and a creation date of Sep. 3, 2021 and having a size of 59,334 bytes. The sequence listing submitted via EFS-Web is part of the specification and is herein incorporated by reference in its entirety.

SUMMARY

In one aspect, provides is an antibody that binds CD28 comprising: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:31; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:32. In one aspect, provides is an antibody that binds CD28 comprising: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:65; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:66. In one aspect, provides is an antibody that binds CD28 comprising: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:99; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:100. In one aspect, provides is an antibody that binds CD28 comprising: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:133; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:134. In some embodiments, the VH CDR1, VH CDR2, VH CDR3, VL CDR1, VL CDR2, and VL CDR3 amino acid sequences are according to the Kabat numbering system. In some embodiments, the VH CDR1, VH CDR2, VH CDR3, VL CDR1, VL CDR2, and VL CDR3 amino acid sequences are according to the Chothia numbering system. In some embodiments, the VH CDR1, VH CDR2, VH CDR3, VL CDR1, VL CDR2, and VL CDR3 amino acid sequences are according to the AbM numbering system. In some embodiments, the VH CDR1, VH CDR2, VH CDR3, VL CDR1, VL CDR2, and VL CDR3 amino acid sequences are according to the Contact numbering system. In some embodiments, the VH CDR1, VH CDR2, VH CDR3, VL CDR1, VL CDR2, and VL CDR3 amino acid sequences are according to the IMGT numbering system.

In some embodiments, the antibody that binds CD28 provided herein comprises (i) a VH comprising a VH CDR1 having an amino acid sequence selected from SEQ ID NO: 1, SEQ ID NO: 7, SEQ ID NO: 13, SEQ ID NO: 19, and SEQ ID NO: 25; a VH CDR2 having an amino acid sequence selected from SEQ ID NO: 2, SEQ ID NO: 8, SEQ ID NO: 14, SEQ ID NO: 20, and SEQ ID NO: 26; a VH CDR3 having an amino acid sequence selected from SEQ ID NO: 3, SEQ ID NO: 9, SEQ ID NO: 15, SEQ ID NO: 21, and SEQ ID NO: 27; (ii) a VL comprising a VL CDR1 having an amino acid sequence selected from SEQ ID NO: 4, SEQ ID NO: 10, SEQ ID NO: 16, SEQ ID NO: 22, and SEQ ID NO: 28; a VL CDR2 having an amino acid sequence selected from SEQ ID NO: 5, SEQ ID NO: 11, SEQ ID NO: 17, SEQ ID NO: 23, and SEQ ID NO: 29; a VL CDR3 having an amino acid sequence selected from SEQ ID NO: 6, SEQ ID NO: 12, SEQ ID NO: 18, SEQ ID NO: 24, and SEQ ID NO: 30.

In some embodiments, the antibody that binds CD28 provided herein comprises (i) a VH comprising a VH CDR1 having an amino acid sequence selected from SEQ ID NO: 35, SEQ ID NO: 41, SEQ ID NO: 47, SEQ ID NO: 53, and SEQ ID NO: 59; a VH CDR2 having an amino acid sequence selected from SEQ ID NO: 36, SEQ ID NO: 42, SEQ ID NO: 48, SEQ ID NO: 54, and SEQ ID NO: 60; a VH CDR3 having an amino acid sequence selected from SEQ ID NO: 37, SEQ ID NO: 43, SEQ ID NO: 49, SEQ ID NO: 55, and SEQ ID NO: 61; and (ii) a VL comprising a VL CDR1 having an amino acid sequence selected from SEQ ID NO: 38, SEQ ID NO: 44, SEQ ID NO: 50, SEQ ID NO: 56, and SEQ ID NO: 62; a VL CDR2 having an amino acid sequence selected from SEQ ID NO: 39, SEQ ID NO: 45, SEQ ID NO: 51, SEQ ID NO: 57, and SEQ ID NO: 63; a VL CDR3 having an amino acid sequence selected from SEQ ID NO: 40, SEQ ID NO: 46, SEQ ID NO: 52, SEQ ID NO: 58, and SEQ ID NO: 64.

In some embodiments, the antibody that binds CD28 provided herein comprises (i) a VH comprising a VH CDR1 having an amino acid sequence selected from SEQ ID NO: 69, SEQ ID NO: 75, SEQ ID NO: 81, SEQ ID NO: 87, and SEQ ID NO: 93; a VH CDR2 having an amino acid sequence selected from SEQ ID NO: 70, SEQ ID NO: 76, SEQ ID NO: 82, SEQ ID NO: 88, and SEQ ID NO: 94; a VH CDR3 having an amino acid sequence selected from SEQ ID NO: 71, SEQ ID NO: 77, SEQ ID NO: 83, SEQ ID NO: 89, and SEQ ID NO: 95; and (ii) a VL comprising a VL CDR1 having an amino acid sequence selected from SEQ ID NO: 72, SEQ ID NO: 78, SEQ ID NO: 84, SEQ ID NO: 90, and SEQ ID NO: 96; a VL CDR2 having an amino acid sequence selected from SEQ ID NO: 73, SEQ ID NO: 79, SEQ ID NO: 85, SEQ ID NO: 91, and SEQ ID NO: 97; a VL CDR3 having an amino acid sequence selected from SEQ ID NO: 74, SEQ ID NO: 80, SEQ ID NO: 86, SEQ ID NO: 92, and SEQ ID NO: 98.

In some embodiments, the antibody that binds CD28 provided herein comprises (i) a VH comprising a VH CDR1 having an amino acid sequence selected from SEQ ID NO: 103, SEQ ID NO: 109, SEQ ID NO: 115, SEQ ID NO: 121, and SEQ ID NO: 127; a VH CDR2 having an amino acid sequence selected from SEQ ID NO: 104, SEQ ID NO: 110, SEQ ID NO: 116, SEQ ID NO: 122, and SEQ ID NO: 128; a VH CDR3 having an amino acid sequence selected from SEQ ID NO: 105, SEQ ID NO: 111, SEQ ID NO: 117, SEQ ID NO: 123, and SEQ ID NO: 129; and (ii) a VL comprising a VL CDR1 having an amino acid sequence selected from SEQ ID NO: 106, SEQ ID NO: 112, SEQ ID NO: 118, SEQ ID NO: 124, and SEQ ID NO: 130; a VL CDR2 having an amino acid sequence selected from SEQ ID NO: 107, SEQ ID NO: 113, SEQ ID NO: 119, SEQ ID NO: 125, and SEQ ID NO: 131; a VL CDR3 having an amino acid sequence selected from SEQ ID NO: 108, SEQ ID NO: 114, SEQ ID NO: 120, SEQ ID NO: 126, and SEQ ID NO: 132.

In some embodiments, the antibody further comprises one or more framework regions as set forth in in SEQ ID NO: 31, SEQ ID NO: 32, SEQ ID NO: 65, SEQ ID NO: 66, SEQ ID NO: 99, SEQ ID NO: 100, SEQ ID NO: 133 and/or SEQ ID NO: 134.

In some embodiments, the antibody comprises a VH having an amino acid sequence selected from SEQ ID NO: 31, SEQ ID NO: 65, SEQ ID NO: 99, and SEQ ID NO: 133, and a VL having an amino acid sequence selected from SEQ ID NO: 32, SEQ ID NO: 66, SEQ ID NO: 100, and SEQ ID NO: 134.

In some embodiments, the antibody provided herein comprises a VH having an amino acid sequence of SEQ ID NO: 31, and a VL having an amino acid sequence of SEQ ID NO: 32. In some embodiments, the antibody provided herein comprises a VH having an amino acid sequence of SEQ ID NO: 65, and a VL having an amino acid sequence of SEQ ID NO: 66. In some embodiments, the antibody provided herein comprises a VH having an amino acid sequence of SEQ ID NO: 99, and a VL having an amino acid sequence of SEQ ID NO: 100. In some embodiments, the antibody provided herein comprises a VH having an amino acid sequence of SEQ ID NO: 133, and a VL having an amino acid sequence of SEQ ID NO: 134.

In some embodiments, the antibody is a humanized antibody. In some embodiments, the antibody is an IgG antibody. In some embodiments, the IgG antibody is an IgG1, IgG2, IgG3, or IgG4 antibody. In some embodiments, the antibody comprises a kappa light chain. In some embodiments, the antibody comprises a lambda light chain. In some embodiments, the antibody is a monoclonal antibody.

In some embodiments, the antibody binds a CD28 antigen. In some embodiments, the antibody binds a CD28 epitope. In some embodiments, the antibody specifically binds to CD28. In some embodiments, the VH CDR1, VH CDR2, VH CDR3, VL CDR1, VL CDR2 and VL CDR3 form a binding site for an antigen of the CD28. In some embodiments, the VH CDR1, VH CDR2, VH CDR3, VL CDR1, VL CDR2 and VL CDR3 form a binding site for an epitope of the CD28. In some embodiments, the CD28 is present on the surface of a T cell.

In some embodiments, the antibody is multivalent. In some embodiments, the antibody is capable of binding at least three antigens. In some embodiments, the antibody is capable of binding at least four antigens. In some embodiments, the antibody is capable of binding at least five antigens. In some embodiments, the antibody is a multispecific antibody. In some embodiments, the antibody is a bispecific antibody. In some embodiments, the antibody is a trispecific antibody. In some embodiments, the antibody is a quadraspecific antibody.

In another aspect, provided is a multispecific antibody, wherein the multispecific antibody comprises a first binding domain that binds to CD28 and a second binding domain that binds to a second target that is not CD28. In some embodiments, the first binding domain that binds to CD28 comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:31; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:32. In some embodiments, the first binding domain that binds to CD28 comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:65; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:66. In some embodiments, the first binding domain that binds to CD28 comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:99; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:100. In some embodiments, the first binding domain that binds to CD28 comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:133; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:134. In some embodiments, the VH CDR1, VH CDR2, VH CDR3, VL CDR1, VL CDR2, and VL CDR3 amino acid sequences are according to the Kabat numbering system. In some embodiments, the VH CDR1, VH CDR2, VH CDR3, VL CDR1, VL CDR2, and VL CDR3 amino acid sequences are according to the Chothia numbering system. In some embodiments, the VH CDR1, VH CDR2, VH CDR3, VL CDR1, VL CDR2, and VL CDR3 amino acid sequences are according to the AbM numbering system. In some embodiments, the VH CDR1, VH CDR2, VH CDR3, VL CDR1, VL CDR2, and VL CDR3 amino acid sequences are according to the Contact numbering system. In some embodiments, the VH CDR1, VH CDR2, VH CDR3, VL CDR1, VL CDR2, and VL CDR3 amino acid sequences are according to the IMGT numbering system.

In some embodiments, the first binding domain that binds CD28 provided herein comprises (i) a VH comprising a VH CDR1 having an amino acid sequence selected from SEQ ID NO:1, SEQ ID NO:7, SEQ ID NO:13, SEQ ID NO:19, and SEQ ID NO:25; a VH CDR2 having an amino acid sequence selected from SEQ ID NO:2, SEQ ID NO:8, SEQ ID NO:14, SEQ ID NO:20, and SEQ ID NO:26; a VH CDR3 having an amino acid sequence selected from SEQ ID NO:3, SEQ ID NO:9, SEQ ID NO:15, SEQ ID NO:21, and SEQ ID NO:27; (ii) a VL comprising a VL CDR1 having an amino acid sequence selected from SEQ ID NO:4, SEQ ID NO:10, SEQ ID NO:16, SEQ ID NO:22, and SEQ ID NO:28; a VL CDR2 having an amino acid sequence selected from SEQ ID NO:5, SEQ ID NO:11, SEQ ID NO:17, SEQ ID NO:23, and SEQ ID NO:29; a VL CDR3 having an amino acid sequence selected from SEQ ID NO:6, SEQ ID NO:12, SEQ ID NO:18, SEQ ID NO:24, and SEQ ID NO:30.

In some embodiments, the first binding domain that binds CD28 provided herein comprises (i) a VH comprising a VH CDR1 having an amino acid sequence selected from SEQ ID NO:35, SEQ ID NO:41, SEQ ID NO:47, SEQ ID NO:53, and SEQ ID NO:59; a VH CDR2 having an amino acid sequence selected from SEQ ID NO:36, SEQ ID NO:42, SEQ ID NO:48, SEQ ID NO:54, and SEQ ID NO:60; a VH CDR3 having an amino acid sequence selected from SEQ ID NO:37, SEQ ID NO:43, SEQ ID NO:49, SEQ ID NO:55, and SEQ ID NO:61; and (ii) a VL comprising a VL CDR1 having an amino acid sequence selected from SEQ ID NO:38, SEQ ID NO:44, SEQ ID NO:50, SEQ ID NO:56, and SEQ ID NO:62; a VL CDR2 having an amino acid sequence selected from SEQ ID NO:39, SEQ ID NO:45, SEQ ID NO:51, SEQ ID NO:57, and SEQ ID NO:63; a VL CDR3 having an amino acid sequence selected from SEQ ID NO:40, SEQ ID NO:46, SEQ ID NO:52, SEQ ID NO:58, and SEQ ID NO:64.

In some embodiments, the first binding domain that binds CD28 provided herein comprises (i) a VH comprising a VH CDR1 having an amino acid sequence selected from SEQ ID NO:69, SEQ ID NO:75, SEQ ID NO:81, SEQ ID NO:87, and SEQ ID NO:93; a VH CDR2 having an amino acid sequence selected from SEQ ID NO:70, SEQ ID NO:76, SEQ ID NO:82, SEQ ID NO:88, and SEQ ID NO:94; a VH CDR3 having an amino acid sequence selected from SEQ ID NO:71, SEQ ID NO:77, SEQ ID NO:83, SEQ ID NO:89, and SEQ ID NO:95; and (ii) a VL comprising a VL CDR1 having an amino acid sequence selected from SEQ ID NO:72, SEQ ID NO:78, SEQ ID NO:84, SEQ ID NO:90, and SEQ ID NO:96; a VL CDR2 having an amino acid sequence selected from SEQ ID NO:73, SEQ ID NO:79, SEQ ID NO:85, SEQ ID NO:91, and SEQ ID NO:97; a VL CDR3 having an amino acid sequence selected from SEQ ID NO:74, SEQ ID NO:80, SEQ ID NO:86, SEQ ID NO:92, and SEQ ID NO:98.

In some embodiments, the first binding domain that binds CD28 provided herein comprises (i) a VH comprising a VH CDR1 having an amino acid sequence selected from SEQ ID NO:103, SEQ ID NO:109, SEQ ID NO:115, SEQ ID NO:121, and SEQ ID NO:127; a VH CDR2 having an amino acid sequence selected from SEQ ID NO:104, SEQ ID NO:110, SEQ ID NO:116, SEQ ID NO:122, and SEQ ID NO:128; a VH CDR3 having an amino acid sequence selected from SEQ ID NO:105, SEQ ID NO:111, SEQ ID NO:117, SEQ ID NO:123, and SEQ ID NO:129; and (ii) a VL comprising a VL CDR1 having an amino acid sequence selected from SEQ ID NO:106, SEQ ID NO:112, SEQ ID NO:118, SEQ ID NO:124, and SEQ ID NO:130; a VL CDR2 having an amino acid sequence selected from SEQ ID NO:107, SEQ ID NO:113, SEQ ID NO:119, SEQ ID NO:125, and SEQ ID NO:131; a VL CDR3 having an amino acid sequence selected from SEQ ID NO:108, SEQ ID NO:114, SEQ ID NO:120, SEQ ID NO:126, and SEQ ID NO:132.

In some embodiments, the first binding domain further comprises one or more framework regions as set forth in in SEQ ID NO:31, SEQ ID NO:32, SEQ ID NO:65, SEQ ID NO:66, SEQ ID NO:99, SEQ ID NO:100, SEQ ID NO:133 and/or SEQ ID NO:134.

In some embodiments, the first binding domain comprises a VH having an amino acid sequence selected from SEQ ID NO:31, SEQ ID NO:65, SEQ ID NO:99, and SEQ ID NO:133, and a VL having an amino acid sequence selected from SEQ ID NO:32, SEQ ID NO:66, SEQ ID NO:100, and SEQ ID NO:134.

In some embodiments, the first binding domain provided herein comprises a VH having an amino acid sequence of SEQ ID NO:31, and a VL having an amino acid sequence of SEQ ID NO:32. In some embodiments, the first binding domain provided herein comprises a VH having an amino acid sequence of SEQ ID NO:65, and a VL having an amino acid sequence of SEQ ID NO:66. In some embodiments, the first binding domain provided herein comprises a VH having an amino acid sequence of SEQ ID NO:99, and a VL having an amino acid sequence of SEQ ID NO:100. In some embodiments, the first binding domain provided herein comprises a VH having an amino acid sequence of SEQ ID NO:133, and a VL having an amino acid sequence of SEQ ID NO:134.

In some embodiments, the antibody is a humanized antibody. In some embodiments, the antibody is an IgG antibody. In some embodiments, the IgG antibody is an IgG1, IgG2, IgG3, or IgG4 antibody. In some embodiments, the antibody comprises a kappa light chain. In some embodiments, the antibody comprises a lambda light chain. In some embodiments, the antibody is a monoclonal antibody.

In some embodiments, the multispecific antibody is a humanized antibody. In some embodiments, the multispecific antibody is an IgG antibody. In some embodiments, the IgG antibody is an IgG1, IgG2, IgG3, or IgG4 antibody. In some embodiments, the multispecific antibody comprises a kappa light chain. In some embodiments, the multispecific antibody comprises a lambda light chain. In some embodiments, the multispecific antibody is a monoclonal antibody.

In some embodiments, the first binding domain binds a CD28 antigen. In some embodiments, first binding domain binds a CD28 epitope. In some embodiments, the first binding domain specifically binds to CD28. In some embodiments, the VH CDR1, VH CDR2, VH CDR3, VL CDR1, VL CDR2 and VL CDR3 of the first binding domain form a binding site for an antigen of the CD28. In some embodiments, the VH CDR1, VH CDR2, VH CDR3, VL CDR1, VL CDR2 and VL CDR3 of the first binding domain form a binding site for an epitope of the CD28. In some embodiments, the CD28 is present on the surface of a T cell.

In some embodiments, the second binding domain binds an antigen of the second target. In some embodiments, the second binding domain binds an epitope of the second target. In some embodiments, the second binding domain specifically binds to the second target. In some embodiments, the VH CDR1, VH CDR2, VH CDR3, VL CDR1, VL CDR2 and VL CDR3 of the second binding domain form a binding site for an antigen of the second target. In some embodiments, the VH CDR1, VH CDR2, VH CDR3, VL CDR1, VL CDR2 and VL CDR3 of the second binding domain form a binding site for an epitope of the second target. In some embodiments, the second target is present on the surface of a second cell.

In some embodiments, the multispecific antibody is multivalent. In some embodiments, the multispecific antibody is capable of binding at least three antigens. In some embodiments, the multispecific antibody is capable of binding at least four antigens. In some embodiments, the multispecific antibody is capable of binding at least five antigens. In some embodiments, wherein the multispecific antibody is a bispecific antibody. In some embodiments, the multispecific antibody is a trispecific antibody. In some embodiments, the multispecific antibody is a quadraspecific antibody. In some embodiments, the multispecific antibody further comprises: a third binding domain that binds to a third target. In some embodiments, the multispecific antibody further comprises a fourth binding domain that binds to a fourth target.

In another aspect, provided is a multispecific antibody comprising: a first means capable of binding CD28 on the surface of a cell; and a second means capable of binding a second target antigen that is not CD28.

In another aspect, provided is a nucleic acid encoding a CD28 antibody provided herein. In one aspect, provided is a vector comprising a nucleic acid encoding a CD28 antibody provided herein. In another aspect, provided is a host cell comprising a vector comprising a nucleic acid encoding a CD28 antibody provided herein. In another aspect, provided is a kit comprising a vector comprising a nucleic acid encoding a CD28 antibody provided herein, and packaging for the same. In another aspect, provided is a kit comprising a CD28 antibody provided herein. In certain embodiments, the CD28 antibody is a multispecific CD28 antibody.

In another aspect provided is a pharmaceutical composition comprising a CD28 antibody provided herein, and a pharmaceutically acceptable carrier. In one aspect, provided is a method of producing a pharmaceutical composition comprising a CD28 antibody provided herein, and a pharmaceutically acceptable carrier, wherein the method comprises combining the antibody with a pharmaceutically acceptable carrier to obtain the pharmaceutical composition. In certain embodiments, the CD28 antibody is a multispecific CD28 antibody.

In another aspect, provided is a method of activating a T cell expressing CD28, comprising contacting the T cell with a CD28 antibody provided herein. In some embodiments, the contacting results in an increase in CD69, CD25, and/or Granzyme B expression, as compared to a control T cell expressing CD28.

In another aspect, provided is a process for making an antibody that binds to more than one target molecule, the molecule comprising: a step for performing a function of obtaining a binding domain capable of binding to CD28 on the surface of a cell; a step for performing a function of obtaining a binding domain capable of binding to a second target antigen on a second cell; and a step for performing a function of providing an antibody capable of binding to a CD28 on the surface of a cell and a second target antigen on a second cell. In some embodiments, the step for performing a function of obtaining a binding domain capable of binding to a second target antigen is repeated n times and further comprising n steps for performing a function of providing a binding domain capable of binding to CD28 on the surface of a cell and n number of target molecules, wherein n is at least 2.

In another aspect, provided is a method of directing a cell expressing CD28 to a second target, the method comprising contacting the CD28-expressing cell with a multispecific CD28 antibody provided herein, wherein the contacting directs the CD28-expressing cell to the second target.

In another aspect, provided is a method of inhibiting growth or proliferation of target cells expressing a second target, the method comprising contacting the target cells with a multispecific CD28 antibody provided herein, wherein contacting the target cells with the multispecific antibody inhibits growth or proliferation of the target cells. In some embodiments, the target cells are in the presence of a CD28-expressing cell while in contact with the multispecific antibody.

In another aspect, provided is a method for eliminating target cells expressing the second target in a subject, comprising administering an effective amount of a multispecific CD28 antibody provided herein to the subject.

In another aspect, provided is a method for treating a disease caused all or in part by target cells expressing the second target in a subject, comprising administering an effective amount of a multispecific CD28 antibody provided herein to the subject.

BRIEF DESCRIPTION OF THE DRAWINGS

The foregoing summary, as well as the following detailed description of specific embodiments of the present application, will be better understood when read in conjunction with the appended drawings. It should be understood, however, that the application is not limited to the precise embodiments shown in the drawings.

FIG. 3A shows CD25 activation of Vβ17+ T cells at 96 hrs. FIG. 3B shows CD71 activation of Vβ17+ T cells at 96 hrs. FIG. 3C shows proliferation of Vβ17+ T cells at 96 hrs.

FIGS. 4A-4B show activation of Vβ17 T cells by upregulation of CD25 in the presence of H929 cells at 96 hrs. FIGS. 4C-4D show activation of Vβ17 T cells by upregulation of CD71 in the presence of H929 cells at 96 hrs. FIGS. 4E-4G show proliferation of Vβ17 T cells in the presence of H929 cells at 96 hrs.

FIG. 5A shows LAG3 was induced only on a small fraction of the Vβ17 T cells and no upregulation was seen on the Vβ17− T cells. Overall, only 20% of the Vβ17 T cells were found to express LAG3. FIG. 5B shows PD1 to be upregulated on Vβ17+ T cells in the presence of both the Vβ17×BCMA antibodies and the Vβ17×CD28×BCMA antibodies. FIG. 5C shows TIM3 was induced only on a small fraction of the Vβ17 T cells and no upregulation was seen on the Vβ17− T cells. Overall, only 20% of the Vβ17 T cells were found to express TIM3 cells.

FIG. 6A shows cytotoxicity mediated by anti-Vβ17/anti-BCMA/anti-CD28 trispecific antibodies. FIG. 6B shows cytotoxicity mediated by anti-Vβ17/anti-BCMA/anti-CD28 trispecific antibodies. FIG. 6C shows cytotoxicity mediated by anti-Vβ17/anti-BCMA/anti-CD28 trispecific antibodies.

FIGS. 7A-7D show Vβ17×

CD28×BCMA bispecific antibodies showed superior cytokine release in comparison to Vβ17×BCMA antibodies and Null×CD28×BCMA antibodies (four different donors).

Figure 8:
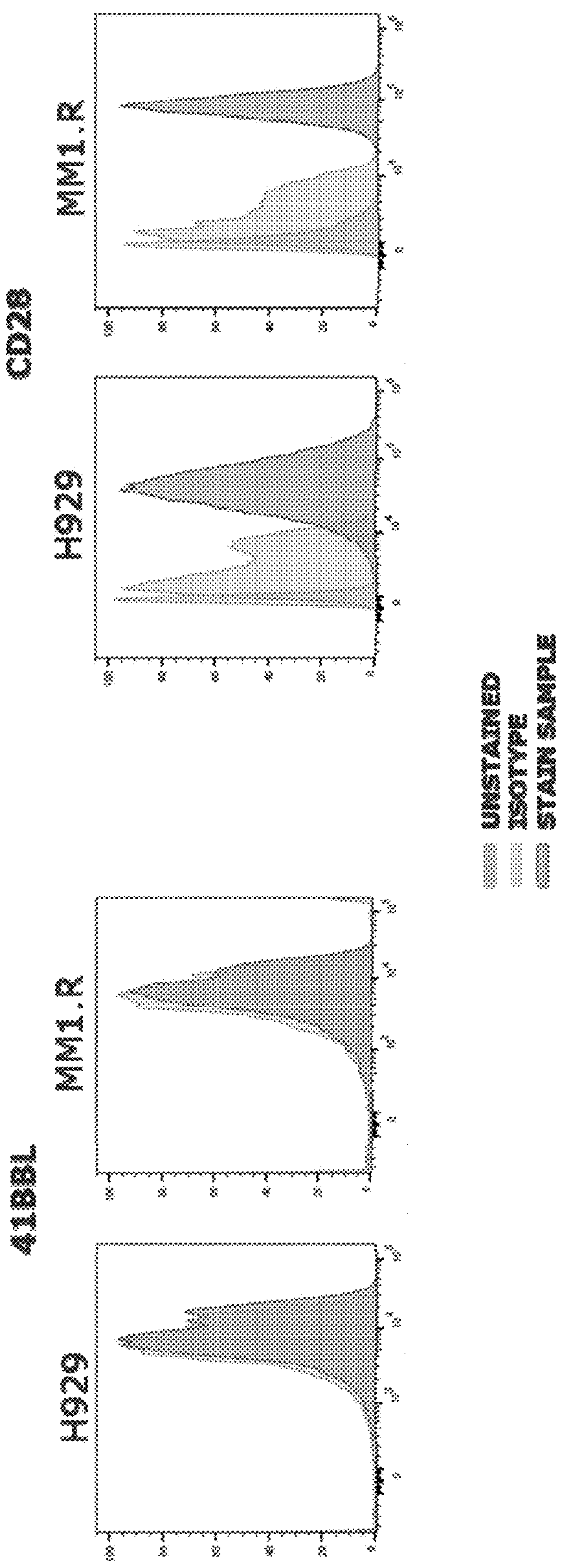

FIG. 8 shows expression of co-stimulatory ligands on BCMA expression in H929 cell lines. Both tested multiple myeloma cell lines, MM1.R and H929 were found to express CD28, while no expression of 4IBBL was observed on either of the cell lines.

DETAILED DESCRIPTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series.

Those skilled in the art will recognize or be able to ascertain using no more than routine experimentation, many equivalents to the specific embodiments described herein. Such equivalents are intended to been compassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc. In a specific embodiments, the subject is a human.

It should also be understood that the terms "about," "approximately," "generally," "substantially," and like terms, used herein when referring to a dimension or characteristic of a component of embodiments provided herein, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., CD28 antibody and polynucleotides that encode them, CD28 polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when:

the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the term "vector" is a replicon in which another nucleic acid segment can be operably inserted so as to bring about the replication or expression of the segment.

As used herein, the term "host cell" refers to a cell comprising a nucleic acid molecule provided herein. The "host cell" can be any type of cell, e.g., a primary cell, a cell in culture, or a cell from a cell line. In one embodiment, a "host cell" is a cell transfected with a nucleic acid molecule provided herein. In another embodiment, a "host cell" is a progeny or potential progeny of such a transfected cell. A progeny of a cell may or may not be identical to the parent cell, e.g., due to mutations or environmental influences that can occur in succeeding generations or integration of the nucleic acid molecule into the host cell genome.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed antibody can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The conventional one-letter or three-letter code for amino acid residues is used herein. The terms "peptide," "polypeptide," and "protein" can be used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Antibodies

Provided herein are CD28 antibodies or antigen-binding fragments thereof, nucleic acids and expression vectors encoding the antibodies, recombinant cells containing the vectors, and compositions comprising the antibodies. Methods of making the antibodies, and methods of using the antibodies to treat diseases are also provided. The antibodies disclosed herein possess one or more desirable functional properties, including but not limited to high-affinity binding to CD28 or high specificity to CD28. In certain embodiments, the antibodies disclosed herein possess the ability to treat or prevent a disease or disorder when administered to a subject alone or in combination with other therapies.

Also provided herein are CD28 bispecific antibodies or antigen-binding fragments thereof, nucleic acids and expression vectors encoding the bispecific antibodies, recombinant cells containing the vectors, and compositions comprising the bispecific antibodies. Methods of making the antibodies, and methods of using the bispecific antibodies to treat diseases, including cancer, are also provided. The antibodies disclosed herein possess one or more desirable functional properties. In some embodiments, the bispecific antibodies provided herein have high-affinity binding to CD28. In some embodiments, the bispecific antibodies provided herein have high-affinity binding to a second target antigen. In some embodiments, the bispecific antibodies provided herein have high specificity to CD28. In some embodiments, the bispecific antibodies provided herein have high specificity to a second target antigen. In some, embodiments, the bispecific antibodies provided herein have high specificity to a second target that is not CD28. In some embodiments, the bispecific antibodies provided herein have the ability to treat or prevent a disease or disorder when administered alone. In some embodiments, the bispecific antibodies provided herein have the ability to treat or prevent a disease or disorder when administered in combination with other therapies.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies provided herein can be of any of the five major classes or corresponding sub-classes. In specific embodiments, the antibodies provided herein are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies provided herein can, in certain embodiments, contain a kappa light chain constant domain. The antibodies provided herein can, in certain embodiments, also contain a lambda light chain constant domain. According to particular embodiments, the antibodies provided herein include heavy and/or light chain constant regions from rat or human antibodies. In specific embodiments, the constant region is a human constant region.

In addition to the heavy and light constant domains, antibodies contain an antigen-binding region that is made up of a light chain variable region (VL) and a heavy chain variable region (VH), each of which contains three domains (i.e., complementarity determining regions 1 (CDR1), CDR2 and CDR3. A "CDR" refers to one of three hypervariable regions (HCDR1, HCDR2 or HCDR3) within the non-framework region of the immunoglobulin (Ig or antibody) VH β-sheet framework, or one of three hypervariable regions (LCDR1, LCDR2 or LCDR3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. CDR region sequences have also been defined by AbM, Contact and IMGT. Exemplary CDR region sequences are illustrated herein, for example, in the tables provided in the Examples below. The positions of CDRs within a canonical antibody variable region have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra (1997)). Such nomenclature is similarly well known to those skilled in the art.

The light chain variable region CDR1 domain is interchangeably referred to herein as LCDR1 or VL CDR1. The light chain variable region CDR2 domain is interchangeably referred to herein as LCDR2 or VL CDR2. The light chain variable region CDR3 domain is interchangeably referred to herein as LCDR3 or VL CDR3. The heavy chain variable region CDR1 domain is interchangeably referred to herein as HCDR1 or VH CDR1. The heavy chain variable region CDR2 domain is interchangeably referred to herein as HCDR2 or VH CDR2. The heavy chain variable region CDR1 domain is interchangeably referred to herein as HCDR3 or VH CDR3.

The term "hypervariable region", such as a VH or VL, when used herein refers to the regions of an antibody variable region that are hypervariable in sequence and/or form structurally defined loops. Generally, antibodies comprise six hypervariable regions; three in the VH (HCDR1, HCDR2, HCDR3), and three in the VL (LCDR1, LCDR2, LCDR3). A number of hypervariable region delineations are in use and are encompassed herein. The "Kabat" CDRs are based on sequence variability and are the most commonly used (see, e.g., Kabat et al., *Sequences of Proteins of Immunological Interest,* 5th Ed. Public Health Service, National Institutes of Health, Bethesda, MD. (1991)).

"Chothia" refers instead to the location of the structural loops (see, e.g., Chothia and Lesk, *J. Mol. Biol.* 196:901-917 (1987)). The end of the Chothia CDR-HCDR1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The "AbM" hypervariable regions represent a compromise between the Kabat CDRs and Chothia structural loops, and are used by Oxford Molecular's AbM antibody modeling software (see, e.g., Martin, in *Antibody Engineering*, Vol. 2, Chapter 3, Springer Verlag). "Contact" hypervariable regions are based on an analysis of the available complex crystal structures.

Recently, a universal numbering system has been developed and widely adopted, ImMunoGeneTics (IMGT) Information System® (Lafranc et al., *Dev. Comp. Immunol.* 27(1):55-77 (2003)). IMGT is an integrated information system specializing in immunoglobulins (IG), T cell receptors (TR) and major histocompatibility complex (MEW) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Plückthun, *J. Mol. Biol.* 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). An Exemplary system, shown herein, combines Kabat and Chothia.

| | Exemplary | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (LCDR1), 46-56 or 50-56 (LCDR2) and 89-97 or 89-96 (LCDR3) in the VL and 26-35 or 26-35A (HCDR1), 50-65 or 49-65 (HCDR2) and 93-102, 94-102, or 95-102 (HCDR3) in the VH. CDR sequences, reflecting each of the above numbering schemes, are provided herein, including in Tables 1-6.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable region, which contains the antigen binding site. The constant region may contain the CH1, CH2 and CH3 regions of the heavy chain and the CL region of the light chain.

The term "framework" or "FR" residues are those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

As used herein, the term an "isolated antibody" refers to an antibody which is substantially free of other antibodies having different antigenic specificities (e.g., an isolated antibody that specifically binds to CD28 is substantially free of antibodies that do not bind to CD28). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that can be present in minor amounts. Monoclonal antibodies provided herein can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), a single domain antibody (sdAb) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecific antibody" refers to a multispecific antibody that binds no more than two epitopes or two antigens. A bispecific antibody is characterized by a first immunoglobulin variable domain sequence which has binding specificity for a first epitope (e.g., an epitope on a CD28 antigen) and a second immunoglobulin variable domain sequence that has binding specificity for a second epitope. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on CD28 and the second epitope is located on second target that is not CD28.

As used herein, the term "CD28" refers to Cluster of Differentiation 28, which is constitutively expressed on the surface of T cells and some natural killer cells. CD28 is also expressed on some B cells. CD28 is a type I transmembrane glycoprotein and is a member of the Immunoglobulin family by virtue of its single Ig variable-like extracellular domain. The term "CD28" includes any CD28 variant, isoform, and species homolog, which is naturally expressed by cells (including T cells) or can be expressed on cells transfected with genes or cDNA encoding the polypeptide. Unless noted, preferably the CD28 is a human CD28. An exemplary human CD28 amino acid sequence is disclosed in NCBI Accession No. NP_006130.

As used herein, an antibody that "specifically binds to CD28" refers to an antibody that binds to a CD28, preferably a human CD28, with a KD of $1\times10^{-7}$ M or less, preferably $1\times10^{-8}$M or less, more preferably $5\times10^{-9}$ M or less, $1\times10^{-9}$ M or less, $5\times10^{-10}$ M or less, or $1\times10^{-10}$ M or less.

As used herein, an antibody that "specifically binds to a second target" refers to an antibody that binds to a second target with a KD of $1\times10^{-7}$ M or less, such as $1\times10^{-8}$M or less, $5\times10^{-9}$M or less, $1\times10^{-9}$M or less, $5\times10^{-10}$ M or less, or $1\times10^{-10}$ M or less.

The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system. The smaller the value of the KD of an antibody, the higher affinity that the antibody binds to a target antigen.

In one aspect, provided herein is an antibody that binds to CD28. In some embodiments, the antibody comprises a heavy chain variable region and a light chain variable region. In a some embodiments, the CD28 antibody is not a single domain antibody or nanobody. In some embodiments, the CD28 antibody is a humanized antibody.

In certain embodiments, provided herein is a CD28 antibody comprising a VH region, VL region, VH CDR1, VH CDR2, VH CDR3, VL CDR1, VL CDR2, and/or VL CDR3 of any one of the antibodies described herein. In some embodiments, provided herein is a CD28 antibody comprising a VH region of any one of the antibodies described herein. In some embodiments, provided herein is a CD28 antibody comprising a VL region of any one of the antibodies described herein. In some embodiments, provided herein is a CD28 antibody comprising a VH region of any one of the antibodies described herein, and a VL region of any one of the antibodies described herein. In some embodiments, provided herein is a CD28 antibody comprising a VH CDR1, VH CDR2, and VH CDR3 of any one of the antibodies described herein. In some embodiments, provided herein is a CD28 antibody comprising a VL CDR1, VL CDR2, and VL CDR3 of any one of the antibodies described herein. In some embodiments, provided herein is a CD28 antibody comprising a VH CDR1, VH CDR2, and VH CDR3 of any one of the antibodies described herein; and a VL CDR1, VL CDR2, and VL CDR3 of any one of the antibodies described herein. Representative VH and VL amino acid sequences, including VH CDR1, VH CDR2, VH CDR3, VL CDR1, VL CDR2 and VL CDR3 amino acid sequences, of CD28 antibodies provided herein are provided in Tables 1-6. In some embodiments, the antibody that binds CD28 provided herein comprises (i) a VH comprising a VH CDR1 having an amino acid sequence selected from SEQ ID NO:1, SEQ ID NO:7, SEQ ID NO:13, SEQ ID NO:19, and SEQ ID NO:25; a VH CDR2 having an amino acid sequence selected from SEQ ID NO:2, SEQ ID NO:8, SEQ ID NO:14, SEQ ID NO:20, and SEQ ID NO:26; a VH CDR3 having an amino acid sequence selected from SEQ ID NO:3, SEQ ID NO:9, SEQ ID NO:15, SEQ ID NO:21, and SEQ ID NO:27; (ii) a VL comprising a VL CDR1 having an amino acid sequence selected from SEQ ID NO:4, SEQ ID NO:10, SEQ ID NO:16, SEQ ID NO:22, and SEQ ID NO:28; a VL CDR2 having an amino acid sequence selected from SEQ ID NO:5, SEQ ID NO:11, SEQ ID NO:17, SEQ ID NO:23, and SEQ ID NO:29; a VL CDR3 having an amino acid sequence selected from SEQ ID NO:6, SEQ ID NO:12, SEQ ID NO:18, SEQ ID NO:24, and SEQ ID NO:30. In some embodiments, the antibody that binds CD28 provided herein comprises (i) a VH comprising a VH CDR1 having an amino acid sequence selected from SEQ ID NO:35, SEQ ID NO:41, SEQ ID NO:47, SEQ ID NO:53, and SEQ ID NO:59; a VH CDR2 having an amino acid sequence selected from SEQ ID NO:36, SEQ ID NO:42, SEQ ID NO:48, SEQ ID NO:54, and SEQ ID NO:60; a VH CDR3 having an amino acid sequence selected from SEQ ID NO:37, SEQ ID NO:43, SEQ ID NO:49, SEQ ID NO:55, and SEQ ID NO:61; and (ii) a VL comprising a VL CDR1 having an amino acid sequence selected from SEQ ID NO:38, SEQ ID NO:44, SEQ ID NO:50, SEQ ID NO:56, and SEQ ID NO:62; a VL CDR2 having an amino acid sequence selected from SEQ ID NO:39, SEQ ID NO:45, SEQ ID NO:51, SEQ ID NO:57, and SEQ ID NO:63; a VL CDR3 having an amino acid sequence selected from SEQ ID NO:40, SEQ ID NO:46, SEQ ID NO:52, SEQ ID NO:58, and SEQ ID NO:64. In some embodiments, the antibody that binds CD28 provided herein comprises (i) a VH comprising a VH CDR1 having an amino acid sequence selected from SEQ ID NO:69, SEQ ID NO:75, SEQ ID NO:81, SEQ ID NO:87, and SEQ ID NO:93; a VH CDR2 having an amino acid sequence selected from SEQ ID NO:70, SEQ ID NO:76, SEQ ID NO:82, SEQ ID NO:88, and SEQ ID NO:94; a VH CDR3 having an amino acid sequence selected from SEQ ID NO:71, SEQ ID NO:77, SEQ ID NO:83, SEQ ID NO:89, and SEQ ID NO:95; and (ii) a VL comprising a VL CDR1 having an amino acid sequence selected from SEQ ID NO:72, SEQ ID NO:78, SEQ ID NO:84, SEQ ID NO:90, and SEQ ID NO:96; a VL CDR2 having an amino acid sequence selected from SEQ ID NO:73, SEQ ID NO:79, SEQ ID NO:85, SEQ ID NO:91, and SEQ ID NO:97; a VL CDR3 having an amino acid sequence selected from SEQ ID NO:74, SEQ ID NO:80, SEQ ID NO:86, SEQ ID NO:92, and SEQ ID NO:98. In some embodiments, the antibody that binds CD28 provided herein comprises (i) a VH comprising a VH CDR1 having an amino acid sequence selected from SEQ ID NO:103, SEQ ID NO:109, SEQ ID NO:115, SEQ ID NO:121, and SEQ ID NO:127; a VH CDR2 having an amino acid sequence selected from SEQ ID NO:104, SEQ ID NO:110, SEQ ID NO:116, SEQ ID NO:122, and SEQ ID NO:128; a VH CDR3 having an amino acid sequence selected from SEQ ID NO:105, SEQ ID NO:111, SEQ ID NO:117, SEQ ID NO:123, and SEQ ID NO:129; and (ii) a VL comprising a VL CDR1 having an amino acid sequence selected from SEQ ID NO:106, SEQ ID NO:112, SEQ ID NO:118, SEQ ID NO:124, and SEQ ID NO:130; a VL CDR2 having an amino acid sequence selected from SEQ ID NO:107, SEQ ID NO:113, SEQ ID NO:119, SEQ ID NO:125, and SEQ ID NO:131; a VL CDR3 having an amino acid sequence selected from SEQ ID NO:108, SEQ ID NO:114, SEQ ID NO:120, SEQ ID NO:126, and SEQ ID NO:132. In some embodiments, the antibody provided herein comprises a VH having an amino acid sequence of SEQ ID NO:31, and a VL having an amino acid sequence of SEQ ID NO:32. In some embodiments, the antibody provided herein comprises a VH having an amino acid sequence of SEQ ID NO:65, and a VL having an amino acid sequence of SEQ ID NO:66. In some embodiments, the antibody provided herein comprises a VH having an amino acid sequence of SEQ ID NO:99, and a VL having an amino acid sequence of SEQ ID NO:100. In some embodiments, the antibody provided herein comprises a VH having an amino acid sequence of SEQ ID NO:133, and a VL having an amino acid sequence of SEQ ID NO:134.

In certain embodiments, provided herein is a CD28 bispecific antibody comprising a binding domain that binds to CD28 having a VH region, VL region, VH CDR1, VH CDR2, VH CDR3, VL CDR1, VL CDR2, and/or VL CDR3 of any one of the antibodies described herein. In some embodiments, provided herein is a CD28 bispecific antibody comprising a binding domain that binds to CD28 having a VH region of any one of the antibodies described herein. In some embodiments, provided herein is a CD28 bispecific antibody comprising a binding domain that binds to CD28 having a VL region of any one of the antibodies described herein. In some embodiments, provided herein is a CD28 bispecific antibody comprising a binding domain that binds to CD28 having a VH region of any one of the antibodies described herein, and a VL region of any one of the antibodies described herein. In some embodiments, provided herein is a CD28 bispecific antibody comprising a binding domain that binds to CD28 having a VH CDR1, VH CDR2, and VH CDR3 of any one of the antibodies described. In some embodiments, provided herein is a CD28 bispecific antibody comprising a binding domain that binds to CD28 having a VL CDR1, VL CDR2, and VL CDR3 of any one of the antibodies described herein. In some embodiments, provided herein is a CD28 bispecific antibody comprising a binding domain that binds to CD28 having a VH CDR1, VH CDR2, and VH CDR3 of any one of the antibodies described herein; and a VL CDR1, VL CDR2, and VL CDR3 of any one of the antibodies described herein. In certain embodiments, the CD28 antibody is a bispecific antibody. In some embodiments, the CD28 bispecific antibody further comprises a second binding domain that binds to a second target that is not CD28 having a VH region, VL region, VH CDR1, VH CDR2, VH CDR3, VL CDR1, VL CDR2, and/or VL CDR3 of a second target that is not CD28 antibody provided herein. In some embodiments, the CD28 bispecific antibody further comprises a second binding domain that binds to a second target that is not CD28 having a VH region of a second target that is not CD28 antibody provided herein. In some embodiments, the CD28 bispecific antibody further comprises a second binding domain that binds to a second target that is not CD28 having a VL region of a second target that is not CD28 antibody provided herein. In some embodiments, the CD28 bispecific antibody further comprises a second binding domain that binds to a second target that is not CD28 having a VH region of a second target that is not CD28 antibody provided herein, and a VL region of a second target that is not CD28 antibody provided herein. In some embodiments, the CD28 bispecific antibody further comprises a second binding domain that binds to a second target that is not CD28 having a VH CDR1, VH CDR2, and VH CDR3 of a second target that is not CD28 antibody provided herein. In some embodiments, the CD28 bispecific antibody further comprises a second binding domain that binds to a second target that is not CD28 having a VL CDR1, VL CDR2, and VL CDR3 of a second target that is not CD28 antibody provided herein. In some embodiments, the CD28 bispecific antibody further comprises a second binding domain that binds to a second target that is not CD28 having a VH CDR1, VH CDR2, and VH CDR3 of a second target that is not CD28 antibody provided herein, and a VL CDR1, VL CDR2, and VL CDR3 of a second target that is not CD28 antibody provided herein. In some embodiments, the CD28 binding domain provided herein comprises (i) a VH comprising a VH CDR1 having an amino acid sequence selected from SEQ ID NO:1, SEQ ID NO:7, SEQ ID NO:13, SEQ ID NO:19, and SEQ ID NO:25; a VH CDR2 having an amino acid sequence selected from SEQ ID NO:2, SEQ ID NO:8, SEQ ID NO:14, SEQ ID NO:20, and SEQ ID NO:26; a VH CDR3 having an amino acid sequence selected from SEQ ID NO:3, SEQ ID NO:9, SEQ ID NO:15, SEQ ID NO:21, and SEQ ID NO:27; (ii) a VL comprising a VL CDR1 having an amino acid sequence selected from SEQ ID NO:4, SEQ ID NO:10, SEQ ID NO:16, SEQ ID NO:22, and SEQ ID NO:28; a VL CDR2 having an amino acid sequence selected from SEQ ID NO:5, SEQ ID NO:11, SEQ ID NO:17, SEQ ID NO:23, and SEQ ID NO:29; a VL CDR3 having an amino acid sequence selected from SEQ ID NO:6, SEQ ID NO:12, SEQ ID NO:18, SEQ ID NO:24, and SEQ ID NO:30. In some embodiments, the CD28 binding domain provided herein comprises (i) a VH comprising a VH CDR1 having an amino acid sequence selected from SEQ ID NO:35, SEQ ID NO:41, SEQ ID NO:47, SEQ ID NO:53, and SEQ ID NO:59; a VH CDR2 having an amino acid sequence selected from SEQ ID NO:36, SEQ ID NO:42, SEQ ID NO:48, SEQ ID NO:54, and SEQ ID NO:60; a VH CDR3 having an amino acid sequence selected from SEQ ID NO:37, SEQ ID NO:43, SEQ ID NO:49, SEQ ID NO:55, and SEQ ID NO:61; and (ii) a VL comprising a VL CDR1 having an amino acid sequence selected from SEQ ID NO:38, SEQ ID NO:44, SEQ ID NO:50, SEQ ID NO:56, and SEQ ID NO:62; a VL CDR2 having an amino acid sequence selected from SEQ ID NO:39, SEQ ID NO:45, SEQ ID NO:51, SEQ ID NO:57, and SEQ ID NO:63; a VL CDR3 having an amino acid sequence selected from SEQ ID NO:40, SEQ ID NO:46, SEQ ID NO:52, SEQ ID NO:58, and SEQ ID NO:64. In some embodiments, the CD28 binding domain provided herein comprises (i) a VH comprising a VH CDR1 having an amino acid sequence selected from SEQ ID NO:69, SEQ ID NO:75, SEQ ID NO:81, SEQ ID NO:87, and SEQ ID NO:93; a VH CDR2 having an amino acid sequence selected from SEQ ID NO:70, SEQ ID NO:76, SEQ ID NO:82, SEQ ID NO:88, and SEQ ID NO:94; a VH CDR3 having an amino acid sequence selected from SEQ ID NO:71, SEQ ID NO:77, SEQ ID NO:83, SEQ ID NO:89, and SEQ ID NO:95; and (ii) a VL comprising a VL CDR1 having an amino acid sequence selected from SEQ ID NO:72, SEQ ID NO:78, SEQ ID NO:84, SEQ ID NO:90, and SEQ ID NO:96; a VL CDR2 having an amino acid sequence selected from SEQ ID NO:73, SEQ ID NO:79, SEQ ID NO:85, SEQ ID NO:91, and SEQ ID NO:97; a VL CDR3 having an amino acid sequence selected from SEQ ID NO:74, SEQ ID NO:80, SEQ ID NO:86, SEQ ID NO:92, and SEQ ID NO:98. In some embodiments, the CD28 binding domain provided herein comprises (i) a VH comprising a VH CDR1 having an amino acid sequence selected from SEQ ID NO:103, SEQ ID NO:109, SEQ ID NO:115, SEQ ID NO:121, and SEQ ID NO:127; a VH CDR2 having an amino acid sequence selected from SEQ ID NO:104, SEQ ID NO:110, SEQ ID NO:116, SEQ ID NO:122, and SEQ ID NO:128; a VH CDR3 having an amino acid sequence selected from SEQ ID NO:105, SEQ ID NO:111, SEQ ID NO:117, SEQ ID NO:123, and SEQ ID NO:129; and (ii) a VL comprising a VL CDR1 having an amino acid sequence selected from SEQ ID NO:106, SEQ ID NO:112, SEQ ID NO:118, SEQ ID NO:124, and SEQ ID NO:130; a VL CDR2 having an amino acid sequence selected from SEQ ID NO:107, SEQ ID NO:113, SEQ ID NO:119, SEQ ID NO:125, and SEQ ID NO:131; a VL CDR3 having an amino acid sequence selected from SEQ ID NO:108, SEQ ID NO:114, SEQ ID NO:120, SEQ ID NO:126, and SEQ ID NO:132. In some embodiments, the CD28 binding domain provided herein comprises a VH having an amino acid sequence of SEQ ID NO:31, and a VL having an amino acid sequence of SEQ ID NO:32. In some embodiments, the CD28 binding domain provided herein comprises a VH having an amino acid sequence of SEQ ID NO:65, and a VL having an amino acid sequence of SEQ ID NO:66. In some embodiments, the CD28 binding domain provided herein comprises a VH having an amino acid sequence of SEQ ID NO:99, and a VL having an amino acid sequence of SEQ ID NO:100. In some embodiments, the CD28 binding domain provided herein comprises a VH having an amino acid sequence of SEQ ID NO:133, and a VL having an amino acid sequence of SEQ ID NO:134.

In some embodiments, the antibody specifically binds CD28. In other embodiments, the CD28 is present on the surface of a T cell.

In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In certain embodiments, provided is a CD28 antibody that is an intact antibody. In other embodiments, provided is a CD28 antibody is an antigen binding fragment of the CD28 antibody. In some embodiments, the antigen binding fragment of the CD28 antibody is a functional fragment.

In some embodiments, the antigen binding fragment is a diabody. In some embodiments, the antigen binding fragment is a Fab. In some embodiments, the antigen binding fragment is a Fab'. In some embodiments, the antigen binding fragment is a F(ab')2. In some embodiments, the antigen binding fragment is a Fv fragment. In some embodiments, the antigen binding fragment is a disulfide stabilized Fv fragment (dsFv). In some embodiments, the antigen binding fragment is a $(dsFv)_2$. In some embodiments, the antigen binding fragment is a bispecific dsFv (dsFv-dsFv'). In some embodiments, the antigen binding fragment is a disulfide stabilized diabody (ds diabody). In some embodiments, the antigen binding fragment is a single-chain antibody molecule (scFv). In some embodiments, the antigen binding fragment is a single domain antibody (sdAb). In some embodiments, the antigen binding fragment is an scFv dimer (bivalent diabody). In some embodiments, the antigen binding fragment is a multispecific antibody formed from a portion of an antibody comprising one or more CDRs. In some embodiments, the antigen binding fragment is a camelized single domain antibody. In some embodiments, the antigen binding fragment is a nanobody. In some embodiments, the antigen binding fragment is a domain antibody. In some embodiments, the antigen binding fragment is a bivalent domain antibody. In some embodiments, the antigen binding fragment is an antibody fragment that binds to an antigen but does not comprise a complete antibody structure.

In specific embodiments, the CD28 antibody comprises a VH region and a VL region. In some embodiments, the CD28 antibody is a single chain antibody. In some embodiments, the CD28 antibody is a single domain antibody. In some embodiments, the CD28 antibody is a nanobody. In certain embodiments, the CD28 antibody is a VHH antibody. In certain embodiments, the CD28 antibody is a llama antibody. In some embodiments, the CD28 antibody is not a single chain antibody. In some embodiments, the CD28 antibody is not a single domain antibody. In some embodiments, the CD28 antibody is not a nanobody. In certain embodiments, the CD28 antibody is not a VHH antibody. In certain embodiments, the CD28 antibody is not a llama antibody. In some embodiments, the CD28 antibody is a multispecific antibody. In other embodiments, the CD28 is a bispecific antibody. In certain embodiments, the multispecific antibody comprises an antigen binding fragment of a CD28 antibody provided herein. In other embodiments, the bispecific antibody comprises an antigen binding fragment of a CD28 antibody provided herein. In some embodiments, the CD28 antibody is an agonistic antibody. In certain embodiments, the CD28 antibody activates T cells. In other embodiments, the CD28 antibody is an antagonistic antibody. In certain embodiments, the CD28 antibody inactivates T cells. In some embodiments, the CD28 antibody blocks activation of T cells. In some embodiments, the CD28 antibody modulates the activity of T cells. In some embodiments, the CD28 antibody neither activates or inactivates the activity of T cells. In specific embodiments, the T cells are human T cells.

In some embodiments, the VH CDR1, VH CDR2, VH CDR3, VL CDR1, VL CDR2, and VL CDR3 sequences are according to the Kabat numbering system. In some embodiments, the VH CDR1, VH CDR2, VH CDR3, VL CDR1, VL CDR2, and VL CDR3 sequences are according to the Chothia numbering system. In some embodiments, the VH CDR1, VH CDR2, VH CDR3, VL CDR1, VL CDR2, and VL CDR3 sequences are according to the Exemplary numbering system. In some embodiments, the VH CDR1, VH CDR2, VH CDR3, VL CDR1, VL CDR2, and VL CDR3 sequences are according to the Contact numbering system. In some embodiments, the VH CDR1, VH CDR2, VH CDR3, VL CDR1, VL CDR2, and VL CDR3 sequences are according to the IMGT numbering system. In some embodiments, the VH CDR1, VH CDR2, VH CDR3, VL CDR1, VL CDR2, and VL CDR3 sequences are according to the AbM numbering system. Exemplary sets of 6 CDRs (VH CDR1-3 and VL CDR1-3) of certain antibody embodiments are provided herein. Other sets of CDRs are contemplated and within the scope of the antibody embodiments provided herein.

In one aspect, provided herein is an antibody that binds CD28, comprising a VH comprising a VH CDR1, a VH CDR2, and a VH CDR3 having an amino acid sequence of a VH CDR1, a VH CDR2, and a VH CDR3, respectively, of SEQ ID NO:31. In one aspect, provided herein is an antibody that binds CD28, comprising a VL comprising a VL CDR1, a VL CDR2, and a VL CDR3 having an amino acid sequence of a VL CDR1, a VL CDR2, and a VL CDR3, respectively, of SEQ ID NO:32. In one aspect, provided herein is an antibody that binds CD28, comprising: (i) a VH comprising a VH CDR1, a VH CDR2, and a VH CDR3 having an amino acid sequence of a VH CDR1, a VH CDR2, and a VH CDR3, respectively, of SEQ ID NO:31; and (ii) a VL comprising a VL CDR1, a VL CDR2, and a VL CDR3 having an amino acid sequence of a VL CDR1, a VL CDR2, and a VL CDR3, respectively, of SEQ ID NO:32. In one aspect, provided herein is an antibody that binds CD28, comprising: (i) a VH comprising a VH CDR1, a VH CDR2, and a VH CDR3 having an amino acid sequence of SEQ ID NOs:1, 2, and 3, respectively, and (ii) a VL comprising a VL CDR1, VL CDR2, and VL CDR3 having an amino acid sequence of SEQ ID NOs:4, 5, and 6, respectively. In one aspect, provided herein is an antibody that binds CD28, comprising: (i) a VH comprising a VH CDR1, a VH CDR2, and a VH CDR3 having an amino acid sequence of SEQ ID NOs:7, 8, and 9, respectively, and (ii) a VL comprising a VL CDR1, VL CDR2, and VL CDR3 having an amino acid sequence of SEQ ID NOs:10, 11, and 12, respectively. In one aspect, provided herein is an antibody that binds CD28, comprising: (i) a VH comprising a VH CDR1, a VH CDR2, and a VH CDR3 having an amino acid sequence of SEQ ID NOs:13, 14, and 15, respectively, and (ii) a VL comprising a VL CDR1, VL CDR2, and VL CDR3 having an amino acid sequence of SEQ ID NOs:16, 17, and 18, respectively. In one aspect, provided herein is an antibody that binds CD28, comprising: (i) a VH comprising a VH CDR1, a VH CDR2, and a VH CDR3 having an amino acid sequence of SEQ ID NOs:19, 20, and 21, respectively, and (ii) a VL comprising a VL CDR1, VL CDR2, and VL CDR3 having an amino acid sequence of SEQ ID NOs:22, 23, and 24, respectively. In one aspect, provided herein is an antibody that binds CD28, comprising: (i) a VH comprising a VH CDR1, a VH CDR2, and a VH CDR3 having an amino acid sequence of SEQ ID NOs:25, 26, and 27, respectively, and (ii) a VL comprising a VL CDR1, VL CDR2, and VL CDR3 having an amino acid sequence of SEQ ID NOs:28, 29, and 30, respectively. In one aspect, provided herein is an antibody that binds CD28, comprising a VH having an amino acid sequence of SEQ ID NO:31. In one aspect, provided herein is an antibody that binds CD28, comprising a VL having an amino acid sequence of SEQ ID NO:32. In one aspect, provided herein is an antibody that binds CD28, comprising a VH having an amino acid sequence of SEQ ID NO:31, and a VL having an amino acid sequence of SEQ ID NO:32. In one aspect, provided herein is an antibody that binds CD28, comprising a heavy chain having an amino acid sequence of SEQ ID NO:33. In one aspect, provided herein is an antibody that binds CD28, comprising a light chain having an amino acid sequence of SEQ ID NO:34. In one aspect, provided herein is an antibody that binds CD28, comprising a heavy chain having an amino acid sequence of SEQ ID NO:33, and a light chain having an amino acid sequence of SEQ ID NO:34. In one aspect, provided herein is an antibody that binds CD28, comprising a VH having an amino acid sequence having at least 95% identity to an amino acid sequence of SEQ ID NO:31. In one aspect, provided herein is an antibody that binds CD28, comprising a VL having an amino acid sequence having at least 95% identity to an amino acid sequence of SEQ ID NO:32. In one aspect, provided herein is an antibody that binds CD28, comprising a VH having an amino acid sequence having at least 95% identity to an amino acid sequence of SEQ ID NO:31, and a VL having an amino acid sequence having at least 95% identity to an amino acid sequence of SEQ ID NO:32. In one aspect, provided herein is an antibody that binds CD28, comprising a heavy chain having an amino acid sequence having at least 95% identity to an amino acid sequence of SEQ ID NO:33. In one aspect, provided herein is an antibody that binds CD28, comprising a light chain having an amino acid sequence having at least 95% identity to an amino acid sequence of SEQ ID NO:34. In one aspect, provided herein is an antibody that binds CD28, comprising a heavy chain having an amino acid sequence having at least 95% identity to an amino acid sequence of SEQ ID NO:33, and a light chain having an amino acid sequence having at least 95% identity to an amino acid sequence of SEQ ID NO:34.

In one aspect, provided herein is an antibody that binds CD28, comprising a VH comprising a VH CDR1, a VH CDR2, and a VH CDR3 having an amino acid sequence of a VH CDR1, a VH CDR2, and a VH CDR3, respectively, of SEQ ID NO:65. In one aspect, provided herein is an antibody that binds CD28, comprising a VL comprising a VL CDR1, a VL CDR2, and a VL CDR3 having an amino acid sequence of a VL CDR1, a VL CDR2, and a VL CDR3, respectively, of SEQ ID NO:66. In one aspect, provided herein is an antibody that binds CD28, comprising: (i) a VH comprising a VH CDR1, a VH CDR2, and a VH CDR3 having an amino acid sequence of a VH CDR1, a VH CDR2, and a VH CDR3, respectively, of SEQ ID NO:65; and (ii) a VL comprising a VL CDR1, a VL CDR2, and a VL CDR3 having an amino acid sequence of a VL CDR1, a VL CDR2, and a VL CDR3, respectively, of SEQ ID NO:66. In one aspect, provided herein is an antibody that binds CD28, comprising: (i) a VH comprising a VH CDR1, a VH CDR2, and a VH CDR3 having an amino acid sequence of SEQ ID NOs:35, 36, and 37, respectively, and (ii) a VL comprising a VL CDR1, VL CDR2, and VL CDR3 having an amino acid sequence of SEQ ID NOs:38, 39, and 40, respectively. In one aspect, provided herein is an antibody that binds CD28, comprising: (i) a VH comprising a VH CDR1, a VH CDR2, and a VH CDR3 having an amino acid sequence of SEQ ID NOs:41, 42, and 43, respectively, and (ii) a VL comprising a VL CDR1, VL CDR2, and VL CDR3 having an amino acid sequence of SEQ ID NOs:44, 45, and 46, respectively. In one aspect, provided herein is an antibody that binds CD28, comprising: (i) a VH comprising a VH CDR1, a VH CDR2, and a VH CDR3 having an amino acid sequence of SEQ ID NOs:47, 48, and 49, respectively, and (ii) a VL comprising a VL CDR1, VL CDR2, and VL CDR3 having an amino acid sequence of SEQ ID NOs:50, 51, and 52, respectively. In one aspect, provided herein is an antibody that binds CD28, comprising: (i) a VH comprising a VH CDR1, a VH CDR2, and a VH CDR3 having an amino acid sequence of SEQ ID NOs:53, 54, and 55, respectively, and (ii) a VL comprising a VL CDR1, VL CDR2, and VL CDR3 having an amino acid sequence of SEQ ID NOs:56, 57, and 58, respectively. In one aspect, provided herein is an antibody that binds CD28, comprising: (i) a VH comprising a VH CDR1, a VH CDR2, and a VH CDR3 having an amino acid sequence of SEQ ID NOs:59, 60, and 61, respectively, and (ii) a VL comprising a VL CDR1, VL CDR2, and VL CDR3 having an amino acid sequence of SEQ ID NOs:62, 63, and 64, respectively. In one aspect, provided herein is an antibody that binds CD28, comprising a VH having an amino acid sequence of SEQ ID NO:65. In one aspect, provided herein is an antibody that binds CD28, comprising a VL having an amino acid sequence of SEQ ID NO:66. In one aspect, provided herein is an antibody that binds CD28, comprising a VH having an amino acid sequence of SEQ ID NO:65, and a VL having an amino acid sequence of SEQ ID NO:66. In one aspect, provided herein is an antibody that binds CD28, comprising a heavy chain having an amino acid sequence of SEQ ID NO:67. In one aspect, provided herein is an antibody that binds CD28, comprising a light chain having an amino acid sequence of SEQ ID NO:68. In one aspect, provided herein is an antibody that binds CD28, comprising a heavy chain having an amino acid sequence of SEQ ID NO:67, and a light chain having an amino acid sequence of SEQ ID NO:68. In one aspect, provided herein is an antibody that binds CD28, comprising a VH having an amino acid sequence having at least 95% identity to an amino acid sequence of SEQ ID NO:65. In one aspect, provided herein is an antibody that binds CD28, comprising a VL having an amino acid sequence having at least 95% identity to an amino acid sequence of SEQ ID NO:66. In one aspect, provided herein is an antibody that binds CD28, comprising a VH having an amino acid sequence having at least 95% identity to an amino acid sequence of SEQ ID NO:65, and a VL having an amino acid sequence having at least 95% identity to an amino acid sequence of SEQ ID NO:66. In one aspect, provided herein is an antibody that binds CD28, comprising a heavy chain having an amino acid sequence having at least 95% identity to an amino acid sequence of SEQ ID NO:67. In one aspect, provided herein is an antibody that binds CD28, comprising a light chain having an amino acid sequence having at least 95% identity to an amino acid sequence of SEQ ID NO:68. In one aspect, provided herein is an antibody that binds CD28, comprising a heavy chain having an amino acid sequence having at least 95% identity to an amino acid sequence of SEQ ID NO:67, and a light chain having an amino acid sequence having at least 95% identity to an amino acid sequence of SEQ ID NO:68.

In one aspect, provided herein is an antibody that binds CD28, comprising a VH comprising a VH CDR1, a VH CDR2, and a VH CDR3 having an amino acid sequence of a VH CDR1, a VH CDR2, and a VH CDR3, respectively, of SEQ ID NO:99. In one aspect, provided herein is an antibody that binds CD28, comprising a VL comprising a VL CDR1, a VL CDR2, and a VL CDR3 having an amino acid sequence of a VL CDR1, a VL CDR2, and a VL CDR3, respectively, of SEQ ID NO:100. In one aspect, provided herein is an antibody that binds CD28, comprising: (i) a VH comprising a VH CDR1, a VH CDR2, and a VH CDR3 having an amino acid sequence of a VH CDR1, a VH CDR2, and a VH CDR3, respectively, of SEQ ID NO:99; and (ii) a VL comprising a VL CDR1, a VL CDR2, and a VL CDR3 having an amino acid sequence of a VL CDR1, a VL CDR2, and a VL CDR3, respectively, of SEQ ID NO:100. In one aspect, provided herein is an antibody that binds CD28, comprising: (i) a VH comprising a VH CDR1, a VH CDR2, and a VH CDR3 having an amino acid sequence of SEQ ID NOs:69, 70, and 71, respectively, and (ii) a VL comprising a VL CDR1, VL CDR2, and VL CDR3 having an amino acid sequence of SEQ ID NOs:72, 73, and 74, respectively. In one aspect, provided herein is an antibody that binds CD28, comprising: (i) a VH comprising a VH CDR1, a VH CDR2, and a VH CDR3 having an amino acid sequence of SEQ ID NOs:75, 76, and 77, respectively, and (ii) a VL comprising a VL CDR1, VL CDR2, and VL CDR3 having an amino acid sequence of SEQ ID NOs:78, 79, and 80, respectively. In one aspect, provided herein is an antibody that binds CD28, comprising: (i) a VH comprising a VH CDR1, a VH CDR2, and a VH CDR3 having an amino acid sequence of SEQ ID NOs:81, 82, and 83, respectively, and (ii) a VL comprising a VL CDR1, VL CDR2, and VL CDR3 having an amino acid sequence of SEQ ID NOs:84, 85, and 86, respectively. In one aspect, provided herein is an antibody that binds CD28, comprising: (i) a VH comprising a VH CDR1, a VH CDR2, and a VH CDR3 having an amino acid sequence of SEQ ID NOs:87, 88, and 89, respectively, and (ii) a VL comprising a VL CDR1, VL CDR2, and VL CDR3 having an amino acid sequence of SEQ ID NOs:90, 91, and 92, respectively. In one aspect, provided herein is an antibody that binds CD28, comprising: (i) a VH comprising a VH CDR1, a VH CDR2, and a VH CDR3 having an amino acid sequence of SEQ ID NOs:93, 94, and 95, respectively, and (ii) a VL comprising a VL CDR1, VL CDR2, and VL CDR3 having an amino acid sequence of SEQ ID NOs:96, 97, and 98, respectively. In one aspect, provided herein is an antibody that binds CD28, comprising a VH having an amino acid sequence of SEQ ID NO:99. In one aspect, provided herein is an antibody that binds CD28, comprising a VL having an amino acid sequence of SEQ ID NO:100. In one aspect, provided herein is an antibody that binds CD28, comprising a VH having an amino acid sequence of SEQ ID NO:99, and a VL having an amino acid sequence of SEQ ID NO:100. In one aspect, provided herein is an antibody that binds CD28, comprising a heavy chain having an amino acid sequence of SEQ ID NO:101. In one aspect, provided herein is an antibody that binds CD28, comprising a light chain having an amino acid sequence of SEQ ID NO:102. In one aspect, provided herein is an antibody that binds CD28, comprising a heavy chain having an amino acid sequence of SEQ ID NO:101, and a light chain having an amino acid sequence of SEQ ID NO:102. In one aspect, provided herein is an antibody that binds CD28, comprising a VH having an amino acid sequence having at least 95% identity to an amino acid sequence of SEQ ID NO:99. In one aspect, provided herein is an antibody that binds CD28, comprising a VL having an amino acid sequence having at least 95% identity to an amino acid sequence of SEQ ID NO:100. In one aspect, provided herein is an antibody that binds CD28, comprising a VH having an amino acid sequence having at least 95% identity to an amino acid sequence of SEQ ID NO:99, and a VL having an amino acid sequence having at least 95% identity to an amino acid sequence of SEQ ID NO:100. In one aspect, provided herein is an antibody that binds CD28, comprising a heavy chain having an amino acid sequence having at least 95% identity to an amino acid sequence of SEQ ID NO:101. In one aspect, provided herein is an antibody that binds CD28, comprising a light chain having an amino acid sequence having at least 95% identity to an amino acid sequence of SEQ ID NO:102. In one aspect, provided herein is an antibody that binds CD28, comprising a heavy chain having an amino acid sequence having at least 95% identity to an amino acid sequence of SEQ ID NO:101, and a light chain having an amino acid sequence having at least 95% identity to an amino acid sequence of SEQ ID NO:102.

In one aspect, provided herein is an antibody that binds CD28, comprising a VH comprising a VH CDR1, a VH CDR2, and a VH CDR3 having an amino acid sequence of a VH CDR1, a VH CDR2, and a VH CDR3, respectively, of SEQ ID NO:133. In one aspect, provided herein is an antibody that binds CD28, comprising a VL comprising a VL CDR1, a VL CDR2, and a VL CDR3 having an amino acid sequence of a VL CDR1, a VL CDR2, and a VL CDR3, respectively, of SEQ ID NO:134. In one aspect, provided herein is an antibody that binds CD28, comprising: (i) a VH comprising a VH CDR1, a VH CDR2, and a VH CDR3 having an amino acid sequence of a VH CDR1, a VH CDR2, and a VH CDR3, respectively, of SEQ ID NO:133; and (ii) a VL comprising a VL CDR1, a VL CDR2, and a VL CDR3 having an amino acid sequence of a VL CDR1, a VL CDR2, and a VL CDR3, respectively, of SEQ ID NO:134. In one aspect, provided herein is an antibody that binds CD28, comprising: (i) a VH comprising a VH CDR1, a VH CDR2, and a VH CDR3 having an amino acid sequence of SEQ ID NOs:103, 104, and 105, respectively, and (ii) a VL comprising a VL CDR1, VL CDR2, and VL CDR3 having an amino acid sequence of SEQ ID NOs:106, 107, and 108, respectively. In one aspect, provided herein is an antibody that binds CD28, comprising: (i) a VH comprising a VH CDR1, a VH CDR2, and a VH CDR3 having an amino acid sequence of SEQ ID NOs:109, 110, and 111, respectively, and (ii) a VL comprising a VL CDR1, VL CDR2, and VL CDR3 having an amino acid sequence of SEQ ID NOs:112, 113, and 114, respectively. In one aspect, provided herein is an antibody that binds CD28, comprising: (i) a VH comprising a VH CDR1, a VH CDR2, and a VH CDR3 having an amino acid sequence of SEQ ID NOs:115, 116, and 117, respectively, and (ii) a VL comprising a VL CDR1, VL CDR2, and VL CDR3 having an amino acid sequence of SEQ ID NOs:118, 119, and 120, respectively. In one aspect, provided herein is an antibody that binds CD28, comprising: (i) a VH comprising a VH CDR1, a VH CDR2, and a VH CDR3 having an amino acid sequence of SEQ ID NOs:121, 122, and 123, respectively, and (ii) a VL comprising a VL CDR1, VL CDR2, and VL CDR3 having an amino acid sequence of SEQ ID NOs:124, 125, and 126, respectively. In one aspect, provided herein is an antibody that binds CD28, comprising: (i) a VH comprising a VH CDR1, a VH CDR2, and a VH CDR3 having an amino acid sequence of SEQ ID NOs:127, 128, and 129, respectively, and (ii) a VL comprising a VL CDR1, VL CDR2, and VL CDR3 having an amino acid sequence of SEQ ID NOs:130, 131, and 132, respectively. In one aspect, provided herein is an antibody that binds CD28, comprising a VH having an amino acid sequence of SEQ ID NO:133. In one aspect, provided herein is an antibody that binds CD28, comprising a VL having an amino acid sequence of SEQ ID NO:134. In one aspect, provided herein is an antibody that binds CD28, comprising a VH having an amino acid sequence of SEQ ID NO:133, and a VL having an amino acid sequence of SEQ ID NO:134. In one aspect, provided herein is an antibody that binds CD28, comprising a heavy chain having an amino acid sequence of SEQ ID NO:135. In one aspect, provided herein is an antibody that binds CD28, comprising a light chain having an amino acid sequence of SEQ ID NO:136. In one aspect, provided herein is an antibody that binds CD28, comprising a heavy chain having an amino acid sequence of SEQ ID NO:135, and a light chain having an amino acid sequence of SEQ ID NO:136. In one aspect, provided herein is an antibody that binds CD28, comprising a VH having an amino acid sequence having at least 95% identity to an amino acid sequence of SEQ ID NO:133. In one aspect, provided herein is an antibody that binds CD28, comprising a VL having an amino acid sequence having at least 95% identity to an amino acid sequence of SEQ ID NO:134. In one aspect, provided herein is an antibody that binds CD28, comprising a VH having an amino acid sequence having at least 95% identity to an amino acid sequence of SEQ ID NO:133, and a VL having an amino acid sequence having at least 95% identity to an amino acid sequence of SEQ ID NO:134. In one aspect, provided herein is an antibody that binds CD28, comprising a heavy chain having an amino acid sequence having at least 95% identity to an amino acid sequence of SEQ ID NO:135. In one aspect, provided herein is an antibody that binds CD28, comprising a light chain having an amino acid sequence having at least 95% identity to an amino acid sequence of SEQ ID NO:136. In one aspect, provided herein is an antibody that binds CD28, comprising a heavy chain having an amino acid sequence having at least 95% identity to an amino acid sequence of SEQ ID NO:135, and a light chain having an amino acid sequence having at least 95% identity to an amino acid sequence of SEQ ID NO:136.

In another aspect, provided herein is an antibody that competes for binding to CD28 with any of the CD28 antibodies described herein. In another aspect, provided herein is an antibody that binds to the same epitope as any of the CD28 antibodies described herein. In another aspect, provided is a CD28 antibody that binds an epitope on CD28 that overlaps with the epitope on CD28 bound by a CD28 antibody described herein.

In one aspect, provided is an antibody that competes for binding to CD28 with a CD28 reference antibody. In another aspect, provided is a CD28 antibody that binds to the same CD28 epitope as a CD28 reference antibody. In another aspect, provided is a CD28 antibody that binds an epitope on CD28 that overlaps with the epitope on CD28 bound by a CD28 reference antibody.

In one embodiment, the CD28 reference antibody comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:31; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:32. In one embodiment, the CD28 reference antibody comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:65; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:66. In one embodiment, the CD28 reference antibody comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:99; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:100. In one embodiment, the CD28 reference antibody comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:133; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:134.

In another aspect, provided herein is a multispecific antibody that binds CD28. In some embodiments, the multispecific antibody is a bispecific antibody. In some embodiments, the multispecific antibody is a trispecific antibody. In some embodiments, the multispecific antibody is a quadraspecific antibody. In one embodiment, the multispecific CD28 antibody comprises: (a) a first binding domain that binds CD28, and (b) a second binding domain that binds to a second target. In one embodiment, the multispecific CD28 antibody comprises: (a) a first binding domain that binds CD28, and (b) a second binding domain that binds to a second target, and (c) a third binding domain that binds to a third target. In one embodiment, the multispecific CD28 antibody comprises: (a) a first binding domain that binds CD28, and (b) a second binding domain that binds to a second target, (c) a third binding domain that binds to a third target, and (d) a fourth binding domain that binds to a fourth target.

In another aspect, provided herein is a bispecific antibody comprising: (a) a first binding domain that binds to CD28, and (b) a second binding domain that binds to a second target that is not CD28. In another aspect, provided herein is a bispecific antibody comprising: (a) a first binding domain that binds to CD28, and (b) a second binding domain that binds to a second target that binds to a second target that is not CD28.

In one embodiment, the first binding domain that binds CD28 comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:31; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:32. In one embodiment, the first binding domain that binds CD28 comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:65; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:66. In one embodiment, the first binding domain that binds CD28 comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:99; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:100. In one embodiment, the first binding domain that binds CD28 comprises: (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:133; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:134.

In some embodiments, the VH CDR1, VH CDR2, VH CDR3, VL CDR1, VL CDR2, and VL CDR3 amino acid sequences of the first binding domain that binds CD28 are according to the Kabat numbering system. In some embodiments, the VH CDR1, VH CDR2, VH CDR3, VL CDR1, VL CDR2, and VL CDR3 amino acid sequences of the first binding domain that binds CD28 are according to the Chothia numbering system. In some embodiments, the VH CDR1, VH CDR2, VH CDR3, VL CDR1, VL CDR2, and VL CDR3 amino acid sequences of the first binding domain that binds CD28 are according to the AbM numbering system. In some embodiments, the VH CDR1, VH CDR2, VH CDR3, VL CDR1, VL CDR2, and VL CDR3 amino acid sequences of the first binding domain that binds CD28 are according to the Contact numbering system. In some embodiments, the VH CDR1, VH CDR2, VH CDR3, VL CDR1, VL CDR2, and VL CDR3 amino acid sequences of the first binding domain that binds CD28 are according to the IMGT numbering system.

In some embodiments, the first binding domain binds a CD28 antigen. In some embodiments, the first binding domain binds a CD28 epitope. In some embodiments, the first binding domain specifically binds to CD28. In some embodiments, the VH CDR1, VH CDR2, VH CDR3, VL CDR1, VL CDR2 and VL CDR3 of the first binding domain form a binding site for an antigen of the CD28. In some embodiments, the VH CDR1, VH CDR2, VH CDR3, VL CDR1, VL CDR2 and VL CDR3 of the first binding domain form a binding site for an epitope of the CD28. In some embodiments, the CD28 is present on the surface of a T cell.

In some embodiments of the multispecific CD28 antibodies provided herein, the second target is not a CD28 antigen. In some embodiments of the multispecific CD28 antibodies provided herein, the third target is not a CD28 antigen. In some embodiments of the multispecific CD28 antibodies provided herein, the fourth target is not a CD28 antigen. In some embodiments of the multispecific CD28 antibodies provided herein, the second target is not a CD28 antigen, and the third target is not a CD28 antigen. In some embodiments of the multispecific CD28 antibodies provided herein, the second target is not a CD28 antigen, and the fourth target is not a CD28 antigen. In some embodiments of the multispecific CD28 antibodies provided herein, the third target is not a CD28 antigen, and the fourth target is not a CD28 antigen. In some embodiments of the multispecific CD28 antibodies provided herein, the second target is not a CD28 antigen, the third target is not a CD28 antigen, and the fourth target is not a CD28 antigen. In some embodiments of the multispecific CD28 antibodies provided herein, the second target is not a CD28 epitope. In some embodiments of the multispecific CD28 antibodies provided herein, the third target is not a CD28 epitope. In some embodiments of the multispecific CD28 antibodies provided herein, the fourth target is not a CD28 epitope. In some embodiments of the multispecific CD28 antibodies provided herein, the second target is not a CD28 epitope, and the third target is not a CD28 epitope. In some embodiments of the multispecific CD28 antibodies provided herein, the second target is not a CD28 epitope, and the fourth target is not a CD28 epitope. In some embodiments of the multispecific CD28 antibodies provided herein, the third target is not a CD28 epitope, and the fourth target is not a CD28 epitope. In some embodiments of the multispecific CD28 antibodies provided herein, the second target is not a CD28 epitope, the third target is not a CD28 epitope, and the fourth target is not a CD28 epitope.

In some embodiments of the multispecific CD28 antibodies provided herein, the second target is a second target that is not CD28.

In specific embodiments, provided is a multispecific antibody comprising a CD28 antibody provided herein in a knob-in-hole format. In specific embodiments, provided is a bispecific antibody comprising a CD28 antibody provided herein in a knob-in-hole format. In specific embodiments, provided is a trispecific antibody comprising a CD28 antibody provided herein in a knob-in-hole format. In specific embodiments, provided is a quadraspecific antibody comprising a CD28 antibody provided herein in a knob-in-hole format. Other specificities can be added to an antibody in knob-in-hole format using methods well known in the art (e.g., adding an scFv to the N-terminus or C-terminus). In addition, other formats and methods of making multispecific antibodies are also known in the art and contemplated. In some embodiments, a CD28 antibody provided herein is comprised in a bispecific antibody. In some embodiments, a CD28 antibody provided herein is comprised in a trispecific antibody. In some embodiments, a CD28 antibody provided herein is comprised in a quadraspecific antibody. In some embodiments, a CD28 bispecific antibody provided herein is comprised in a multispecific antibody.

In certain embodiments, a multispecific antibody provided herein comprises a first binding domain comprising a CD28 antibody provided herein that binds to a first CD28 epitope, and a second binding domain that binds to a second epitope, wherein the first CD28 epitope and the second epitope are not the same. In certain embodiments, a bispecific antibody provided herein comprises a first binding domain comprising a CD28 antibody provided herein that binds to a first CD28 epitope, and a second binding domain that binds to a second epitope, wherein the first CD28 epitope and the second epitope are not the same. In certain embodiments, a trispecific antibody provided herein comprises a first binding domain comprising a CD28 antibody provided herein that binds to a first CD28 epitope, a second binding domain that binds to a second epitope, and a third binding domain that binds to a third epitope, wherein the first CD28 epitope, the second epitope, and the third epitope are not the same. In certain embodiments, a quadraspecific antibody provided herein comprises a first binding domain comprising a CD28 antibody provided herein that binds to a first CD28 epitope, a second binding domain that binds to a second epitope, a third binding domain that binds to a third epitope, and a fourth binding domain that binds to a fourth epitope, wherein the first CD28 epitope, the second epitope, the third epitope, and the fourth epitope are not the same. In certain embodiments, a multispecific antibody provided herein comprises a first binding domain comprising a CD28 antibody provided herein that binds to a first CD28 antigen, and a second binding domain that binds to a second antigen, wherein the first CD28 antigen and the second antigen are not the same. In certain embodiments, a bispecific antibody provided herein comprises a first binding domain comprising a CD28 antibody provided herein that binds to a first CD28 antigen, and a second binding domain that binds to a second antigen, wherein the first CD28 antigen and the second antigen are not the same. In certain embodiments, a trispecific antibody provided herein comprises a first binding domain comprising a CD28 antibody provided herein that binds to a first CD28 antigen, a second binding domain that binds to a second antigen, and a third binding domain that binds to a third antigen, wherein the first CD28 antigen, the second antigen, and the third antigen are not the same. In certain embodiments, a quadraspecific antibody provided herein comprises a first binding domain comprising a CD28 antibody provided herein that binds to a first CD28 antigen, a second binding domain that binds to a second antigen, a third binding domain that binds to a third antigen, and a fourth binding domain that binds to a fourth antigen, wherein the first CD28 antigen, the second antigen, the third antigen, and the fourth antigen are not the same. In a specific embodiment, a CD28 antibody, or antigen binding fragment thereof, provided herein specifically binds to CD28.

In some embodiments, the multispecific antibody comprises heavy chain variable regions and light chain variable region. In some embodiments, the first binding domain comprises a heavy chain variable region and a light chain variable region. In some embodiments, the second binding domain comprises a heavy chain variable region and a light chain variable region. In some embodiments, the first binding domain comprises a heavy chain variable region and a light chain variable region, and the second binding domain comprises a heavy chain variable region and a light chain variable region. In a some embodiments, the CD8 antibody is not a single domain antibody or nanobody. In some embodiments, the third binding domain comprises a heavy chain variable region and a light chain variable region. In some embodiments, the fourth binding domain comprises a heavy chain variable region and a light chain variable region.

In certain embodiments, the CD28 multispecific antibodies or antigen binding fragments thereof bind to a first epitope located on CD28 and a second epitope of a second target antigen. In some embodiments, provided herein is a multispecific antibody comprising: (a) a first binding domain that binds to a CD28 antigen, and (b) a second binding domain that binds to a second target antigen. In some embodiments, provided herein is a multispecific antibody comprising: (a) a first binding domain that specifically binds to a CD28 antigen, and (b) a second binding domain that specifically binds to a second target antigen. In some embodiments, provided herein is a multispecific antibody comprising: (a) a first binding domain that binds to a first epitope on a CD28 antigen, and (b) a second binding domain that binds to a second epitope on a second target antigen. In some embodiments, provided herein is a multispecific antibody comprising: (a) a first binding domain that specifically binds to a first epitope on a CD28 antigen, and (b) a second binding domain that specifically binds to a second epitope on a second target antigen.

In specific embodiments, the CD28 antigen is on the surface of a T cell. In certain embodiments, the second target antigen is not CD28. The binding of the CD28 multispecific antibody to CD28 present on the surface of the T cell, and the binding of the second target antigen present on the surface of the second target cell can, for example, result in the killing of the second target cell. In other embodiment, the binding of the CD28 multispecific antibody to CD28 present on the surface of the T cell, and the binding of a second target antigen can, for example, result in the activation of the T cell.

In some embodiments, the CD28 antibody is a multispecific antibody. In some embodiments, the CD28 multispecific antibody comprises a first binding domain that binds to CD28. In some embodiments, the CD28 multispecific antibody comprises a first binding domain that binds to CD28, and a second binding domain that binds to a second target this is not CD28.

In some embodiments, the CD28 multispecific antibody comprises a first binding domain that binds to CD28, and a second binding domain that binds to a second target, wherein the second target is Vβ17. In some embodiments, the CD28×VB17 multispecific antibody further comprises a third binding domain that binds to a third target. In a specific embodiment, the third target is not CD28 or Vβ17. In some embodiments, the CD28 multispecific antibody comprises a first binding domain that binds to CD28, and a second binding domain that binds to a second target, wherein the second target is BCMA. In some embodiments, the CD28×BCMA multispecific antibody further comprises a third binding domain that binds to a third target. In a specific embodiment, the third target is not CD28 or BCMA. In some embodiments, the CD28 multispecific antibody comprises a first binding domain that binds to CD28; a second binding domain that binds to a second target, wherein the second target is Vβ17; and a third binding domain that binds to a third target, wherein the third target is BCMA. In certain embodiments, the binding domain that binds to CD28 is a CD28 antibody provided herein. In certain embodiments, the binding domain that binds to CD28 is a binding fragment of a CD28 antibody provided herein. In certain embodiments, the binding domain that binds to Vβ17 is a Vβ17 antibody provided herein. In certain embodiments, the binding domain that binds to Vβ17 is a binding fragment of a Vβ17 antibody provided herein. In certain embodiments, the binding domain that binds to BCMA is a BCMA antibody provided herein. In certain embodiments, the binding domain that binds to BCMA is a binding fragment of a BCMA antibody provided herein. Amino acid sequences of exemplary BCMA antibodies are provided in the specification and examples. Amino acid sequences of exemplary Vβ17 antibodies are also provided in the specification and examples.

In specific embodiments, the CD28 antigen is on the surface of a T cell. In specific embodiments, the second target antigen is on the surface of a cell. The binding of the CD28 multispecific antibody to CD28 present on the surface of T cells and the second target can, for example, result in the killing of the cell expressing the second target. In other embodiments, the binding of the CD28 multispecific antibody to CD28 present on the surface of T cells can, for example, result in the activation of the T cell.

In some embodiments, a multispecific antibody provided herein is a diabody, a cross-body, or a multispecific antibody obtained via a controlled Fab arm exchange as those described herein.

In some embodiments, the multispecific antibodies include IgG-like molecules with complementary CH3 domains that promote heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody) (EMD Serono), the Biclonic (Merus) and the DuoBody (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (ImClone/Eli Lilly), Ts2Ab (MedImmune/AZ) and BsAb (Zymogenetics), HERCULES (Biogen Idec) and TvAb (Roche).

In some embodiments, Fc fusion molecules can include ScFv/Fc Fusions (Academic Institution), SCORPION (Emergent BioSolutions/Trubion, Zymogenetics/BMS), Dual Affinity Retargeting Technology (Fc-DART) (MacroGenics) and Dual$(ScFv)_2$-Fab (National Research Center for Antibody Medicine—China).

In some embodiments, Fab fusion bispecific antibodies include $F(ab)_2$ (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Full length bispecific antibodies provided herein can be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms can be engineered to favor heterodimerization over homodimerization. The resulting product is a bispecific antibody having two Fab arms or half molecules which each binding a distinct epitope, e.g., an epitope on a first target and an epitope on a second target. Other methods of making multispecific antibodies are known and contemplated.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Publ. No. WO2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob." Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface can be used, as described in US Pat. Publ. No. US2010/0015133; US Pat. Publ. No. US2009/0182127; US Pat. Publ. No. US2010/028637; or US Pat. Publ. No. US2011/0123532. In other strategies, heterodimerization can be promoted by the following substitutions (expressed as modified position in the first CH3 domain of the first heavy chain/modified position in the second CH3 domain of the second heavy chain): L351Y_F405AY407V/T394W, T366I_K392M_T394W/F405A_Y407V, T366L_K392M_T394W/F405A_Y407V, L351Y_Y407A/T366A_K409F, L351Y_Y407A/T366V_K409F_Y407A/T366A_K409F, or T350V_L351Y_F405A_Y407V/T350V_T366L_K392L_T394W as described in U.S. Pat. Publ. No. US2012/0149876 or U.S. Pat. Publ. No. US2013/0195849.

In addition to methods described above, bispecific antibodies provided herein can be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in PCT Pat. Publ. No. WO2011/131746. In the methods, the first monospecific bivalent antibody and the second monospecific bivalent antibody are engineered to have certain substitutions at the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions can optionally be restored to non-reducing conditions. Exemplary reducing agents that can be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, preferably a reducing agent selected from the group consisting of: 2-mercaptoethylamine, dithiothreitol and tris (2-carboxyethyl) phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 can be used.

In some embodiments, the CD28 antibody comprises a single chain antibody. In some embodiments, the CD28 antibody comprises a single domain antibody. In certain embodiments, the CD28 antibody comprises a nanobody. In certain embodiments, the CD28 antibody comprises a VHH antibody. In certain embodiments, the CD28 antibody comprises a llama antibody. In some embodiments, the CD28 antibody does not comprise a single chain antibody. In some embodiments, the CD28 antibody does not comprise a single domain antibody. In certain embodiments, the CD28 antibody does not comprise a nanobody. In certain embodiments, the CD28 antibody does not comprise a VHH antibody. In certain embodiments, the CD28 antibody does not comprise a llama antibody.

In some embodiments, the CD28 multispecific antibody comprises a single chain antibody. In some embodiments, the CD28 multispecific antibody comprises a single domain antibody. In certain embodiments, the CD28 multispecific antibody comprises a nanobody. In certain embodiments, the CD28 multispecific antibody comprises a VHH antibody. In certain embodiments, the CD28 multispecific antibody comprises a llama antibody. In some embodiments, the CD28 multispecific antibody does not comprise a single chain antibody. In some embodiments, the CD28 multispecific antibody does not comprise a single domain antibody. In certain embodiments, the CD28 multispecific antibody does not comprise a nanobody. In certain embodiments, the CD28 multispecific antibody does not comprise a VHH antibody. In certain embodiments, the CD28 multispecific antibody does not comprise a llama antibody.

According to another particular aspect, provided herein is a CD28 antibody or antigen-binding fragment thereof that induces antibody-dependent cell-mediated cytotoxicity (ADCC). The antibody or antigen-binding fragment thereof can, for example, induce ADCC in vitro.

In certain embodiments, the CD28 antibody induces T cell dependent cytotoxicity of a second cell in vitro with an $EC_{50}$ of less than about 160 pM, when assessed in vitro at an effector to target cell ratio of 1:1.

In some embodiments, CD28 is present on the surface of a T cell. In some embodiments, the CD28 is present on the surface of a T cell, and the second target antigen is on the surface of a second cell. In some embodiments, the second cell is killed when the multispecific antibody binds to the CD28 on the surface of the T cell and the second target antigen on the surface of the second cell. In a specific embodiment, the T cell is a CD8+ T cell.

In some embodiments, the multispecific antibody induces T cell dependent cytotoxicity of the second cell in vitro with an $EC_{50}$ of less than about 500 pM. In some embodiments, the multispecific antibody induces T cell dependent cytotoxicity of the second cell in vitro with an $EC_{50}$ of less than about 300 pM. In some embodiments, the multispecific antibody induces γδ T cell dependent cytotoxicity of the second cell in vitro with an $EC_{50}$ of less than about 160 pM. In some embodiments, the $EC_{50}$ is assessed with a mixture of T effector cells and target cells expressing the second target antigen. In some embodiments, the effector cell to target cell ratio is about 0.01 to 1 to about 5 to 1. In some embodiments, the effector cell to target cell ratio is about 0.1 to 1 to about 2 to 1. In some embodiments, the effector cell to target cell ratio is about 1:1.

In certain embodiments, the $EC_{50}$ is less than about 1000 pM, less than about 900 pM, less than about 800 pM, less than about 700 pM, less than about 600 pM, less than about 500 pM, less than about 400 pM, less than about 300 pM, less than about 200 pM, less than about 190 pM, less than about 180 pM, less than about 170 pM, less than about 160 pM, less than about 150 pM, less than about 140 pM, less than about 130 pM, less than about 120 pM, less than about 110 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM.

In certain embodiments, the effector to target cell ratio can, for example, be 0.01:1, 0.02:1, 0.03:1, 0.04:1, 0.05:1, 0.06:1, 0.07:1, 0.08:1, 0.09:1, 1:1, 2:1, 3:1, 4:1, 5:1, 6:1, 7:1, 8:1, 9:1, or 10:1. In certain embodiments, the concentration of the multispecific antibody is about 0.000005 ng/mL, about 0.00005 ng/mL, about 0.0005, about 0.005 ng/mL, about 0.01 ng/mL, about 0.02 ng/mL, about 0.03 ng/mL, about 0.04 ng/mL, about 0.05 ng/mL, about 0.06 ng/mL, about 0.07 ng/mL, about 0.08 ng/mL, about 0.09 ng/mL, about 0.1 ng/mL, about 0.5 ng/mL, about 1.0 ng/mL, about 10 ng/mL, about 20 ng/mL about, about 30 ng/mL about 40 ng/mL, about 50 ng/mL, about 60 ng/mL, about 70 ng/mL, about 80 ng/mL, about 90 ng/mL, about 100 ng/mL, or about 1000 ng/mL.

In another aspect, provided herein is an antibody that competes for binding to CD28 with any of the CD28 antibodies described herein. In another aspect, provided herein is an antibody that binds to the same epitope as any of the CD28 antibodies described herein. In another aspect, provided is a CD28 antibody that binds an epitope on CD28 that overlaps with the epitope on CD28 bound by a CD28 antibody described herein. In some embodiments, the CD28 antibody comprises a VH CDR1, VH CDR2, and VH CDR3 of a CD28 antibody provided herein. In some embodiments, the CD28 antibody comprises a VL CDR1, VL CDR2, and VL CDR3 of a CD28 antibody provided herein. In some embodiments, the CD28 antibody comprises a VH CDR1, VH CDR2, VH CDR3, a VL CDR1, VL CDR2, and VL CDR3 of a CD28 antibody provided herein. In some embodiments, the CD28 antibody comprises a VH of a CD28 antibody provided herein. In some embodiments, the CD28 antibody comprises a VL of a CD28 antibody provided herein. In some embodiments, the CD28 antibody comprises a VH and a VL of a CD28 antibody provided herein. In some embodiments, the CD28 antibody comprises a VH CDR1, VH CDR2, VH CDR3, a VL CDR1, VL CDR2, and VL CDR3 of a CD28 antibody provided herein. In some embodiments, the VH CDR1, VH CDR2, VH CDR3, VL CDR1, VL CDR2, and VL CDR3 amino acid sequences of the CD28 antibody are according to the Kabat numbering system. In some embodiments, the VH CDR1, VH CDR2, VH CDR3, VL CDR1, VL CDR2, and VL CDR3 amino acid sequences of the CD28 antibody are according to the Chothia numbering system. In some embodiments, the VH CDR1, VH CDR2, VH CDR3, VL CDR1, VL CDR2, and VL CDR3 amino acid sequences of the CD28 antibody are according to the AbM numbering system. In some embodiments, the VH CDR1, VH CDR2, VH CDR3, VL CDR1, VL CDR2, and VL CDR3 amino acid sequences of the CD28 antibody are according to the Contact numbering system. In some embodiments, the VH CDR1, VH CDR2, VH CDR3, VL CDR1, VL CDR2, and VL CDR3 amino acid sequences of the CD28 antibody are according to the IMGT numbering system. In certain embodiments, the CD28 antibody is a multispecific antibody. In some embodiments, the CD28 antibody is a bispecific antibody.

In another aspect, provided is an antibody that competes for binding to CD28 with a CD28 reference antibody. In another aspect, provided is a CD28 antibody that binds to the same CD28 epitope as a CD28 reference antibody. In another aspect, provided is a CD28 antibody that binds an epitope on CD28 that overlaps with the epitope on CD28 bound by a CD28 reference antibody. In some embodiments, the CD28 reference antibody comprises a VH CDR1, VH CDR2, and VH CDR3 of a CD28 reference antibody provided herein. In some embodiments, the CD28 reference antibody comprises a VL CDR1, VL CDR2, and VL CDR3 of a CD28 reference antibody provided herein. In some embodiments, the CD28 reference antibody comprises a VH CDR1, VH CDR2, VH CDR3, a VL CDR1, VL CDR2, and VL CDR3 of a CD28 reference antibody provided herein. In some embodiments, the CD28 reference antibody comprises a VH of a CD28 reference antibody provided herein. In some embodiments, the CD28 reference antibody comprises a VL of a CD28 reference antibody provided herein. In some embodiments, the CD28 reference antibody comprises a VH and a VL of a CD28 reference antibody provided herein. In some embodiments, the CD28 reference antibody comprises a VH CDR1, VH CDR2, VH CDR3, a VL CDR1, VL CDR2, and VL CDR3 of a CD28 reference antibody provided herein. In some embodiments, the VH CDR1, VH CDR2, VH CDR3, VL CDR1, VL CDR2, and VL CDR3 amino acid sequences of the CD28 reference antibody are according to the Kabat numbering system. In some embodiments, the VH CDR1, VH CDR2, VH CDR3, VL CDR1, VL CDR2, and VL CDR3 amino acid sequences of the CD28 reference antibody are according to the Chothia numbering system. In some embodiments, the VH CDR1, VH CDR2, VH CDR3, VL CDR1, VL CDR2, and VL CDR3 amino acid sequences of the CD28 reference antibody are according to the AbM numbering system. In some embodiments, the VH CDR1, VH CDR2, VH CDR3, VL CDR1, VL CDR2, and VL CDR3 amino acid sequences of the CD28 reference antibody are according to the Contact numbering system. In some embodiments, the VH CDR1, VH CDR2, VH CDR3, VL CDR1, VL CDR2, and VL CDR3 amino acid sequences of the CD28 reference antibody are according to the IMGT numbering system. In certain embodiments, the antibody is a multispecific antibody. In some embodiments, the antibody is a bispecific antibody. In certain embodiments, the CD28 reference antibody is a multispecific antibody. In some embodiments, the CD28 reference antibody is a bispecific antibody.

In some embodiments described herein, immune effector properties of the antibodies provided herein can be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. can be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such Abs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α-1,6-fucosyltrasferase (FUT8) gene (Mori et al., Biotechnol Bioeng 88:901-908, 2004), or coexpression of β-1,4-N-acetylglucosaminyltransferase III and golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the antibodies provided herein can also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

In some embodiments, a CD28 antibody provided herein is chimeric. In some embodiments, a CD28 antibody provided herein is human. In some embodiments, a CD28 antibody provided herein is humanized. In certain embodiments, a CD28 antibody provided herein is an isolated CD28 antibody. In some embodiments, a CD28 antigen binding fragment provided herein is chimeric. In some embodiments, a CD28 antigen binding fragment provided herein is human. In some embodiments, a CD28 antigen binding fragment provided herein is humanized. In certain embodiments, a CD28 antigen binding fragment provided herein is an isolated CD28 antigen binding fragment. In some embodiments, a CD28 antibody provided herein is an IgG antibody. In some embodiments, the IgG antibody is an IgG1 antibody. In some embodiments, the IgG antibody is an IgG2 antibody. In some embodiments, the IgG antibody is an IgG3 antibody. In some embodiments, the IgG antibody is an IgG4 antibody. In some embodiments, a CD28 antibody provided herein is multivalent. In some embodiments, the CD28 antibody is capable of binding at least three antigens. In some embodiments, the CD28 antibody is capable of binding at least four antigens. In some embodiments, the CD28 antibody is capable of binding at least five antigens.

In some embodiments, a CD28 multispecific antibody provided herein is chimeric. In some embodiments, a CD28 multispecific antibody provided herein is human. In some embodiments, a CD28 multispecific antibody provided herein is humanized. In certain embodiments, a CD28 multispecific antibody provided herein is an isolated CD28 multispecific antibody. In some embodiments, a CD28 multispecific antibody comprising a CD28 antigen binding fragment provided herein is chimeric. In some embodiments, a CD28 multispecific antibody comprising a CD28 antigen binding fragment provided herein is human. In some embodiments, a CD28 multispecific antibody comprising a CD28 antigen binding fragment provided herein is humanized. In certain embodiments, a CD28 multispecific antibody comprising a CD28 antigen binding fragment provided herein is an isolated CD28 multispecific antibody. In certain embodiments, the CD28 multispecific antibody is a multispecific CD28/Vβ17 antibody. In certain embodiments, the CD28 multispecific antibody is a multispecific CD28/BCMA antibody. In certain embodiments, the CD28 multispecific antibody is a multispecific CD28/Vβ17/BCMA antibody.

In some embodiments of the CD28 multispecific antibodies provided herein, the first binding domain is human. In some embodiments, the second binding domain is human. In some embodiments of the CD28 multispecific antibodies provided herein, both the first binding domain and the second binding domain are human. In some embodiments of the CD28 multispecific antibodies provided herein, the first binding domain is humanized. In some embodiments of the CD28 multispecific antibodies provided herein, the second binding domain is humanized. In some embodiments of the CD28 multispecific antibodies provided herein, both the first binding domain and the second binding domain are humanized. In some embodiments of the CD28 multispecific antibodies provided herein, both the first binding domain is human and the second binding domain is humanized. In some embodiments of the CD28 multispecific antibodies provided herein, both the first binding domain is humanized and the second binding domain is human. In certain embodiments, the CD28 multispecific antibody is a multispecific CD28/Vβ17 antibody. In certain embodiments, the CD28 multispecific antibody is a multispecific CD28/BCMA antibody. In certain embodiments, the CD28 multispecific antibody is a multispecific CD28/Vβ17/BCMA antibody.

In some embodiments, a CD28 multispecific antibody provided herein is multivalent. In some embodiments, the multispecific antibody is capable of binding at least three antigens. In some embodiments, the multispecific antibody is capable of binding at least five antigens. In certain embodiments, the multispecific antibody is a multispecific antibody. In some embodiments, a CD28 multispecific antibody provided herein is an IgG antibody. In some embodiments, the IgG antibody is an IgG1 antibody. In some embodiments, the IgG antibody is an IgG2 antibody. In some embodiments, the IgG antibody is an IgG3 antibody. In some embodiments, the IgG antibody is an IgG4 antibody. In certain embodiments, the CD28 multispecific antibody is a multispecific CD28/Vβ17 antibody. In certain embodiments, the CD28 multispecific antibody is a multispecific CD28/BCMA antibody. In certain embodiments, the CD28 multispecific antibody is a multispecific CD28/Vβ17/BCMA antibody.

In certain embodiments, the antibodies provided herein are part of a multispecific antibody. In some embodiments, the multispecific antibody comprises a first binding domain that binds to a CD28 antigen. In some embodiments, the multispecific antibody comprises a first binding domain that binds to a CD28 antigen and comprises a second binding domain that binds to a second target antigen, as provided herein. In certain embodiments, the multispecific antibody binds to a CD28 antigen, a second target antigen, and one or more additional antigens. In some embodiments of the various antibodies provided herein, the antibody binds to an epitope of a given antigen. In certain embodiments, the multispecific CD28 antibody is a multispecific CD28/Vβ17 antibody, wherein the second target is Vβ17. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is Vβ17 and the third target is BCMA.

Also provided is a nucleic acid encoding an antibody provided herein. In another general aspect, provide is a vector comprising an isolated nucleic acid encoding an antibody provided herein. In another general aspect, provided is a vector comprising an isolated nucleic acid encoding an antibody provided herein. Also provided is a vector comprising a nucleic acid encoding an antibody provided herein. Also provided is a host cell comprising a vector comprising a nucleic acid encoding an antibody provided herein. Also provided is a kit comprising the vector comprising a nucleic acid encoding an antibody provided herein, and packaging for the same. In another general aspect, provided herein is an isolated nucleic acid encoding a monoclonal antibody or antigen-binding fragment thereof provided herein. In certain embodiments, the antibody is a CD28 antibody. In certain embodiments, the antibody is a multispecific CD28 antibody. Also provided is a nucleic acid encoding a bispecific antibody comprising: (a) a first binding domain that binds to CD28, and (b) a second binding domain that binds to a second target that is not CD28, as provided herein.

Also provided is a nucleic acid encoding a multispecific CD28 antibody provided herein. In another general aspect, provide is a vector comprising an isolated nucleic acid encoding a multispecific CD28 antibody provided herein. In another general aspect, provided is a vector comprising an isolated nucleic acid encoding a multispecific CD28 antibody provided herein. Also provided is a vector comprising a nucleic acid encoding a multispecific CD28 antibody provided herein. Also provided is a host cell comprising a vector comprising a nucleic acid encoding a multispecific CD28 antibody provided herein. Also provided is a kit comprising the vector comprising a nucleic acid encoding a multispecific CD28 antibody provided herein, and packaging for the same. Also provided is an isolated nucleic acid encoding a monoclonal antibody provided herein. Also provided is an isolated nucleic acid encoding an antigen binding fragment provided herein. Also provided is a nucleic acid encoding a multispecific antibody comprising: (a) a first binding domain that binds to CD28, and (b) a second binding domain that binds to a second target this is not CD28, as provided herein. In certain embodiments, the multispecific CD28 antibody is a trispecific antibody. In certain embodiments, the multispecific CD28 antibody is a quadraspecific antibody.

It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding antibodies provided herein can be altered without changing the amino acid sequences of the proteins.

Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to certain embodiments. Such techniques are well known to those skilled in the art in view of the present disclosure.

Also provided is a host cell comprising an isolated nucleic acid encoding an antibody provided herein. Also provided is a host cell comprising an isolated nucleic acid encoding an antigen binding fragment provided herein. Any host cell known to those skilled in the art in view of the present disclosure can be used for recombinant expression of antibodies or antigen-binding fragments thereof provided herein. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

Also provided are methods of producing an antibody disclosed herein. The methods comprise culturing a cell comprising a nucleic acid encoding the antibody under conditions to produce an antibody and recovering the antibody from the cell or cell culture (e.g., from the supernatant). Expressed antibodies can be harvested from the cells and purified according to conventional techniques known in the art and as described herein.

Also provided is a method of producing a multispecific antibody disclosed herein. The methods comprise culturing a cell comprising a nucleic acid encoding the multispecific antibody thereof under conditions to produce the multispecific antibody and recovering the multispecific antibody from the cell or cell culture (e.g., from the supernatant). Expressed multispecific antibodies thereof can be harvested from the cells and purified according to conventional techniques known in the art and as described herein.

Pharmaceutical Compositions

In another general aspect, provided is a pharmaceutical composition comprising a CD28 antibody provided herein and a pharmaceutically acceptable carrier. In certain embodiments, the antibody is isolated. Also provided is a method of producing the pharmaceutical composition, comprising combining the antibody with a pharmaceutically acceptable carrier to obtain the pharmaceutical composition.

In another general aspect, provided is a pharmaceutical composition comprising a CD28 multispecific antibody provided herein and a pharmaceutically acceptable carrier. In certain embodiments, the multispecific antibody is isolated. Also provided is a method of producing the pharmaceutical composition, comprising combining the multispecific antibody with a pharmaceutically acceptable carrier to obtain the pharmaceutical composition. In another aspect, provided herein is a pharmaceutical composition comprising a comprising: (a) a first binding domain that binds to CD28, and (b) a second binding domain that binds to a second target, and a pharmaceutically acceptable carrier. Any of the multispecific antibodies provided herein are contemplated in the pharmaceutical compositions. Any of the antibodies provided herein are contemplated in the pharmaceutical compositions.

In another general aspect, provided is a pharmaceutical composition comprising a multispecific CD28 antibody provided herein and a pharmaceutically acceptable carrier. In certain embodiments, the multispecific CD28 antibody is isolated. Also provided is a method of producing the pharmaceutical composition, comprising combining the multispecific antibody with a pharmaceutically acceptable carrier to obtain the pharmaceutical composition. In another aspect, provided herein is a pharmaceutical composition comprising a comprising: (a) a first binding domain that binds to CD28, and (b) a second binding domain that binds to a second target, and a pharmaceutically acceptable carrier. Any of the multispecific antibodies provided herein are contemplated in the pharmaceutical compositions.

The term "pharmaceutical composition" as used herein means a product comprising an antibody provided herein together with a pharmaceutically acceptable carrier. Antibodies of provided herein and compositions comprising them are also useful in the manufacture of a medicament for therapeutic applications.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition provided herein the biological activity of a composition provided herein. According to particular embodiments, in view of the present disclosure, any pharmaceutically acceptable carrier suitable for use in an antibody pharmaceutical composition can be used herein.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions provided herein.

In one embodiment, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment, the pH of the formulation is from about 7.0 to about 9.5. In another embodiment, the pH of the formulation is from about 3.0 to about 7.0.

In another embodiment, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments.

In another embodiment, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments.

In another embodiment, the pharmaceutical composition comprises an isotonic agent. Non-limiting examples of isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can include mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethyl-cellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments.

In another embodiment, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments.

In another embodiment, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments.

In further embodiments, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments.

In a further embodiment, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments.

In another general aspect, provided herein is a method of producing a pharmaceutical composition comprising an antibody or antigen-binding fragment thereof provided herein, comprising combining an antibody or antigen-binding fragment thereof with a pharmaceutically acceptable carrier to obtain the pharmaceutical composition.

Methods of Use

The functional activity of antibodies provided herein can be characterized by methods known in the art and as described herein. Methods for characterizing antibodies and antigen-binding fragments thereof include, but are not limited to, affinity and specificity assays including Biacore, ELISA, and OctetRed analysis; binding assays to detect the binding of antibodies to target cells by FACS; binding assays to detect the binding of antibodies to the target antigen on cells. According to particular embodiments, the methods for characterizing antibodies and antigen-binding fragments thereof include those described below. In certain embodiments, the antibody is a CD28 antibody. In some embodiments, the CD28 antibody is a CD28 multispecific antibody provided herein.

Also provided is a method of activating a T cell expressing CD28, comprising contacting the T cell with a CD28 antibody provided herein. In some embodiments, the contacting results in an increase in CD69, CD25, and/or Granzyme B expression, as compared to a control T cell expressing CD28. In certain embodiments, the T cell is a CD8+ T cell.

In another general aspect, provided is a method of inactivating a T cell expressing CD28, comprising contacting the T cell with an antibody that binds to a CD28 provided herein. In another general aspect, provided is a method of blocking activation of a T cell expressing CD28, comprising contacting the T cell with an antibody that binds to a CD28 provided herein. In another general aspect, provided is a method of modulating the activation of a T cell expressing CD28, comprising contacting the T cell with an antibody that binds to a CD28 provided herein.

In another aspect, provided herein is a method of directing a T cell expressing CD28 to a target cell, the method comprising contacting the T cell with a multispecific CD28 antibody provided herein. In another aspect, provided herein is a method of directing a T cell expressing CD28 to a target cell, the method comprising contacting the T cell with a pharmaceutical composition comprising a multispecific CD28 antibody provided herein. In some embodiments, the contacting directs the T cell to the target cell. In some embodiments the target cell expresses a second target. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells.

Also provided is a method of targeting an antigen on the surface of a target cell, the method comprising exposing the target cell to a CD28 multispecific antibody provided herein. Also provided is a method of targeting an antigen on the surface of a target cell, the method comprising exposing the target cell to a pharmaceutical composition comprising a CD28 multispecific antibody provided herein. In some embodiments the target cell expresses a second target. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells.

In another general aspect, provided is a method of targeting an antigen on the surface of a target cell, the method comprising exposing the target cell to a CD28 multispecific antibody provided herein. In another general aspect, provided is a method of targeting an antigen on the surface of a target cell, the method comprising exposing the target cell to a pharmaceutical composition comprising a CD28 multispecific antibody provided herein. In some embodiments the target cell expresses a second target. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells.

Also provided herein is a method of treating a disease or disorder in a subject, comprising administering to the subject a CD28 antibody provided herein. Also provided herein is a method of treating a disease or disorder in a subject, comprising administering to the subject a CD28 antigen binding fragment provided herein. Also provided herein is a method of treating a disease or disorder in a subject, comprising administering to the subject a pharmaceutical composition comprising a CD28 antibody provided herein. Also provided herein is a method of treating a disease or disorder in a subject, comprising administering to the subject a pharmaceutical composition comprising a CD28 antigen binding fragment provided herein.

In another aspect, provided herein is a method of inactivating a T cell expressing CD28, comprising contacting the T cell with the multispecific antibody, as provided herein. In another aspect, provided herein is a method of blocking activation of a T cell expressing CD28, comprising contacting the T cell with the multispecific antibody, as provided herein. In another aspect, provided herein is a method of modulating the activation of a T cell expressing CD28, comprising contacting the T cell with the multispecific antibody, as provided herein. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells.

In another aspect, provided herein is a method of directing a T cell expressing CD28 to a target cell, the method comprising contacting the T cell with a multispecific antibody provided herein. In some embodiments, the contacting directs the T cell to the target cell. Also provided is a method of targeting an antigen on the surface of a target cell, the method comprising exposing the target cell to a CD28 multispecific antibody or antigen binding fragment thereof provided herein. Also provided is a method of targeting an antigen on the surface of a target cell, the method comprising exposing the target cell to a pharmaceutical composition comprising a CD28 multispecific antibody or antigen binding fragment thereof provided herein. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells. In certain embodiments, the target cell is a B cell. In some embodiments, the target cell is a cancer cell.

In another general aspect, provided is a method of targeting an antigen on the surface of a target cell, the method comprising exposing the target cell to a CD28 multispecific antibody or antigen binding fragment thereof or a pharmaceutical composition provided herein. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells. In certain embodiments, the target cell is a B cell. In some embodiments, the target cell is a cancer cell.

Also provided is a method of directing CD28-expressing T cells to a second target. The methods can comprise contacting the CD28-expressing T cell with a CD28 multispecific antibody or antigen binding fragment thereof provided herein, wherein the CD28 multispecific antibody or antigen binding fragment thereof directs the CD28-expressing T cell to the second target. Also provided is a method of directing a T cell expressing CD28 to a second target, the method comprising contacting the T cell with a multispecific antibody provided herein, wherein the contacting directs the T cell to the second target. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells. In certain embodiments, the target cell is a B cell. In some embodiments, the target cell is a cancer cell.

Also provided is a method for inhibiting growth or proliferation of target cells. The methods can comprise contacting the CD28-expressing T cells with a CD28 multispecific antibody or antigen binding fragment thereof provided herein, wherein contacting the target cells with the CD28 multispecific antibody or antigen binding fragment thereof composition inhibits the growth or proliferation of the target cells. Also provided is a method of inhibiting growth or proliferation of target cells expressing a second target antigen on the cell surface, the method comprising contacting the target cells with a multispecific antibody provided herein, wherein contacting the target cells with the pharmaceutical composition inhibits growth or proliferation of the target cells. In some embodiments, the target cells are in the presence of a T cell expressing CD28 while in contact with the multispecific antibody. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells. In certain embodiments, the target cell is a B cell. In some embodiments, the target cell is a cancer cell.

Also provided herein is a method of treating a disease or disorder in a subject, comprising administering to the subject a CD28 multispecific antibody provided herein. Also provided herein is a method of treating a disease or disorder in a subject, comprising administering to the subject a multispecific antibody comprising a CD28 antigen binding fragment provided herein. Also provided herein is a method of treating a disease or disorder in a subject, comprising administering to the subject a pharmaceutical composition comprising a CD28 multispecific antibody provided herein. Also provided herein is a method of treating a disease or disorder in a subject, comprising administering to the subject a pharmaceutical composition comprising a multispecific antibody comprising a CD28 antigen binding fragment provided herein. In certain embodiments, the multispecific CD28 antibody is a multispecific CD28 antibody, wherein the second target is not CD28. In certain embodiments, the disease or disorder is caused all or in part by the second target. In some embodiments, the second target is on the surface of a target cell. In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells. In certain embodiments, the target cell is a B cell. In some embodiments, the target cell is a cancer cell.

In another general aspect, provided herein is a method of treating a disease or disorder in a subject, comprising administering to the subject an isolated multispecific antibody or antigen binding fragment thereof that specifically binds CD28 and a second target antigen presented on the surface of a target cell, or a pharmaceutical composition disclosed herein. In some embodiments, provided is a method for eliminating target cells expressing the second antigen or treating a disease caused all or in part by target cells expressing the second antigen in a subject, comprising administering an effective amount of a multispecific antibody provided herein to the subject. I In certain embodiments, the multispecific CD28 antibody is a multispecific CD28/BCMA antibody, wherein the second target is BCMA. In certain embodiments, the multispecific CD28 antibody is a multispecific CD28/Vβ17/BCMA antibody, wherein the second target is BCMA, and wherein the CD28 antibody further comprises a third binding domain that binds to Vβ17 on T cells.

In some embodiments, the subject is a subject in need thereof. In some embodiments, the subject is a human. In specific embodiments, the subject is administered an effective amount.

As used herein, the term “effective amount” refers to an amount of an active ingredient or component that elicits the desired biological or medicinal response in a subject.

According to particular embodiments, an effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms “treat,” “treating,” and “treatment” are all intended to refer to an amelioration or reversal of at least one measurable physical parameter related to a cancer, which is not necessarily discernible in the subject, but can be discernible in the subject. The terms “treat,” “treating,” and “treatment,” can also refer to causing regression, preventing the progression, or at least slowing down the progression of the disease, disorder, or condition. In a particular embodiment, “treat,” “treating,” and “treatment” refer to an alleviation, prevention of the development or onset, or reduction in the duration of one or more symptoms associated with the disease, disorder, or condition, such as a tumor or more preferably a cancer. In a particular embodiment, “treat,” “treating,” and “treatment” refer to prevention of the recurrence of the disease, disorder, or condition. In a particular embodiment, “treat,” “treating,” and “treatment” refer to an increase in the survival of a subject having the disease, disorder, or condition. In a particular embodiment, “treat,” “treating,” and “treatment” refer to elimination of the disease, disorder, or condition in the subject.

In some embodiments, a CD28 antibody provided herein is used in combination with a supplemental therapy.

As used herein, the term “in combination,” in the context of the administration of two or more therapies to a subject, refers to the use of more than one therapy. The use of the term “in combination” does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

CD28 antibodies provided herein may also be used as agents to detect CD28-expressing cells. Thus, in another methods, provided is a method of detecting a cell expressing CD28, comprising contacting a cell with a CD28 antibody provided herein. In certain embodiments, the detecting is by ELISA. In some embodiments, the detecting is by FACS analysis. Also provided are kits comprising a CD28 antibody provided herein, and instructions for use.

Enrichment and Detection Methods

In one aspect, the CD28 antibodies provided herein are used as agents to detect CD28-expressing cells. Thus, in other methods, provided is a method of detecting a cell expressing CD28, comprising contacting a cell with a CD28 antibody provided herein. In certain embodiments, the detecting is by ELISA. In some embodiments, the detecting is by FACS analysis. Also provided are kits comprising a CD28 antibody provided herein, and instructions for use.

Enrichment, isolation, separation, purification, sorting, selecting, capturing or detecting, or any combination thereof can be done using known technologies such as bead, microfluidics, solid support, columns, and the like. For example, CD28 cells may be separated or visualized using known methods when bound to the CD28 antibodies provided herein.

The CD28 antibodies or multispecific CD28 antibodies provided herein can be used to selectively enrich, isolate, separate, purify, sort, select, capture or detect CD28-expressing cells. The CD28 antibodies or multispecific CD28 antibodies provided herein may be utilized in a bispecific format, e.g. containing a first antigen binding domain that specifically binds CD28 and a second antigen binding domain that specifically binds a second target. In other embodiments, the multispecific CD28 antibodies provided herein may be utilized in a format that further incorporates a third antigen binding domain that specifically binds a third antigen (e.g., at a trispecific antibody). In other embodiments, the multispecific CD28 antibodies provided herein may be utilized in a format that further incorporates a fourth antigen binding domain that specifically binds a fourth antigen. (e.g., as a quadraspecific antibody).

In one aspect, provided herein is a method of enriching a CD28-expressing cell comprising: providing a sample comprising the CD28-expressing cell; contacting the sample with a CD28 antibody provided herein; and enriching the CD28-expressing cell bound to the CD28 antibody. In one aspect, provided herein is a method of isolating a CD28-expressing cell comprising: providing a sample comprising the CD28-expressing cell; contacting the sample with a CD28 antibody provided herein; and isolating the CD28-expressing cell bound to the CD28 antibody. In one aspect, provided herein is a method of separating a CD28-expressing cell comprising: providing a sample comprising the CD28-expressing cell; contacting the sample with a CD28 antibody provided herein; and separating the CD28-expressing cell bound to the CD28 antibody. In one aspect, provided herein is a method of purifying a CD28-expressing cell comprising: providing a sample comprising the CD28-expressing cell; contacting the sample with a CD28 antibody provided herein; and purifying the CD28-expressing cell bound to the CD28 antibody. In one aspect, provided herein is a method of sorting a CD28-expressing cell comprising: providing a sample comprising the CD28-expressing cell; contacting the sample with a CD28 antibody provided herein; and sorting the CD28-expressing cell bound to the CD28 antibody. In one aspect, provided herein is a method of selecting a CD28-expressing cell comprising: providing a sample comprising the CD28-expressing cell; contacting the sample with a CD28 antibody provided herein; and selecting the CD28-expressing cell bound to the CD28 antibody. In one aspect, provided herein is a method of capturing a CD28-expressing cell comprising: providing a sample comprising the CD28-expressing cell; contacting the sample with a CD28 antibody provided herein; and capturing the CD28-expressing cell bound to the CD28 antibody. In one aspect, provided herein is a method of detecting a CD28-expressing cell comprising: providing a sample comprising the CD28-expressing cell; contacting the sample with a CD28 antibody provided herein; and detecting the CD28-expressing cell bound to the CD28 antibody.

In one aspect, provided herein is a method of enriching a CD28-expressing cell comprising: contacting a CD28-expressing cell with a CD28 antibody provided herein; and enriching the CD28-expressing cell bound to the CD28 antibody. In one aspect, provided herein is a method of isolating a CD28-expressing cell comprising: contacting a CD28-expressing cell with a CD28 antibody provided herein; and isolating the CD28-expressing cell bound to the CD28 antibody. In one aspect, provided herein is a method of separating a CD28-expressing cell comprising: contacting a CD28-expressing cell with a CD28 antibody provided herein; and separating the CD28-expressing cell bound to the CD28 antibody. In one aspect, provided herein is a method of purifying a CD28-expressing cell comprising: contacting a CD28-expressing cell with a CD28 antibody provided herein; and purifying the CD28-expressing cell bound to the CD28 antibody. In one aspect, provided herein is a method of sorting a CD28-expressing cell comprising: contacting a CD28-expressing cell with a CD28 antibody provided herein; and sorting the CD28-expressing cell bound to the CD28 antibody. In one aspect, provided herein is a method of selecting a CD28-expressing cell comprising: contacting a CD28-expressing cell with a CD28 antibody provided herein; and selecting the CD28-expressing cell bound to the CD28 antibody. In one aspect, provided herein is a method of capturing a CD28-expressing cell comprising: contacting a CD28-expressing cell with a CD28 antibody provided herein; and capturing the CD28-expressing cell bound to the CD28 antibody. In one aspect, provided herein is a method of detecting a CD28-expressing cell comprising: contacting a CD28-expressing cell with a CD28 antibody provided herein; and detecting the CD28-expressing cell bound to the CD28 antibody.

In one aspect, provided herein is a method of enriching a CD28-expressing cell comprising: contacting a CD28-expressing cell with a CD28 antibody provided herein; and enriching the CD28-expressing cell based on binding of the CD28-expressing cell to the CD28 antibody. In one aspect, provided herein is a method of isolating a CD28-expressing cell comprising: contacting a CD28-expressing cell with a CD28 antibody provided herein; and isolating the CD28-expressing cell based on binding of the CD28-expressing cell to the CD28 antibody. In one aspect, provided herein is a method of separating a CD28-expressing cell comprising: contacting a CD28-expressing cell with a CD28 antibody provided herein; and separating the CD28-expressing cell based on binding of the CD28-expressing cell to the CD28 antibody. In one aspect, provided herein is a method of purifying a CD28-expressing cell comprising: contacting a CD28-expressing cell with a CD28 antibody provided herein; and purifying the CD28-expressing cell based on binding of the CD28-expressing cell to the CD28 antibody. In one aspect, provided herein is a method of sorting a CD28-expressing cell comprising: contacting a CD28-expressing cell with a CD28 antibody provided herein; and sorting the CD28-expressing cell based on binding of the CD28-expressing cell to the CD28 antibody. In one aspect, provided herein is a method of selecting a CD28-expressing cell comprising: contacting a CD28-expressing cell with a CD28 antibody provided herein; and selecting the CD28-expressing cell based on binding of the CD28-expressing cell to the CD28 antibody. In one aspect, provided herein is a method of capturing a CD28-expressing cell comprising: contacting a CD28-expressing cell with a CD28 antibody provided herein; and capturing the CD28-expressing cell based on binding of the CD28-expressing cell to the CD28 antibody. In one aspect, provided herein is a method of detecting a CD28-expressing cell comprising: contacting a CD28-expressing cell with a CD28 antibody provided herein; and detecting the CD28-expressing cell based on binding of the CD28-expressing cell to the CD28 antibody.

In certain embodiments of the methods, the CD28-expressing cell is a T cell. In some embodiments of the methods, the CD28-expressing cell is in a population of cells. In some embodiments of the methods, the CD28-expressing cell is in a population of lymphocytes. In some embodiments of the methods, the CD28-expressing cell is in a population of T cells. In some embodiments of the methods, the CD28-expressing cell is provided as a population of cells. In some embodiments of the methods, the CD28-expressing cell is provided as a population of lymphocytes. In some embodiments of the methods, the CD28-expressing cell is provided as a population of T cells. In some embodiments of the methods, the CD28-expressing cell is provided as a sample comprising a population of cells. In some embodiments of the methods, the CD28-expressing cell is provided as a sample comprising a population of lymphocytes. In some embodiments of the methods, the CD28-expressing cell is provided as a sample comprising a population of T cells. In some embodiments of the methods, the sample is a blood sample. In some embodiments of the methods, the sample is a tissue sample. In some embodiments of the methods, the sample is a tissue culture sample.

In some embodiments of the methods, the CD28 antibody is a multispecific CD28 antibody provided herein. In some embodiments of the methods, the CD28 antibody is a bispecific CD28 antibody provided herein. In some embodiments of the methods, the CD28 antibody is a trispecific CD28 antibody provided herein. In some embodiments of the methods, the CD28 antibody is a quadraspecific CD28 antibody provided herein. In certain embodiments, the CD28 antibody specifically binds to CD28. In one embodiment, the multispecific CD28 antibody comprises: (a) a first binding domain that binds CD28, and (b) a second binding domain that binds to a second target. In one embodiment, the multispecific CD28 antibody comprises: (a) a first binding domain that binds CD28, and (b) a second binding domain that binds to a second target, and (c) a third binding domain that binds to a third target. In one embodiment, the multispecific CD28 antibody comprises: (a) a first binding domain that binds CD28, and (b) a second binding domain that binds to a second target, (c) a third binding domain that binds to a third target, and (d) a fourth binding domain that binds to a fourth target. In one embodiment, the multispecific CD28 antibody comprises: (a) a first binding domain that specifically binds CD28, and (b) a second binding domain that specifically binds to a second target. In one embodiment, the multispecific CD28 antibody comprises: (a) a first binding domain that specifically binds CD28, and (b) a second binding domain that specifically binds to a second target, and (c) a third binding domain that specifically binds to a third target. In one embodiment, the multispecific CD28 antibody comprises: (a) a first binding domain that specifically binds CD28, and (b) a second binding domain that specifically binds to a second target, (c) a third binding domain that specifically binds to a third target, and (d) a fourth binding domain that specifically binds to a fourth target.

In specific embodiments of the methods provided herein, the method uses multi-marker detection. In some embodiments, the multi-marker detection uses a multispecific CD28 antibody provided herein. In some embodiments, the multi-marker detection uses a bispecific CD28 antibody provided herein. In some embodiments, the multi-marker detection uses a trispecific CD28 antibody provided herein. In some embodiments, the multi-marker detection uses a quadraspecific CD28 antibody provided herein.

In certain embodiments of the methods provided herein, the methods are included as steps in a T cell manufacturing process. In certain embodiments, the cells are CAR-T cells. In certain embodiments of the methods provided herein, the methods are included as steps in a T cell modification process.

In certain embodiments of the methods provided herein, the methods are included as steps in a diagnostic method. In certain embodiments of the methods provided herein, the methods are included as steps in a method to quantify the CD28-expressing T cells.

In certain embodiments of the methods provided herein, the method further comprises expanding the enriched, isolated, separated, purified, sorted, selected, captured or detected CD28-expressing cells. In certain embodiments, the expanding is in vitro. In certain embodiments, the expanding is in vivo. In certain embodiments of the methods provided herein, the method further comprises growing the enriched, isolated, separated, purified, sorted, selected, captured or detected CD28-expressing cells. In certain embodiments, the growing is in vitro. In certain embodiments, the growing is in vivo. In certain embodiments of the methods provided herein, the method further comprises quantifying the enriched, isolated, separated, purified, sorted, selected, captured or detected CD28-expressing cells.

EMBODIMENTS

This invention provides the following non-limiting embodiments.

In one set of embodiments, provided are:

1. An antibody that binds CD28 comprising:
   - (1) (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:31; and
     - (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:32;
   - (2) (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:65; and
     - (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:66;
   - (3) (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:99; and
     - (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:100; or
   - (4) (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:133; and
   (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:134.

2. The antibody of embodiment 1, (i) wherein the VH CDR1, VH CDR2, VH CDR3, VL CDR1, VL CDR2, and VL CDR3 amino acid sequences are according to the Kabat numbering system; (ii) wherein the VH CDR1, VH CDR2, VH CDR3, VL CDR1, VL CDR2, and VL CDR3 amino acid sequences are according to the Chothia numbering system; (iii) wherein the VH CDR1, VH CDR2, VH CDR3, VL CDR1, VL CDR2, and VL CDR3 amino acid sequences are according to the AbM numbering system; (iv) wherein the VH CDR1, VH CDR2, VH CDR3, VL CDR1, VL CDR2, and VL CDR3 amino acid sequences are according to the Contact numbering system; and/or (v) wherein the VH CDR1, VH CDR2, VH CDR3, VL CDR1, VL CDR2, and VL CDR3 amino acid sequences are according to the IMGT numbering system.
3. An antibody that binds CD28 comprising:
   (1) (i) a VH comprising a VH CDR1 having an amino acid sequence selected from SEQ ID NO:1, SEQ ID NO:7, SEQ ID NO:13, SEQ ID NO:19, and SEQ ID NO:25; a VH CDR2 having an amino acid sequence selected from SEQ ID NO:2, SEQ ID NO:8, SEQ ID NO:14, SEQ ID NO:20, and SEQ ID NO:26; a VH CDR3 having an amino acid sequence selected from SEQ ID NO:3, SEQ ID NO:9, SEQ ID NO:15, SEQ ID NO:21, and SEQ ID NO:27; and
      (ii) a VL comprising a VL CDR1 having an amino acid sequence selected from SEQ ID NO:4, SEQ ID NO:10, SEQ ID NO:16, SEQ ID NO:22, and SEQ ID NO:28; a VL CDR2 having an amino acid sequence selected from SEQ ID NO:5, SEQ ID NO:11, SEQ ID NO:17, SEQ ID NO:23, and SEQ ID NO:29; a VL CDR3 having an amino acid sequence selected from SEQ ID NO:6, SEQ ID NO:12, SEQ ID NO:18, SEQ ID NO:24, and SEQ ID NO:30;
   (2) (i) a VH comprising a VH CDR1 having an amino acid sequence selected from SEQ ID NO:35, SEQ ID NO:41, SEQ ID NO:47, SEQ ID NO:53, and SEQ ID NO:59; a VH CDR2 having an amino acid sequence selected from SEQ ID NO:36, SEQ ID NO:42, SEQ ID NO:48, SEQ ID NO:54, and SEQ ID NO:60; a VH CDR3 having an amino acid sequence selected from SEQ ID NO:37, SEQ ID NO:43, SEQ ID NO:49, SEQ ID NO:55, and SEQ ID NO:61; and
      (ii) a VL comprising a VL CDR1 having an amino acid sequence selected from SEQ ID NO:38, SEQ ID NO:44, SEQ ID NO:50, SEQ ID NO:56, and SEQ ID NO:62; a VL CDR2 having an amino acid sequence selected from SEQ ID NO:39, SEQ ID NO:45, SEQ ID NO:51, SEQ ID NO:57, and SEQ ID NO:63; a VL CDR3 having an amino acid sequence selected from SEQ ID NO:40, SEQ ID NO:46, SEQ ID NO:52, SEQ ID NO:58, and SEQ ID NO:64;
   (3) (i) a VH comprising a VH CDR1 having an amino acid sequence selected from SEQ ID NO:69, SEQ ID NO:75, SEQ ID NO:81, SEQ ID NO:87, and SEQ ID NO:93; a VH CDR2 having an amino acid sequence selected from SEQ ID NO:70, SEQ ID NO:76, SEQ ID NO:82, SEQ ID NO:88, and SEQ ID NO:94; a VH CDR3 having an amino acid sequence selected from SEQ ID NO:71, SEQ ID NO:77, SEQ ID NO:83, SEQ ID NO:89, and SEQ ID NO:95; and
      (ii) a VL comprising a VL CDR1 having an amino acid sequence selected from SEQ ID NO:72, SEQ ID NO:78, SEQ ID NO:84, SEQ ID NO:90, and SEQ ID NO:96; a VL CDR2 having an amino acid sequence selected from SEQ ID NO:73, SEQ ID NO:79, SEQ ID NO:85, SEQ ID NO:91, and SEQ ID NO:97; a VL CDR3 having an amino acid sequence selected from SEQ ID NO:74, SEQ ID NO:80, SEQ ID NO:86, SEQ ID NO:92, and SEQ ID NO:98; and
   (4) (i) a VH comprising a VH CDR1 having an amino acid sequence selected from SEQ ID NO:103, SEQ ID NO:109, SEQ ID NO:115, SEQ ID NO:121, and SEQ ID NO:127; a VH CDR2 having an amino acid sequence selected from SEQ ID NO:104, SEQ ID NO:110, SEQ ID NO:116, SEQ ID NO:122, and SEQ ID NO:128; a VH CDR3 having an amino acid sequence selected from SEQ ID NO:105, SEQ ID NO:111, SEQ ID NO:117, SEQ ID NO:123, and SEQ ID NO:129; and
      (ii) a VL comprising a VL CDR1 having an amino acid sequence selected from SEQ ID NO:106, SEQ ID NO:112, SEQ ID NO:118, SEQ ID NO:124, and SEQ ID NO:130; a VL CDR2 having an amino acid sequence selected from SEQ ID NO:107, SEQ ID NO:113, SEQ ID NO:119, SEQ ID NO:125, and SEQ ID NO:131; a VL CDR3 having an amino acid sequence selected from SEQ ID NO:108, SEQ ID NO:114, SEQ ID NO:120, SEQ ID NO:126, and SEQ ID NO:132.
4. The antibody of any one of embodiments 1 to 3, wherein the antibody further comprises one or more framework regions as set forth in in SEQ ID NO:31, SEQ ID NO:32, SEQ ID NO:65, SEQ ID NO:66, SEQ ID NO:99, SEQ ID NO:100, SEQ ID NO:133 and/or SEQ ID NO:134.
5. The antibody of any one of embodiments 1 to 4, wherein the antibody comprises a VH having an amino acid sequence selected from SEQ ID NO:31, SEQ ID NO:65, SEQ ID NO:99, and SEQ ID NO:133, and a VL having an amino acid sequence selected from SEQ ID NO:32, SEQ ID NO:66, SEQ ID NO:100, and SEQ ID NO:134.
6. The antibody of any one of embodiments 1 to 4, (i) wherein the antibody comprises a VH having an amino acid sequence of SEQ ID NO:31, and a VL having an amino acid sequence of SEQ ID NO:32; (ii) wherein the antibody comprises a VH having an amino acid sequence of SEQ ID NO:65, and a VL having an amino acid sequence of SEQ ID NO:66; (iii) wherein the antibody comprises a VH having an amino acid sequence of SEQ ID NO:99, and a VL having an amino acid sequence of SEQ ID NO:100; or (iv) wherein the antibody comprises a VH having an amino acid sequence of SEQ ID NO:133, and a VL having an amino acid sequence of SEQ ID NO:134.
7. The antibody of any one of embodiments 1 to 6, wherein the antibody is a humanized antibody.
8. The antibody of any one of embodiments 1 to 7, wherein the antibody is an IgG antibody.
9. The antibody of embodiment 8, wherein the IgG antibody is an IgG1, IgG2, IgG3, or IgG4 antibody.

10. The antibody of any one of embodiments 1 to 9, wherein the antibody comprises a kappa light chain.
11. The antibody of any one of embodiments 1 to 9, wherein the antibody comprises a lambda light chain.
12. The antibody of any one of embodiments 1 to 11, wherein the antibody is a monoclonal antibody.
13. The antibody of any one of embodiments 1 to 12, wherein the antibody binds a CD28 antigen.
14. The antibody of any one of embodiments 1 to 12, wherein the antibody binds a CD28 epitope.
15. The antibody of any one of embodiments 1 to 14, wherein the antibody specifically binds to CD28.
16. The antibody of any one of embodiments 1 to 15, wherein the VH CDR1, VH CDR2, VH CDR3, VL CDR1, VL CDR2 and VL CDR3 form a binding site for an antigen of the CD28.
17. The antibody of any one of embodiments 1 to 15, wherein the VH CDR1, VH CDR2, VH CDR3, VL CDR1, VL CDR2 and VL CDR3 form a binding site for an epitope of the CD28.
18. The antibody of any one of embodiments 1 to 17, wherein the CD28 is present on the surface of a T cell.
19. The antibody of any one of embodiments 1 to 18, wherein the antibody is multivalent.
20. The antibody of embodiment 19, wherein the antibody is capable of binding at least three antigens.
21. The antibody of embodiment 19, wherein the antibody is capable of binding at least four antigens.
22. The antibody of embodiment 19, wherein the antibody is capable of binding at least five antigens.
23. The antibody of any one of embodiments 1 to 22, wherein the antibody is a multispecific antibody.
24. The antibody of embodiment 23, wherein the antibody is a bispecific antibody.
25. The antibody of embodiment 23, wherein the antibody is a trispecific antibody.
26. The antibody of embodiment 23, wherein the antibody is a quadraspecific antibody.
27. A multispecific antibody, wherein the multispecific antibody comprises: a first binding domain that binds to CD28 and a second binding domain that binds to a second target that is not CD28, wherein the first binding domain that binds to CD28 comprises:
    (1) (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:31; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:32;
    (2) (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:65; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:66;
    (3) (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:99; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:100; or
    (4) (i) a VH comprising a VH CDR1, a VH CDR2, and a VH CDR3 having an amino acid sequence of a VH CDR1, a VH CDR2, and a VH CDR3, respectively, of a VH having an amino acid sequence of SEQ ID NO:133; and (ii) a VL comprising a VL CDR1, a VL CDR2, and a VL CDR3 having an amino acid sequence of a VL CDR1, a VL CDR2, and a VL CDR3, respectively, of a VL having an amino acid sequence of SEQ ID NO:134.
28. The multispecific antibody of embodiment 27, (i) wherein the VH CDR1, VH CDR2, VH CDR3, VL CDR1, VL CDR2, and VL CDR3 amino acid sequences are according to the Kabat numbering system; (ii) wherein the VH CDR1, VH CDR2, VH CDR3, VL CDR1, VL CDR2, and VL CDR3 amino acid sequences are according to the Chothia numbering system; (iii) wherein the VH CDR1, VH CDR2, VH CDR3, VL CDR1, VL CDR2, and VL CDR3 amino acid sequences are according to the AbM numbering system; (iv) wherein the VH CDR1, VH CDR2, VH CDR3, VL CDR1, VL CDR2, and VL CDR3 amino acid sequences are according to the Contact numbering system; and/or (v) wherein the VH CDR1, VH CDR2, VH CDR3, VL CDR1, VL CDR2, and VL CDR3 amino acid sequences are according to the IMGT numbering system.
29. A multispecific antibody, wherein the multispecific antibody comprises: a first binding domain that binds to CD28 and a second binding domain that binds to a second target that is not CD28, wherein the first binding domain that binds to CD28 comprises:
    (1) (i) a VH comprising a VH CDR1 having an amino acid sequence selected from SEQ ID NO:1, SEQ ID NO:7, SEQ ID NO:13, SEQ ID NO:19, and SEQ ID NO:25; a VH CDR2 having an amino acid sequence selected from SEQ ID NO:2, SEQ ID NO:8, SEQ ID NO:14, SEQ ID NO:20, and SEQ ID NO:26; a VH CDR3 having an amino acid sequence selected from SEQ ID NO:3, SEQ ID NO:9, SEQ ID NO:15, SEQ ID NO:21, and SEQ ID NO:27; and
        (ii) a VL comprising a VL CDR1 having an amino acid sequence selected from SEQ ID NO:4, SEQ ID NO:10, SEQ ID NO:16, SEQ ID NO:22, and SEQ ID NO:28; a VL CDR2 having an amino acid sequence selected from SEQ ID NO:5, SEQ ID NO:11, SEQ ID NO:17, SEQ ID NO:23, and SEQ ID NO:29; a VL CDR3 having an amino acid sequence selected from SEQ ID NO:6, SEQ ID NO:12, SEQ ID NO:18, SEQ ID NO:24, and SEQ ID NO:30;
    (2) (i) a VH comprising a VH CDR1 having an amino acid sequence selected from SEQ ID NO:35, SEQ ID NO:41, SEQ ID NO:47, SEQ ID NO:53, and SEQ ID NO:59; a VH CDR2 having an amino acid sequence selected from SEQ ID NO:36, SEQ ID NO:42, SEQ ID NO:48, SEQ ID NO:54, and SEQ ID NO:60; a VH CDR3 having an amino acid sequence selected from SEQ ID NO:37, SEQ ID NO:43, SEQ ID NO:49, SEQ ID NO:55, and SEQ ID NO:61; and
        (ii) a VL comprising a VL CDR1 having an amino acid sequence selected from SEQ ID NO:38, SEQ ID NO:44, SEQ ID NO:50, SEQ ID NO:56, and SEQ ID NO:62; a VL CDR2 having an amino acid sequence selected from SEQ ID NO:39, SEQ ID NO:45, SEQ ID NO:51, SEQ ID NO:57, and SEQ ID NO:63; a VL CDR3 having an amino acid sequence selected from SEQ ID NO:40, SEQ ID NO:46, SEQ ID NO:52, SEQ ID NO:58, and SEQ ID NO:64;

(3) (i) a VH comprising a VH CDR1 having an amino acid sequence selected from SEQ ID NO:69, SEQ ID NO:75, SEQ ID NO:81, SEQ ID NO:87, and SEQ ID NO:93; a VH CDR2 having an amino acid sequence selected from SEQ ID NO:70, SEQ ID NO:76, SEQ ID NO:82, SEQ ID NO:88, and SEQ ID NO:94; a VH CDR3 having an amino acid sequence selected from SEQ ID NO:71, SEQ ID NO:77, SEQ ID NO:83, SEQ ID NO:89, and SEQ ID NO:95; and (ii) a VL comprising a VL CDR1 having an amino acid sequence selected from SEQ ID NO:72, SEQ ID NO:78, SEQ ID NO:84, SEQ ID NO:90, and SEQ ID NO:96; a VL CDR2 having an amino acid sequence selected from SEQ ID NO:73, SEQ ID NO:79, SEQ ID NO:85, SEQ ID NO:91, and SEQ ID NO:97; a VL CDR3 having an amino acid sequence selected from SEQ ID NO:74, SEQ ID NO:80, SEQ ID NO:86, SEQ ID NO:92, and SEQ ID NO:98; and (4) (i) a VH comprising a VH CDR1 having an amino acid sequence selected from SEQ ID NO:103, SEQ ID NO:109, SEQ ID NO:115, SEQ ID NO:121, and SEQ ID NO:127; a VH CDR2 having an amino acid sequence selected from SEQ ID NO:104, SEQ ID NO:110, SEQ ID NO:116, SEQ ID NO:122, and SEQ ID NO:128; a VH CDR3 having an amino acid sequence selected from SEQ ID NO:105, SEQ ID NO:111, SEQ ID NO:117, SEQ ID NO:123, and SEQ ID NO:129; and (ii) a VL comprising a VL CDR1 having an amino acid sequence selected from SEQ ID NO:106, SEQ ID NO:112, SEQ ID NO:118, SEQ ID NO:124, and SEQ ID NO:130; a VL CDR2 having an amino acid sequence selected from SEQ ID NO:107, SEQ ID NO:113, SEQ ID NO:119, SEQ ID NO:125, and SEQ ID NO:131; a VL CDR3 having an amino acid sequence selected from SEQ ID NO:108, SEQ ID NO:114, SEQ ID NO:120, SEQ ID NO:126, and SEQ ID NO:132.

30. The antibody of any one of embodiments 27 to 29, wherein the antibody further comprises one or more framework regions as set forth in in SEQ ID NO:31, SEQ ID NO:32, SEQ ID NO:65, SEQ ID NO:66, SEQ ID NO:99, SEQ ID NO:100, SEQ ID NO:133 and/or SEQ ID NO:134.

31. The antibody of any one of embodiments 27 to 30, wherein the antibody comprises a VH having an amino acid sequence selected from SEQ ID NO:31, SEQ ID NO:65, SEQ ID NO:99, and SEQ ID NO:133, and a VL having an amino acid sequence selected from SEQ ID NO:32, SEQ ID NO:66, SEQ ID NO:100, and SEQ ID NO:134.

32. The antibody of any one of embodiments 27 to 31, (i) wherein the antibody comprises a VH having an amino acid sequence of SEQ ID NO: 31, and a VL having an amino acid sequence of SEQ ID NO: 32; (ii) wherein the antibody comprises a VH having an amino acid sequence of SEQ ID NO: 65, and a VL having an amino acid sequence of SEQ ID NO: 66; (iii) wherein the antibody comprises a VH having an amino acid sequence of SEQ ID NO: 99, and a VL having an amino acid sequence of SEQ ID NO: 100; or (iv) wherein the antibody comprises a VH having an amino acid sequence of SEQ ID NO: 133, and a VL having an amino acid sequence of SEQ ID NO: 134.

33. The multispecific antibody of embodiment 27, wherein the VH CDR1, VH CDR2, VH CDR3, VL CDR1, VL CDR2, and VL CDR3 amino acid sequences are according to the Kabat numbering system.

34. The multispecific antibody of embodiment 27, wherein the VH CDR1, VH CDR2, VH CDR3, VL CDR1, VL CDR2, and VL CDR3 amino acid sequences are according to the Chothia numbering system.

35. The multispecific antibody of embodiment 27, wherein the VH CDR1, VH CDR2, VH CDR3, VL CDR1, VL CDR2, and VL CDR3 amino acid sequences are according to the AbM numbering system.

36. The multispecific antibody of embodiment 27, wherein the VH CDR1, VH CDR2, VH CDR3, VL CDR1, VL CDR2, and VL CDR3 amino acid sequences are according to the Contact numbering system.

37. The multispecific antibody of embodiment 27, wherein the VH CDR1, VH CDR2, VH CDR3, VL CDR1, VL CDR2, and VL CDR3 amino acid sequences are according to the IMGT numbering system.

38. The multispecific antibody of any one of embodiments 27 to 37, wherein the antibody is a humanized antibody.

39. The multispecific antibody of any one of embodiments 27 to 38, wherein the antibody is an IgG antibody.

40. The multispecific antibody of embodiment 39, wherein the IgG antibody is an IgG1, IgG2, IgG3, or IgG4 antibody.

41. The multispecific antibody of any one of embodiments 27 to 40, wherein the antibody comprises a kappa light chain.

42. The multispecific antibody of any one of embodiments 27 to 40, wherein the antibody comprises a lambda light chain.

43. The multispecific antibody of any one of embodiments 27 to 42, wherein the antibody is a monoclonal antibody.

44. The multispecific antibody of any one of embodiments 27 to 43, wherein the first binding domain binds a CD28 antigen.

45. The multispecific antibody of any one of embodiments 27 to 44, wherein the first binding domain binds a CD28 epitope.

46. The multispecific antibody of any one of embodiments 27 to 45, wherein the first binding domain specifically binds to CD28.

47. The multispecific antibody of any one of embodiments 27 to 46, wherein the VH CDR1, VH CDR2, VH CDR3, VL CDR1, VL CDR2 and VL CDR3 of the first binding domain form a binding site for an antigen of the CD28.

48. The multispecific antibody of any one of embodiments 27 to 46, wherein the VH CDR1, VH CDR2, VH CDR3, VL CDR1, VL CDR2 and VL CDR3 of the first binding domain form a binding site for an epitope of the CD28.

49. The multispecific antibody of any one of embodiments 27 to 48, wherein the CD28 is present on the surface of a T cell.

50. The multispecific antibody of any one of embodiments 27 to 49, wherein the second binding domain binds an antigen of the second target.

51. The multispecific antibody of any one of embodiments 27 to 50, wherein the second binding domain binds an epitope of the second target.

52. The multispecific antibody of any one of embodiments 27 to 51, wherein the second binding domain specifically binds to the second target.
53. The multispecific antibody of any one of embodiments 27 to 52, wherein the VH CDR1, VH CDR2, VH CDR3, VL CDR1, VL CDR2 and VL CDR3 of the second binding domain form a binding site for an antigen of the second target.
54. The multispecific antibody of any one of embodiments 27 to 52, wherein the VH CDR1, VH CDR2, VH CDR3, VL CDR1, VL CDR2 and VL CDR3 of the second binding domain form a binding site for an epitope of the second target.
55. The multispecific antibody of any one of embodiments 27 to 54, wherein the second target is present on the surface of a T cell.
56. The multispecific antibody of any one of embodiments 27 to 55, wherein the antibody is multivalent.
57. The multispecific antibody of embodiment 56, wherein the antibody is capable of binding at least three antigens.
58. The multispecific antibody of embodiment 56, wherein the antibody is capable of binding at least four antigens.
59. The multispecific antibody of embodiment 56, wherein the antibody is capable of binding at least five antigens.
60. The multispecific antibody of any one of embodiments 27 to 56, wherein the antibody is a bispecific antibody.
61. The multispecific antibody of any one of embodiments 27 to 56, wherein the antibody is a trispecific antibody.
62. The multispecific antibody of any one of embodiments 27 to 56, wherein the antibody is a quadraspecific antibody.
63. The multispecific antibody of any one of embodiments 27 to 56, wherein the multispecific antibody further comprises: a third binding domain that binds to a third target.
64. The multispecific antibody of embodiment 63, wherein the multispecific antibody further comprises a fourth binding domain that binds to a fourth target.
65. A multispecific antibody comprising: a first means capable of binding CD28 on the surface of a cell; and a second means capable of binding a second target antigen that is not CD28.
66. A nucleic acid encoding the antibody of any one of embodiments 1 to 65.
67. A vector comprising the nucleic acid of embodiment 66.
68. A host cell comprising the vector of embodiment 67.
69. A kit comprising the vector of embodiment 67 and packaging for the same.
70. A kit comprising the antibody of any one of embodiments 1 to 65 and packaging for the same.
71. A pharmaceutical composition comprising the antibody of any one of embodiments 1 to 65, and a pharmaceutically acceptable carrier.
72. A method of producing the pharmaceutical composition of embodiment 71, comprising combining the antibody with a pharmaceutically acceptable carrier to obtain the pharmaceutical composition.
73. A method of activating a T cell expressing CD28, comprising contacting the T cell with the antibody of any one of embodiments 1 to 65.
74. The method of embodiment 73, wherein the contacting results in an increase in CD69, CD25, and/or Granzyme B expression, as compared to a control T cell expressing CD28.
75. A process for making an antibody that binds to more than one target molecule, the molecule comprising: a step for performing a function of obtaining a binding domain capable of binding to CD28 on the surface of a cell; a step for performing a function of obtaining a binding domain capable of binding to a second target antigen on a second cell; and a step for performing a function of providing an antibody capable of binding to a CD28 on the surface of a cell and a second target antigen on a second cell.
76. The process of embodiment 75, wherein the step for performing a function of obtaining a binding domain capable of binding to a second target antigen is repeated n times and further comprising n steps for performing a function of providing a binding domain capable of binding to CD28 on the surface of a cell and n number of target molecules, wherein n is at least 2.
77. A method of directing a cell expressing CD28 to a second target, the method comprising contacting the CD28-expressing cell with the multispecific antibody of any one of embodiments 27 to 65, wherein the contacting directs the CD28-expressing cell to the second target.
78. A method of inhibiting growth or proliferation of target cells expressing a second target, the method comprising contacting the target cells with the multispecific antibody of any one of embodiments 27 to 65, wherein contacting the target cells with the multispecific antibody inhibits growth or proliferation of the target cells.
79. The method of embodiment 78, wherein the target cells are in the presence of a CD28-expressing cell while in contact with the multispecific antibody.
80. A method for eliminating target cells expressing the second target in a subject, comprising administering an effective amount of the multispecific antibody of any one of embodiments 27 to 65 to the subject.
81. A method for treating a disease caused all or in part by target cells expressing the second target in a subject, comprising administering an effective amount of the multispecific antibody of any one of embodiments 27 to 65 to the subject.

Provided in the Examples herein are exemplary antibodies that bind to CD28.

Exemplary binding agents that bind to CD28 are provided herein, for example in the Examples, as well as Tables 1-6.

Particular embodiments of this invention are described herein. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. A number of embodiments of the invention have been described. Nevertheless, it will be understood that various modifications may be made without departing from the spirit and scope of the invention. Accordingly, the descriptions in the Examples section are intended to illustrate but not limit the scope of invention described in the claims.

EXAMPLES

Example 1: Preparation of CD28 Antibodies

Example 1.1: Materials and Methods

Anti-CD28 antibody generation. OMNIRATS were immunized twice weekly with recombinant human CD28 (R&D Systems, Inc., MN, USA; Catalog #: 342-CD-200; LOT #: XT321505A) for a total of 12 immunization boosts by following a Repetitive Immunizations Multiple Sites (RIMMS) protocol. Sera was collected and assessed for circulating IgG specific antibodies to CD28 and titers were determined via a solid phase Elisa with antigen being coated directly on the plate. Lymph nodes were harvested for B lymphocytes fusion. Hybridoma supernatants were screened by LUMINEX using the immunogen and expanded pan-T cells. Hits were V-region recovered and formatted human IgG1 antibody.

Cell culture. NCI-H929 myeloma cells were cultured in RPMI-1640 Medium (A1049101, Thermofisher) containing fetal bovine serum (10099-141, Gibco) to a final concentration of 20%. Cells were subcultured every 2-3 days by spinning the culture at 1500 rpm for 5 mins at 37° C. Culture supernatant was discarded, and cells were seeded back in fresh media at a density of 0.5-1×106/ml. Frozen PBMCs were obtained from Hemacare. PBMCs were also isolated from fresh blood from normal healthy volunteers from Clinigene after informed consent.

Binding assay. PBMCs (Donor lot #19054141, Hemacare) were thawed rapidly in a 37° C. water bath and subjected to CD3 T cell isolation using EasySep™ Human T Cell Isolation Kit (17951, Stemcell). Post Pan T cell isolation, 0.1×106 cells were seeded per well of a 96 well V-bottom plate. Cells were stained with the fixable violet live/dead stain (L34955, Thermofisher) for 20 mins on ice in dark according to the manufacturer's protocol. Post staining cells were washed with FACS buffer (PBS+2% FBS) by spinning at 1500 rpm for 5 mins. Supernatant was discarded and cells were suspended in 100 μl the respective antibody dilutions with a starting concentration of 5 μg/ml and 3-fold serial dilutions. Antibody dilutions were prepared in FACS buffer. Cells were incubated with the antibody dilutions for 30 mins at 37° C. At the end of the incubation period, cells were washed twice with FACS buffer as above followed by staining with PE conjugated Goat polyclonal antibody to human IgG (ab98596, Abcam) at a 1:50 dilution in FACS buffer. Cells were incubated with the secondary antibody for 30 mins on ice. At the end of incubation period the cells were washed with FACS buffer as above. Cells were fixed by resuspending in 100 μl BD cytofix buffer (554655, BD Bioscience) and incubated for 20 mins on ice. Cells were pelleted and resuspended in FACS buffer for acquisition on the NOVOCYTE flow cytometer (ACEA Biosciences). For binding assays using the H929 cells, 0.1×106 H929 cells were seeded per well of a 96 well V-bottom plate and stained as above. Samples were analyzed by gating on the live cells and percentage binding was obtained by subtracting the background fluorescence from the secondary only control.

Agonism assay. Antibody dilutions was prepared in PBS at a starting concentration of 1 μg/ml followed by 4-fold serial dilutions. Wells with no antibody addition were used as negative controls. 100 μl of the antibody dilutions were used to coat 96 well flat bottom cell culture plates with incubation at 37° C. for 2 hours. PBMCs (Donor lots #19054456, 19057652, Hemacare) were thawed and subjected to Pan T cells isolation using the EasySep™ Human T Cell Isolation Kit (17951, Stemcell). Isolated Pan T cells were counted and stained with cell trace violet dye (C34557, Thermofisher) as per the manufacturer's protocol. Antibody coated plates were washed with 200 μl media and 0.3×106 CTV labeled Pan T cells were plated per well. Plates were incubated at 37° C. for 96 hours in a 5% CO2 incubator. At the end of the incubation period, the cells were spun down at 1500 rpm for 5 mins. The 150 μl of cell culture supernatant was collected and stored at −20° C. for cytokine profiling using LUMINEX. The cell pellet was subjected to APC-Cy7 live/dead stain (L10119, Thermofisher). Post live/dead staining the cells were washed with FACS buffer. The pellet was then resuspended in FACS buffer containing Fc block (564220, BD Biosciences) and incubated on ice for 10 mins following which the cells were stained with Brilliant Violet 785™ conjugated CD25 (302638, Biolegend) and PE/Cy7 conjugated CD71 (334112, Biolegend) antibodies and incubated on ice for 30 mins. At the end of incubation period the cells were washed with FACS buffer and the cells were fixed by resuspending in 100 μl BD cytofix buffer (554655, BD bioscience) and incubated for 20 mins on ice. Post fixation, the cells were washed, and the samples were resuspended in FACS buffer and acquired on the Novocyte flow cytometer. Proliferation was monitored by CTV dye. Cells were gated on the live cell population, followed by gating on Vβ17+ T cells and Vβ17− T cells. Expression of CD25, CD71 and CTV dye was monitored on each cell population and plotted as % positive cells against log antibody concentration using a 4-parameter non-linear regression curve.

Effector profiling. PBMCs (Donors HPU-00284 from Clinigene and donor lot #19054141, 19054456, 20061101 from Hemacare) were thawed and subjected to EasySep™ Human T Cell Isolation Kit (17951, Stemcell). H929 cells were counted and plated at 10,000 cells per well in a 96 well U-bottom plate in 100 μl of media. Isolated Pan T cells were counted and stained with cell trace violet dye (C34557, Thermofisher) as per the manufacturer's protocol. Vβ17 T cell frequency was determined in the Pan T cells from each donor using the PE conjugated TCR Vβ17 antibody (IM2048, Beckman Coulter). CTV labeled Pan T cells were then added to the plated H929 cells such that an effector to target ratio of 1 Vβ17:1 H929 cell was obtained. 80 μl of the effector cell suspension in RPMI media +10% FBS was added per well. For example, the Vβ17 percentage for HPU-00284 was 4.3%, so 0.23×106 cells were plated per well in 80 μl media. 10× concentration of the antibodies were prepared (10 μg/ml) followed by 4-fold serial dilutions in RPMI media +10% FBS. 20 μl of the serially diluted Ab was added to the 180 μl of the co-culture making the final concentration of the antibodies in coculture as 1×. The cell culture plates were incubated at 37° C. for 96 hrs. At the end of the incubation period, the cells were spun down at 1500 rpm for 5 mins. The 150 μl of cell culture supernatant was collected and stored at −20° C. for cytokine profiling by LUMINEX. Cells were stained with APC-Cy7 live/dead stain (L10119, Thermofisher) followed by staining with Fc block (564220, BD Biosciences). The cell pellet was taken for staining with Brilliant Violet 785™ anti-human CD25 (302638, Biolegend), PE/Cy7 anti-human CD71 (334112, Biolegend), BV 650 Anti human TIM3 (345028, Biolegend), Alexa Fluor® 488 anti-human LAG3 (369326, Biolegend), and Brilliant Violet 711 anti-human PD1 antibodies (cat #329928, Biolegend) as per the manufacturer's recommendation. Cells were washed post staining in FACS buffer and fixed with BD cytofix buffer (554655, BD Bioscience). Post fixation, samples were resuspended in FACS buffer and acquired on the Novocyte flow cytometer. Cells were gated on the live cell population, followed by gating on Vβ17+ T cells and Vβ17− T cells. Expression of CD25, CD71, TIM3, LAG3, PD1 and CTV dye was monitored on each cell population and plotted as % positive cells against log antibody concentration using a 4-parameter non-linear regression curve using GRAPHPAD Prism version 8.1.1.

Luminex analysis. Supernatants from the effector profiling assay were slowly thawed and diluted 1:10 using RPMI media +10% FBS. Cytokine analysis was carried out using the MILLIPLEX MAP Human CD8+ T Cell Magnetic Bead Panel Immunology Multiplex Assay (HCD8MAG-15K, Millipore). Plates were read using the LUMINEX plate reader (Magpix).

In vitro cytotoxicit), assay. PBMCs (Donor lots #18047563, 19056279 from Hemacare) were thawed and subjected to Pan T cell isolation using the EasySep™ Human T Cell Isolation Kit (17951, Stemcell). Another set was subjected to Vβ17 depletion using EasySep™ Human PE Positive Selection Kit (18551, Stemcells) followed by Pan T cell isolation. H929 cells were labeled with 0.5 μm of CTV dye (C34557, Thermofisher) as per the manufacturer's protocol, counted and plated at 10,000 cells per well in a 96 well U-bottom plate in 100 μl of RPMI media (ATCC modification)+20% FBS. Vβ17 T cell frequency was determined in the Pan T cells from each donor using the PE conjugated TCR Vβ17 antibody (IM2048, Beckman Coulter). CTV labeled Pan T cells were then added to the plated H929 cells such that an effector to target ratio of 1 Vβ17:1 H929 cell was obtained. 80 μl of the effector cell suspension in RPMI media +10% FBS was added per well. 10× concentration of the antibodies were prepared (10 μg/ml) followed by 4-fold serial dilutions in media. 20 μl of the serially diluted antibody was added to the 180 μl of the co-culture making the final concentration of the antibodies in coculture as 1×. The cell culture plates were incubated at 37° C. for 96 hrs. At the end of the incubation period, the cells were spun down at 1500 rpm for 5 mins. At the end of incubation period, the cells were spun down, 150 μl of cell culture supernatant removed and cells were resuspended in 50 μl of 7AAD (420404, Biolegend) diluted 1:50 in PBS and acquired on the Novocyte flow cytometer. Target cells were identified as CTV positive cells and percentage of dead cells within the target cells was gated as 7AAD+ cells. Antibody specific percentage dead cells were calculated by subtracting the lysis observed in wells containing only Pan T cells and H929 cells. Percentage dead cells were plotted against log concentration of the antibody in a 4-parameter non-linear regression curve using GRAPHPAD Prism version 8.1.1.

De novo sequencing of commercially available mouse anti-human CD28 clone CD28 antibody was obtained from a commercial source. Antibody isotype was mouse IgG1, kappa. Sample preparation and LC/MSMS analysis were performed at Protea Bioscience Inc. (Morgantown, WV). The sample was reduced and alkylated, divided into seven aliquots, and proteolytically digested with Trypsin/LysC, Chymotrypsin, LysC, Pepsin, and AspN, Elastase, and Proteinase K enzymes. Resulting peptides were desalted using a ZIPTIP C18 Pipette Tips and separated on-line using reverse phase chromatography. Mass spectrometry was performed on Thermo Q-EXACTIVE spectrometer using HCD fragmentation. MS data sets were analyzed using PEAKS software by matching de novo sequence tags to an IMGT-based antibody sequences database. Gaps in the sequence were assigned using Contig sequence assembly of de novo identified peptides. All CDRs and hyper-mutations were confirmed by inspecting the MS/MS spectra. Leu and Ile amino acid residues are practically indistinguishable by mass spectrometry. Leu/Ile in the CDR regions were identified by aligning the determined sequence to a V-region sequence database and confirmed by chymotrypsin enzyme specificity. The expected confidence in Leu/Ile identifications in the CDRs is 80%.

Example 1.2: Amino Acid Sequences of Exemplary CD28 Antibodies

Amino acid sequences of exemplary CD28 antibodies are provided in Tables 1-6. Exemplary CD28 antibody clones include C28B11, C28B19, C28B103, and C28B105. VH and VL amino acid sequences are provided in Table 1. Kabat CDR amino acid sequences are provided in Table 2. Chothia CDR amino acid sequences are provided in Table 3. AbM CDR amino acid sequences are provided in Table 4. Contact CDR amino acid sequences are provided in Table 5. IMGT CDR amino acid sequences are provided in Table 6. The numbers below each sequence reflect the respective SEQ ID NO.

TABLE 1

CD28 Antibody VH and VL Amino Acid Sequences

| # | Protein Name | HC Isotype | LC Isotype | VH AA sequence | VL AA sequence | Heavy Chain AA sequence | Light Chain AA sequence |
|---|---|---|---|---|---|---|---|
| 1 | C28B11 | IgG1 | — | EVQLLESGGGLGQPGGSLRLSCAASEFTFTSYAMSWVRQAPGKGLEWVSAISGSGGRTYYADSVKGRFTISRDNSKNTLYLQMNSLRAEDTAVYYCAKGAGYWYFDLWGRGTLVTVSS 31 | EIVLTQSPATLSLSPGERAILSCRASQSVSSYLAWYQQKPGQAPRLLIYDASNRATGIPARFSGSGSGTDFTLTISSLEPEDFAVYYCQQRSNWPLTFGGGTKVEIK 32 | EVQLLESGGGLGQPGGSLRLSCAASEFTFTSYAMSWVRQAPGKGLEWVSAISGSGGRTYYADSVKGRFTISRDNSKNTLYLQMNSLRAEDTAVYYCAKGGAGYWYFDLWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGASSVFLFPPKPKDTLMISRTPEVTCVVVDVSAEDPEVKFNWYVDGVEVHNAKTKPREEQYNSTYRVVSVLTVLHQDWLNGKEYKCKVSNKALPSSIEKTISKAKGQPREPQVYTLPPSREEMTKNQVSLTCLVKGFYPSDIAVEWESNGQPENNYKTTPPVLDSDGSFLLYSKLTVDKSRWQQGNVFSCSVMHEALHNHYTQKSLSLSPGK 33 | EIVLTQSPATLSLSPGERAILSCRASQSVSSYLAWYQQKPGQAPRLLIYDASNRATGIPARFSGSGSGTDFTLTISSLEPEDFAVYYCQQRSNWPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC 34 |

TABLE 1 -continued

CD28 Antibody VH and VL Amino Acid Sequences

| # | Protein Name | HC Isotype | LC Isotype | VH AA sequence | VL AA sequence | Heavy Chain AA sequence | Light Chain AA sequence |
|---|---|---|---|---|---|---|---|
| 2 | C28B19 | IgG1 | — | QVQLQQPGSELVRPGASVKLSCKASGYTFTSYWMHWVKQRHGQGLEWIGNIYPGSGRTNYDEKFKSKGTLTVDTSSRTAYMHLSSLTSEDSAVYYCTREHYGSNSHPMDYWGQGTSVTVSS<br>65 | DIQMTQSPASLSASVGETVTITCGASENIYGSLNWYQRKQGKSPQLLIYGATNLADGMSSRFSGSGSGRQFSLKISSLHPDDVATYYCQNLLSTPYTFGGGTKLELK<br>66 | QVQLQQPGSELVRPGASVKLSCKASGYTFTSYWMHWVKQRHGQGLEWIGNIYPGSGRTNYDEKFKSKGTLTVDTSSRTAYMHLSSLTSEDSAVYYCTREHYGSNSHPMDYWGQGTSVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFLLYSKLTVDKSRWQQGNVFSCSVMHEALHNHYTQKSLSLSPGK<br>67 | DIQMTQSPASLSASVGETVTITCGASENIYGSLNWYQRKQGKSPQLLIYGATNLADGMSSRFSGSGSGRQFSLKISSLHPDDVATYYCQNLLSTPYTFGGGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC<br>68 |
| 3 | C28B103 | IgG1 | — | QVQLQQWGAGLLKPSETLSLICAVYGGSFSGYYWSWIRQPPGKGLEWIGDINHSGNTNFNPSLKSRVTISVDTSKNQFSLKLSSVTAADTAVYYCAKGEAWFDPWGQGIMVTVSS<br>99 | EIVMTQSPATLSVSPGERATLSCRASQSVRSNLDWYQQKPGQAPRLLIYGASTRATGIPARFSGSGSGTEFTLTISSLQSEDFAVYYCQQYNNWPLTFGGGTKVEIK<br>100 | QVQLQQWGAGLLKPSETLSLICAVYGGSFSGYYWSWIRQPPGKGLEWIGDINHSGNTNFNPSLKSRVTISVDTSKNQFSLKLSSVTAADTAVYYCAKGEAWFDPWGQGIMVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPAAASSVFLFPPKPKDTLMISRTPEVTCVVVDVSAEDPEVQFNWYVDGVEVHNAKTKPREEQFNSTFRVVSVLTVVHQDWLNGKEYKCKVSNKGLPSSIEKTISKTKGQPREPQVYTLPPSREEMTKNQVSLTCLVKGFYPSDIAVEWESNGQPENNYKTTPPMLDSDGSFLLYSKLTVDKSRWQQGNVFSCSVMHEALHNHYTQKSLSLSPGK<br>101 | EIVMTQSPATLSVSPGERATLSCRASQSVRSNLDWYQQKPGQAPRLLIYGASTRATGIPARFSGSGSGTEFTLTISSLQSEDFAVYYCQQYNNWPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC<br>102 |
| 4 | C28B105 | IgG1 | — | QVQLQQWGAGLLKPSETLSLTCAVYGGSFSGYYWNWIRQPPGKGLQWIGEINHSGTTNYNPSLKSRVTISVDTSKNQFSLKLSSLTAADTAVYYCARGEAVALYWGQGTLVTVSS<br>133 | EIVMTQSPATLSVSPGERATLSCRASQSVNSNLAWYQQKPGQAPRLLIYGASARATGIPARFSGSGSGTEFTLTISSLQSEDFAVYYCQQYYNWPLTFGGGTKVEIK<br>134 | QVQLQQWGAGLLKPSETLSLTCAVYGGSFSGYYWNWIRQPPGKGLQWIGEINHSGTTNYNPSLKSRVTISVDTSKNQFSLKLSSLTAADTAVYYCARGEAVALYWGQGTLVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPAAASSVFLFPPKPKDTLMISRTPEVTCVVVDVSAEDPEVQFNWYVDGVEVHNAKTKPREEQFNSTFRVVSVLTVVHQDWLNGKEYKCKVSNKGLPSSIEKTISKTKGQPREPQVYTLPPSREEMTKNQVSLTCLVKGFYPSDIAVEWESNGQPENNYKTTPPMLDSDGSFLLYSKLTVDKSRWQQGNVFSCSVMHEALHNHYTQKSLSLSPGK<br>135 | EIVMTQSPATLSVSPGERATLSCRASQSVNSNLAWYQQKPGQAPRLLIYGASARATGIPARFSGSGSGTEFTLTISSLQSEDFAVYYCQQYYNWPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC<br>136 |

TABLE 2

CD28 Antibody Kabat CDR Amino Acid Sequences

| # | Protein Name | HC Kabat CDR1 | HC Kabat CDR2 | HC Kabat CDR3 | LC Kabat CDR1 | LC Kabat CDR2 | LC Kabat CDR3 |
|---|---|---|---|---|---|---|---|
| 1 | C28B11 | SYAMS<br>1 | AISGSGGRTYYADSVKG<br>2 | GAGYWYFDL<br>3 | RASQSVSSYLA<br>4 | DASNRAT<br>5 | QQRSNWPLT<br>6 |
| 2 | C28B19 | SYWMH<br>35 | NIYPGSGRTNYDEKFKS<br>36 | EHYGSNSHPMDY<br>37 | GASENIYGSLN<br>38 | GATNLAD<br>39 | QNLLSTPYT<br>40 |
| 3 | C28B103 | GYYWS<br>69 | DINHSGNTNFNPSLKS<br>70 | GEAWFDP<br>71 | RASQSVRSNLD<br>72 | GASTRAT<br>73 | QQYNNWPLT<br>74 |
| 4 | C28B105 | GYYWN<br>103 | EINHSGTTNYNPSLKS<br>104 | GEAVALY<br>105 | RASQSVNSNLA<br>106 | GASARAT<br>107 | QQYYNWPLT<br>108 |

TABLE 3

CD28 Antibody Chothia CDR Amino Acid Sequences

| # | Protein Name | HC Chothia CDR1 | HC Chothia CDR2 | HC Chothia CDR3 | LC Chothia CDR1 | LC Chothia CDR2 | LC Chothia CDR3 |
|---|---|---|---|---|---|---|---|
| 1 | C28B11 | EFTFTSY 7 | SGSGGR 8 | GAGYWYFD 9 | SQSVSSY 10 | DAS 11 | RSNWPL 12 |
| 2 | C28B19 | GYTFTSY 41 | YPGSGR 42 | EHYGSNSHPMD 43 | SENIYGS 44 | GAT 45 | LLSTPY 46 |
| 3 | C28B103 | GGSFSGY 75 | NHSGN 76 | GEAWFD 77 | SQSVRSN 78 | GAS 79 | YNNWPL 80 |
| 4 | C28B105 | GGSFSGY 109 | NHSGT 110 | GEAVAL 111 | SQSVNSN 112 | GAS 113 | YYNWPL 114 |

TABLE 4

CD28 Antibody AbM CDR Amino Acid Sequences

| # | Protein Name | HC AbM CDR1 | HC AbM CDR2 | HC AbM CDR3 | LC AbM CDR1 | LC AbM CDR2 | LC AbM CDR3 |
|---|---|---|---|---|---|---|---|
| 1 | C28B11 | EFTFTSYAMS 13 | AISGSGGRTY 14 | GAGYWYFDL 15 | RASQSVSSYLA 16 | DASNRAT 17 | QQRSNWPLT 18 |
| 2 | C28B19 | GYTFTSYWMH 47 | NIYPGSGRTN 48 | EHYGSNSHPMDY 49 | GASENIYGSLN 50 | GATNLAD 51 | QNLLSTPYT 52 |
| 3 | C28B103 | GGSFSGYYWS 81 | DINHSGNTN 82 | GEAWFDP 83 | RASQSVRSNLD 84 | GASTRAT 85 | QQYNNWPLT 86 |
| 4 | C28B105 | GGSFSGYYWN 115 | EINHSGTTN 116 | GEAVALY 117 | RASQSVNSNLA 118 | GASARAT 119 | QQYYNWPLT 120 |

TABLE 5

CD28 Antibody Contact CDR Amino Acid Sequences

| # | Protein Name | HC Contact CDR1 | HC Contact CDR2 | HC Contact CDR3 | LC Contact CDR1 | LC Contact CDR2 | LC Contact CDR3 |
|---|---|---|---|---|---|---|---|
| 1 | C28B11 | TSYAMS 19 | WVSAISGSGGRTY 20 | AKGAGYWYFD 21 | SSYLAWY 22 | LLIYDASNRA 23 | QQRSNWPL 24 |
| 2 | C28B19 | TSYWMH 53 | WIGNIYPGSGRTN 54 | TREHYGSNSHPMD 55 | YGSLNWY 56 | LLIYGATNLA 57 | QNLLSTPY 58 |
| 3 | C28B103 | SGYYWS 87 | WIGDINHSGNTN 88 | AKGEAWFD 89 | RSNLDWY 90 | LLIYGASTRA 91 | QQYNNWPL 92 |
| 4 | C28B105 | SGYYWN 121 | WIGEINHSGTTN 122 | ARGEAVAL 123 | NSNLAWY 124 | LLIYGASARA 125 | QQYYNWPL 126 |

TABLE 6

| CD28 Antibody IMGT CDR Amino Acid Sequences | | | | | | | |
|---|---|---|---|---|---|---|---|
| # | Protein Name | HC IMGT CDR1 | HC IMGT CDR2 | HC IMGT CDR3 | LC IMGTC DR1 | LC IMGT CDR2 | LC IMGT CDR3 |
| 1 | C28B11 | EFTFTSYA 25 | ISGSGGRT 26 | AKGAGYWYFDL 27 | QSVSSY 28 | DAS 29 | QQRSNWPLT 30 |
| 2 | C28B19 | GYTFTSYW 59 | IYPGSGRT 60 | TREHYGSNSHPMDY 61 | ENIYGS 62 | GAT 63 | QNLLSTPYT 64 |
| 3 | C28B103 | GGSFSGYY 93 | INHSGNT 94 | AKGEAWFDP 95 | QSVRSN 96 | GAS 97 | QQYNNWPLT 98 |
| 4 | C28B105 | GGSFSGYY 127 | INHSGTT 128 | ARGEAVALY 129 | QSVNSN 130 | GAS 131 | QQYYNWPLT 132 |

Example 2: Anti-Vβ17/Anti-BCMA/Anti-CD28 Trispecific Antibody Production

The variable region sequence of anti-Vβ17, anti-CD28 and anti-BCMA antibodies were used to generate a trispecific human IgG1 antibody to be tested for T cell re-directed killing of H929 cells.

The trispecific antibodies were produced as Fab (CD28) x scFv (Vβ17) x scFv (BCMA) antibodies in the knob-into-hole format as human IgG1 with silent Fc. Nucleic acid sequences encoding variable regions were sub-cloned into a custom mammalian expression vectors containing constant region of human IgG1 expression cassettes using standard PCR restriction enzyme based standard cloning techniques, and sequences verified. The bispecific antibodies were expressed by transient transfection in Chinese hamster ovary cell line. The antibodies were initially purified by MABSELECT SURE Protein A column (GE Healthcare). The column was equilibrated with PBS pH 7.2 and loaded with fermentation supernatant at a flow rate of 2 mL/min. After loading, the column was washed with 4 column volumes of PBS followed by elution in 30 mM sodium acetate, pH 3.5. Fractions containing protein peaks as monitored by absorbance at 280 nm were pooled and neutralized to pH 5.0 by adding 1% 3 M sodium acetate pH 9.0. The bispecific mAbs were further purified on a preparative SUPERDEX 200 10/300 GL (GE healthcare) size exclusion chromatography (SEC) column equilibrated with PBS buffer. The integrity of sample was assessed by endotoxin measurement (<3.0 EU/mg), SDS-PAGE under reducing and non-reducing conditions, SEC, and intact mass by MS.

The design of the trispecific antibodies is shown in Table 7 below.

TABLE 7

Design of the trispecific antibodies

| # | Name | Chain A description N-term (Fab) | Chain A description C-term | Chain B description N-term (Fab) | Chain B description C-term | Molecule Description |
|---|---|---|---|---|---|---|
| 1 | VB28B1 | C28B11 | B17B21 | C28B11 | BCMB519 | C28B11 × B17B21 × BCMB519 |
| 2 | VB28B2 | C28B19 | B17B21 | C28B19 | BCMB519 | C28B19 × B17B21 × BCMB519 |
| 3 | VB28B3 | C28B103 | B17B21 | C28B103 | BCMB519 | C28B103 × B17B21 × BCMB519 |
| 4 | VB28B4 | C28B105 | B17B21 | C28B105 | BCMB519 | C28B105 × B17B21 × BCMB519 |
| 5 | VB28B5 | B21M | B17B21 | B21M | BCMB519 | B21M × B17B21 × BCMB519 |
| 6 | VB28B6 | C28B11 | Null | C28B11 | BCMB519 | C28B11 × Null × BCMB519 |
| 7 | VB28B7 | C28B19 | Null | C28B19 | BCMB519 | C28B19 × Null × BCMB519 |
| 8 | VB28B8 | C28B103 | Null | C28B103 | BCMB519 | C28B103 × Null × BCMB519 |
| 9 | VB28B9 | C28B105 | Null | C28B105 | BCMB519 | C28B105 × Null × BCMB519 |
| 10 | VB28B10 | B21M | Null | B21M | BCMB519 | B21M × Null × BCMB519 |

Figure 1:
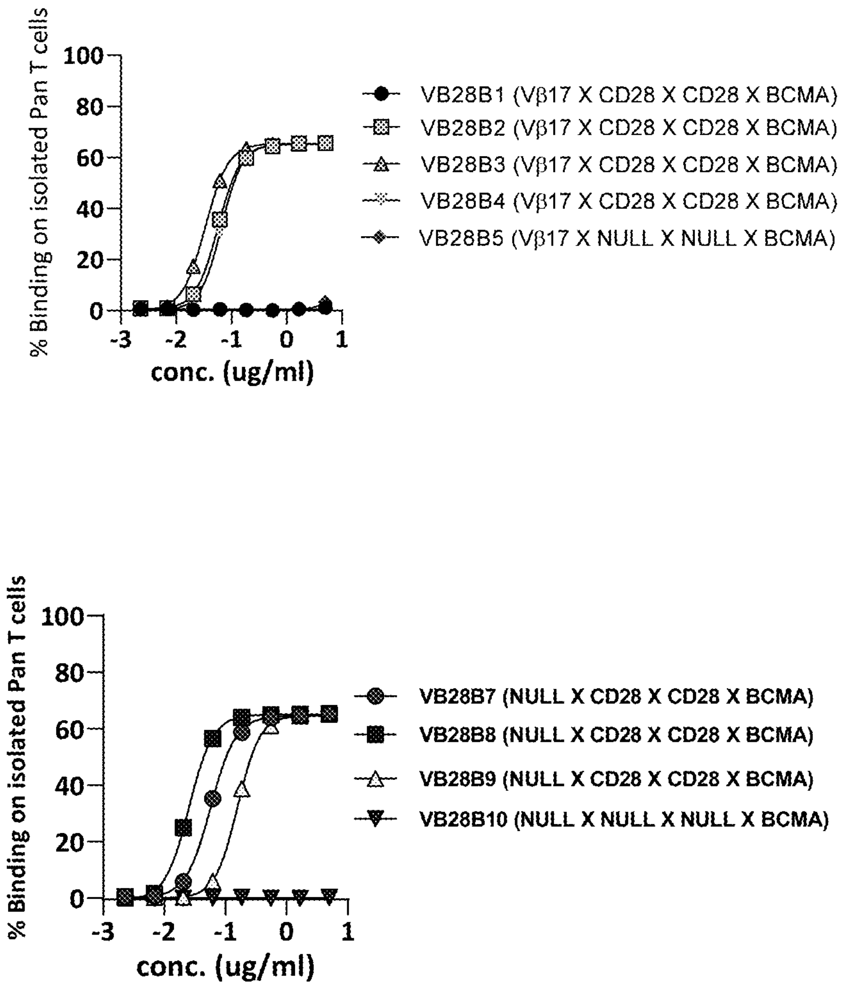
FIG. 1 shows that anti-Vβ17/anti-BCMA/anti-CD28 trispecific antibodies show potent binding on Pan T cells. Antibodies with C28B19, C28B103 and C28B105 clones showed robust binding to Pan T cells in a dose dependent manner.

Example 3: Anti-Vβ17/Anti-BCMA/Anti-CD28 Trispecific Antibodies Show Potent Binding on Pan T Cells To test the engagement of CD28 on Vβ17 T cells, Pan T cells were isolated from human PBMCs and tested for binding with the Vβ17×CD28×BCMA antibodies containing various CD28 binders. Antibodies with C28B19, C28B103 and C28B105 clones showed robust binding to pan T cells in a dose dependent manner. See FIG. 1 and Table 8. EC50 values for binding were determined to be 0.06 μg/ml, 0.03 μg/ml and 0.06 μg/ml respectively for C28B19, C28B103 and C28B105. Antibody with C28B11 clone was observed to be a poor binder for CD28 and showed binding to only 5% of pan T cells because of the Vβ17 binding arm. Vβ17×BCMA antibody also showed binding to 5% of pan T cells only which was also the frequency of Vβ17 T cells in the tested donors. Binding to pan T cells was dependent on the CD28 arm of the trispecific antibody as the EC50 values for binding of trispecific antibodies lacking the Vβ17 arm was similar to the full trispecific antibody. No binding was observed in antibodies lacking the Vβ17 and CD28 binding arms.

TABLE 8

| Cell binding to Pan T cells | | |
|---|---|---|
| Name | hIgG1 AAS format | $EC_{50}$ (μg/ml) |
| VB28B1 | Vb17 × CD28 × CD28 × BCMA | No binding |
| VB28B2 | Vb17 × CD28 × CD28 × BCMA | 0.06 |
| VB28B3 | Vb17 × CD28 × CD28 × BCMA | 0.03 |
| VB28B4 | Vb17 × CD28 × CD28 × BCMA | 0.06 |
| VB28B5 | Vb17 × null × null × BCMA | Binding only observed to Vb17 + T cells |
| VB28B6 | Null × CD28 × CD28 × BCMA | NA |
| VB28B7 | Null × CD28 × CD28 × BCMA | 0.06 |
| VB28B8 | Null × CD28 × CD28 × BCMA | 0.02 |
| VB28B9 | Null × CD28 × CD28 × BCMA | 0.15 |
| VB28B10 | Null × Null × BCMA | No binding |

Example 4: Anti-Vβ17/Anti-BCMA/Anti-CD28 Trispecific Antibodies Show Potent Binding on H929 Cells Using BCMA and CD28

Figure 2:
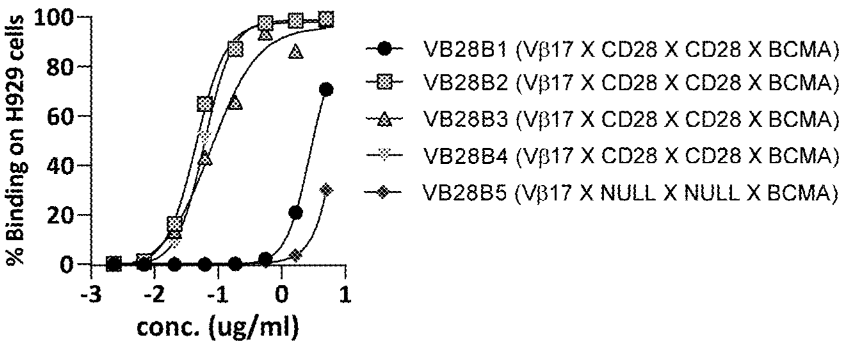
FIG. 2 shows that anti-Vβ17/anti-BCMA/anti-CD28 trispecific antibodies show potent binding on H929 cells using BCMA and CD28. Vβ17×CD28×BCMA trispecific antibodies showed potent binding to H929 cells in a CD28 and BCMA dependent manner.
Figure 2:
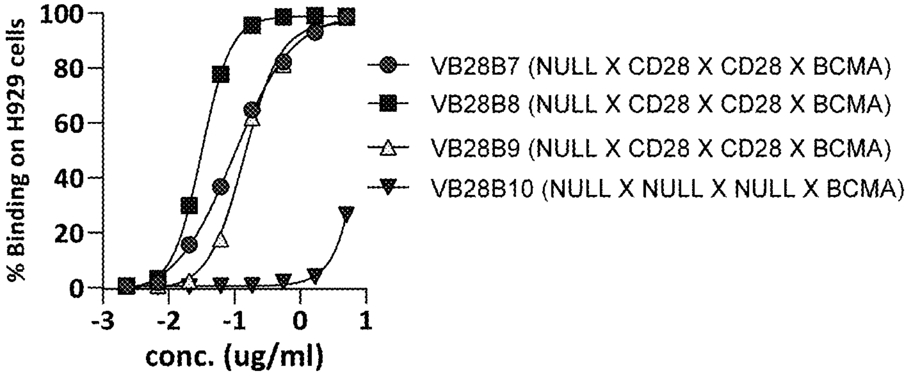

Abc. H929 cells were observed to express CD28 (data not shown). This is in line with multiple myeloma cells expressing CD28. Vβ17×CD28×BCMA trispecific antibodies showed potent binding to H929 cells in a CD28 and BCMA dependent manner. See FIG. 2 and Table 9. EC50 values for binding were determined to be 0.10 μg/ml, 0.03 μg/ml and 0.14 μg/ml for trispecific antibodies with C28B19, C28B103 and C28B105 clones respectively. Binding of the trispecific antibodies was largely dependent upon CD28 arm as a potent decrease in binding was observed in absence of CD28 arm (EC50 >5 μg/ml). VB28B1 antibody with C28B11 clone showed poorer binding on H929 cells also as compared to the other antibodies because of the weak affinity of the C28B11 clone.

TABLE 9

| Cell binding to BCMA expressing H929 cell line | | |
|---|---|---|
| Name | hIgG1 AAS format | $EC_{50}$ (μg/ml) |
| VB28B1 | Vb17 × CD28 × CD28 × BCMA | >5 |
| VB28B2 | Vb17 × CD28 × CD28 × BCMA | 0.04 |

TABLE 9-continued

| Cell binding to BCMA expressing H929 cell line | | |
|---|---|---|
| Name | hIgG1 AAS format | $EC_{50}$ (μg/ml) |
| VB28B3 | Vb17 × CD28 × CD28 × BCMA | 0.08 |
| VB28B4 | Vb17 × CD28 × CD28 × BCMA | 0.06 |
| VB28B5 | Vb17 × null × null × BCMA | >5 |
| VB28B6 | Null × CD28 × CD28 × BCMA | NA |
| VB28B7 | Null × CD28 × CD28 × BCMA | 0.10 |
| VB28B8 | Null × CD28 × CD28 × BCMA | 0.03 |
| VB28B9 | Null × CD28 × CD28 × BCMA | 0.14 |
| VB28B10 | Null × Null × BCMA | >5 |

Figure 3A:
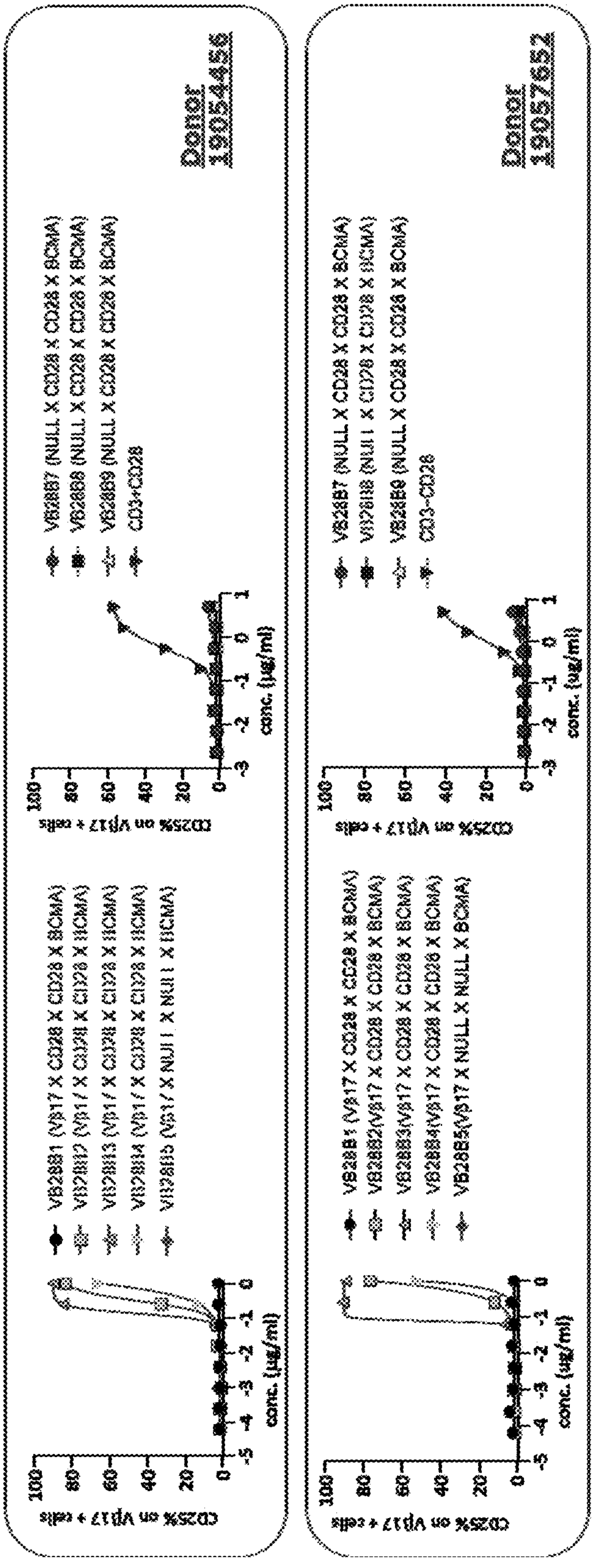
FIGS. 3A-3C show engagement of CD28 potently enhances the activation of Vβ17 T cells in plate bound agonism assay.
Figure 3B:
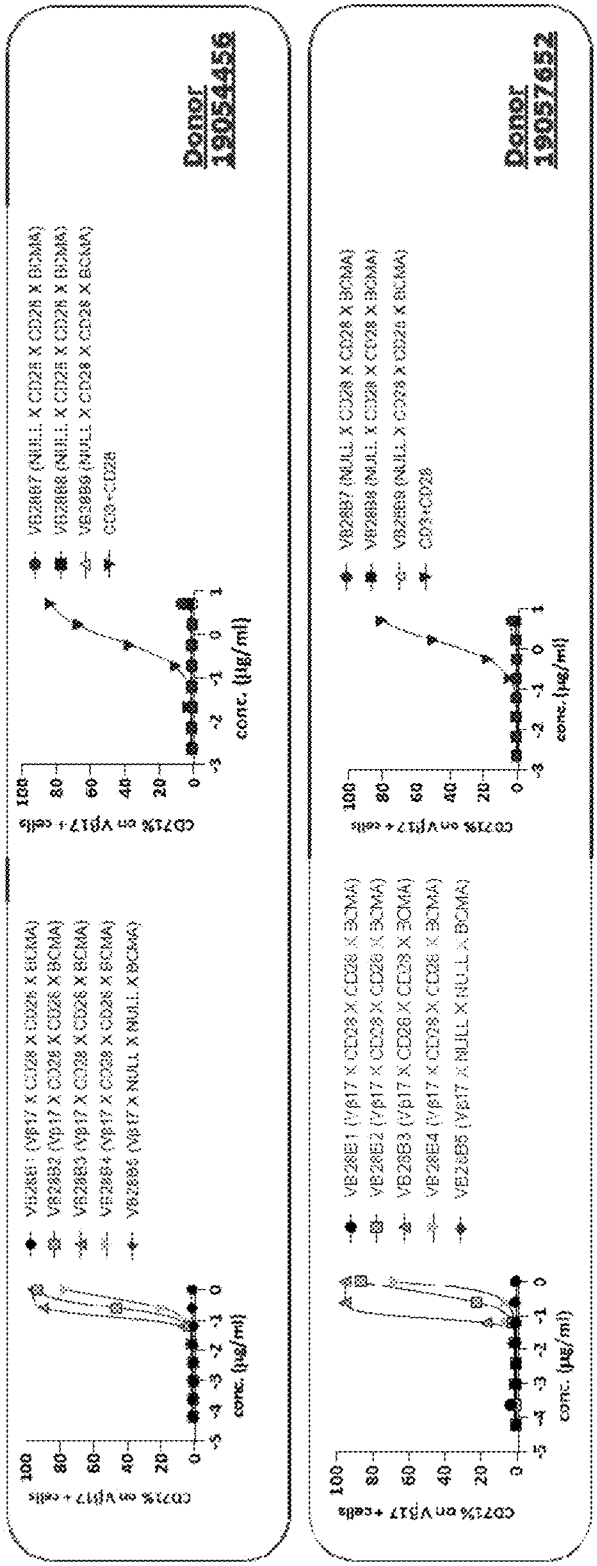
Figure 3C:
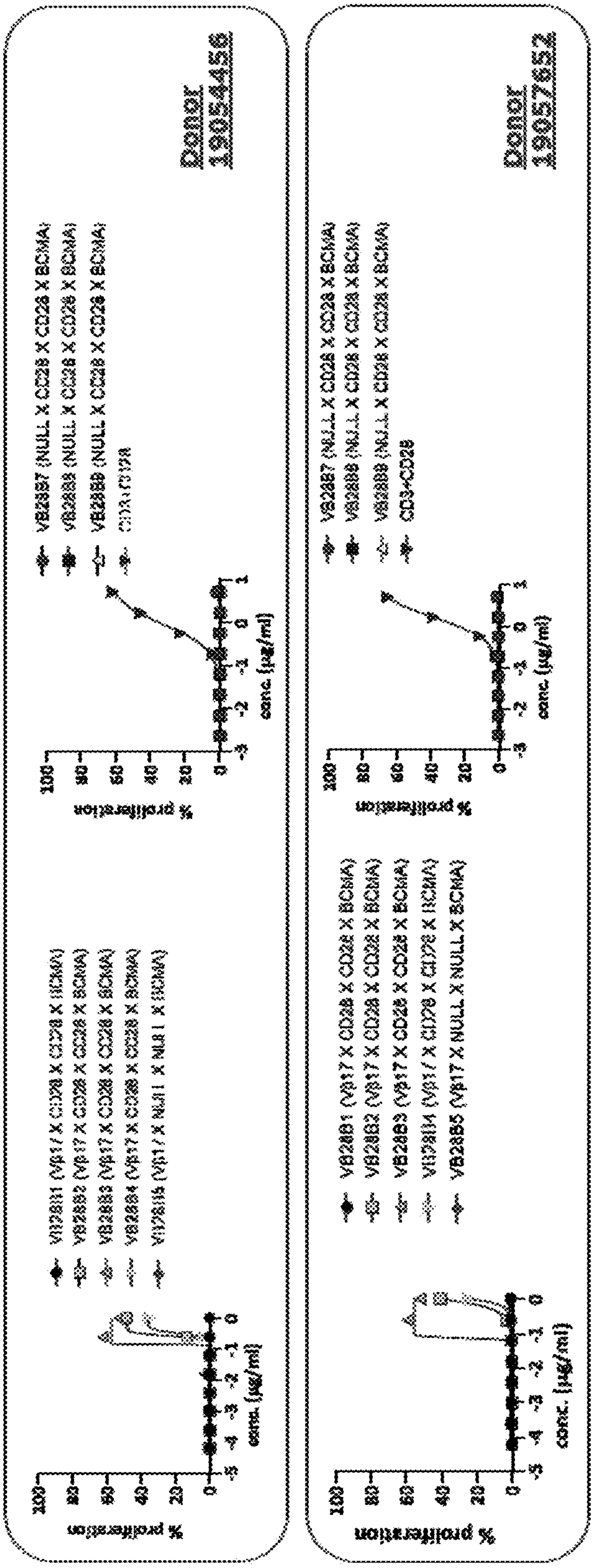

Example 5: Engagement of CD28 Potently Enhances the Activation of Vβ17 T Cells in Plate Bound Agonism Assay To specifically examine the effect of CD28 stimulation on Vβ17 T cells, pan T cells were cultured on plates coated with Vβ17×CD28×BCMA or null×CD28×BCMA antibodies for 96 hours. At the end of the culture period activation of Vβ17 T cells was checked using CD25 (FIG. 3A), CD71 (FIG. 3B) and proliferation (FIG. 3C). VB28B2, VB28B3 and VB28B4 antibodies showed a strong enhancement of Vβ17 T cell activation as indicated by the upregulation of CD25 and CD71 expression on Vβ17 T cells and an increase in the proliferation of Vβ17 T cells. VB28B1 antibody did not show activation of Vβ17 T cells which was in line with the poor binding observed with this antibody. Activation with VB28B3 (clone C28B103) was observed to be the strongest. No increase in activation was observed with CD28 engagement in the absence of Vβ17 arm. As expected stimulation with CD3 and CD28 combination resulted in the activation of Vβ17 T cells. Overall CD28 costimulation resulted in robust enhancement of Vβ17 T cell activation and this was independent of the CD28 expression on target cells.

Figure 4A:
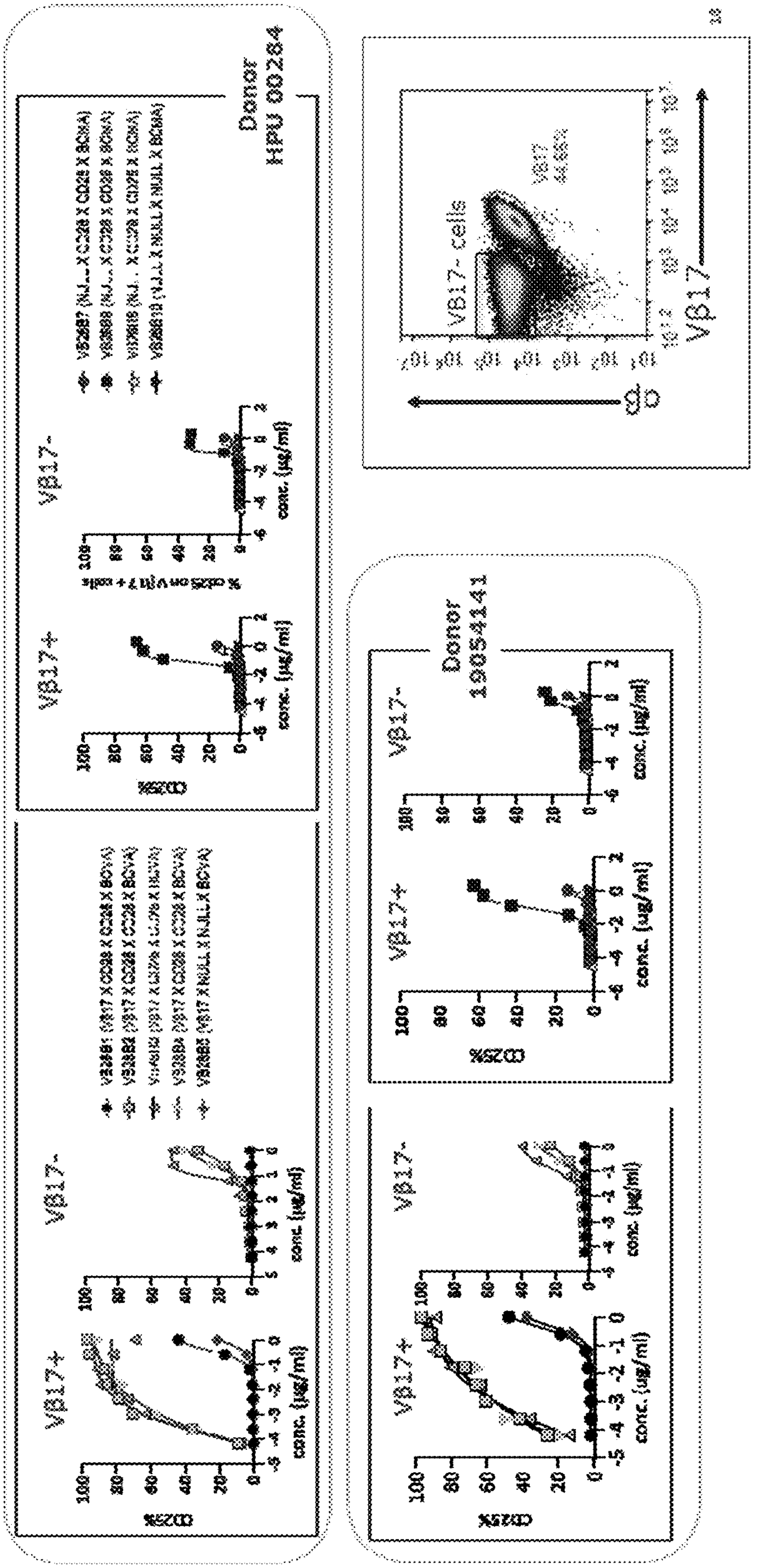
FIGS. 4A-4G show engagement of CD28 potently enhances the activation of Vβ17 T cells in the presence of H929 cells.
Figure 4B:
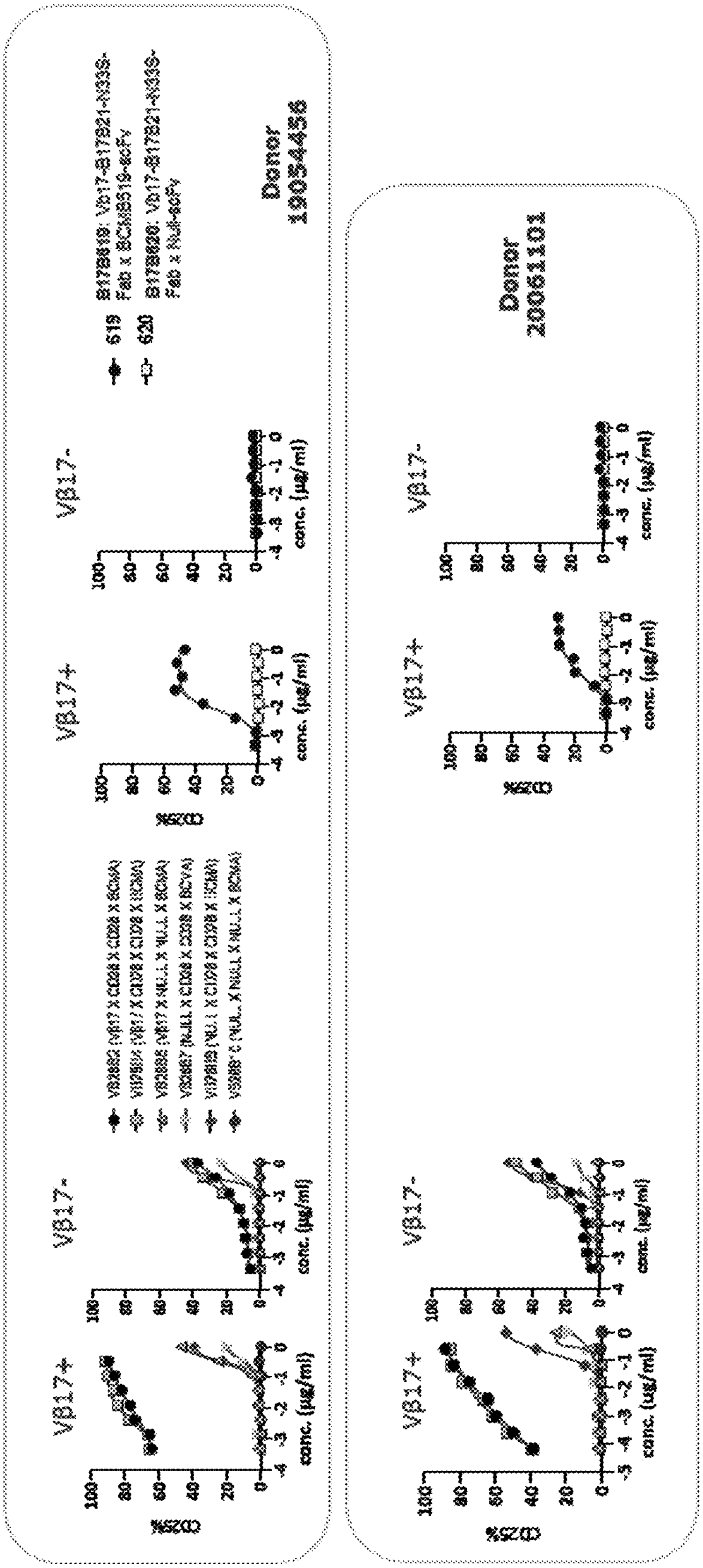
Figure 4C:
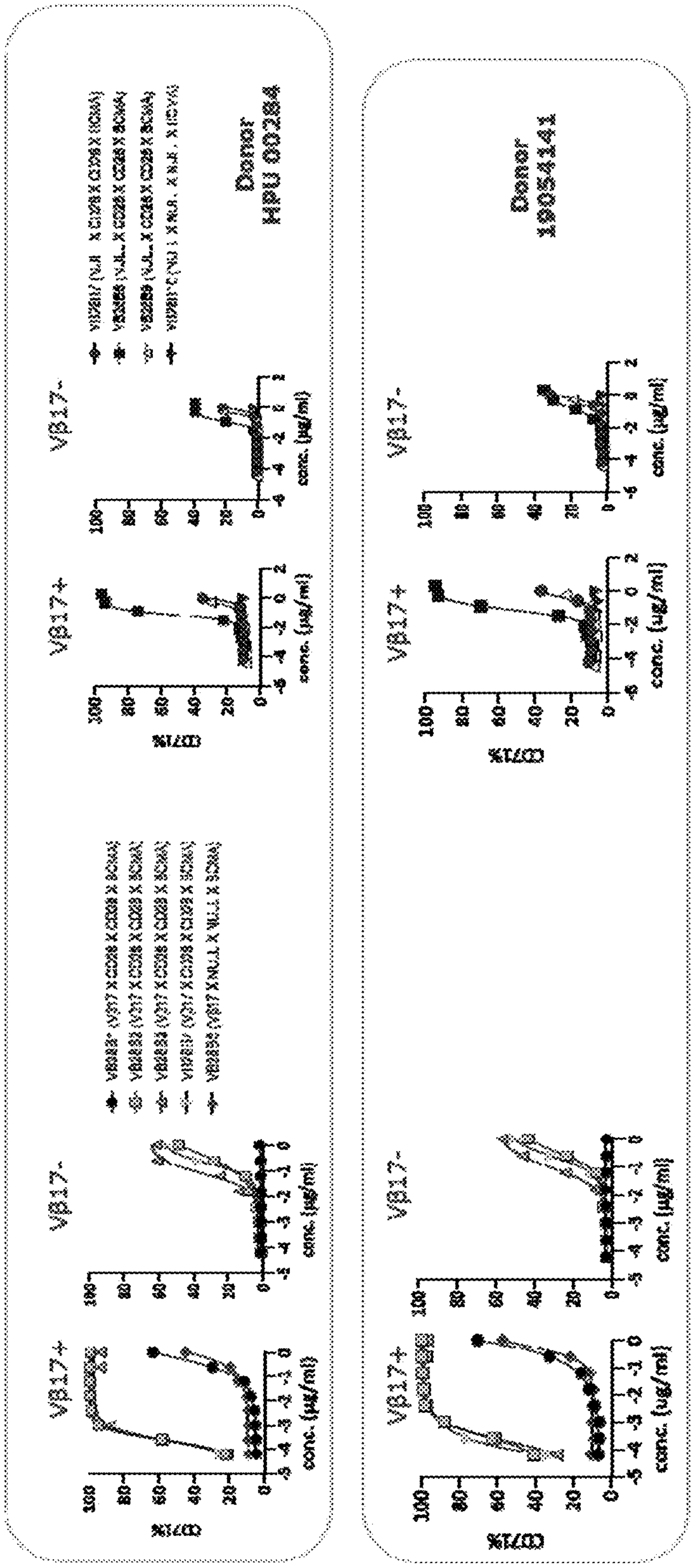
Figure 4D:
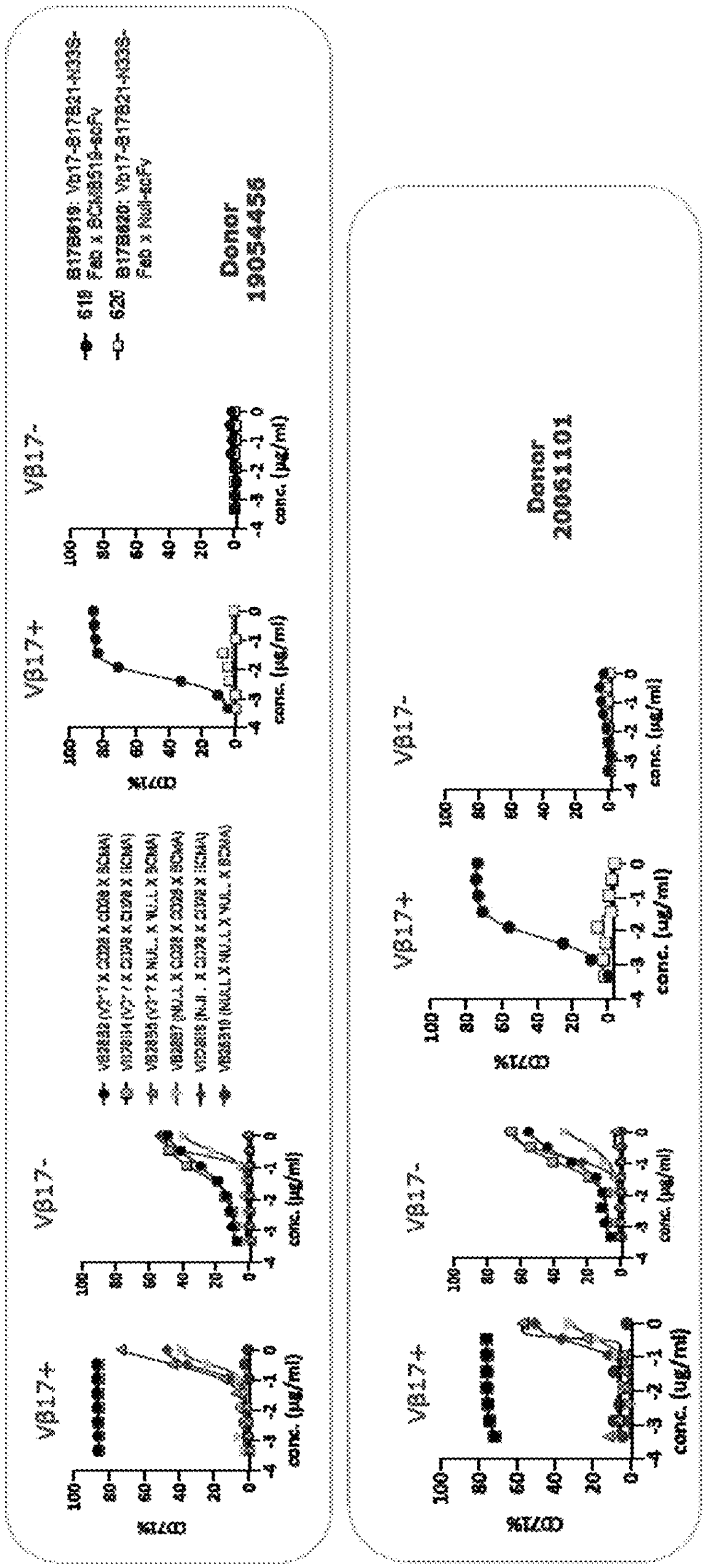
Figure 4E:
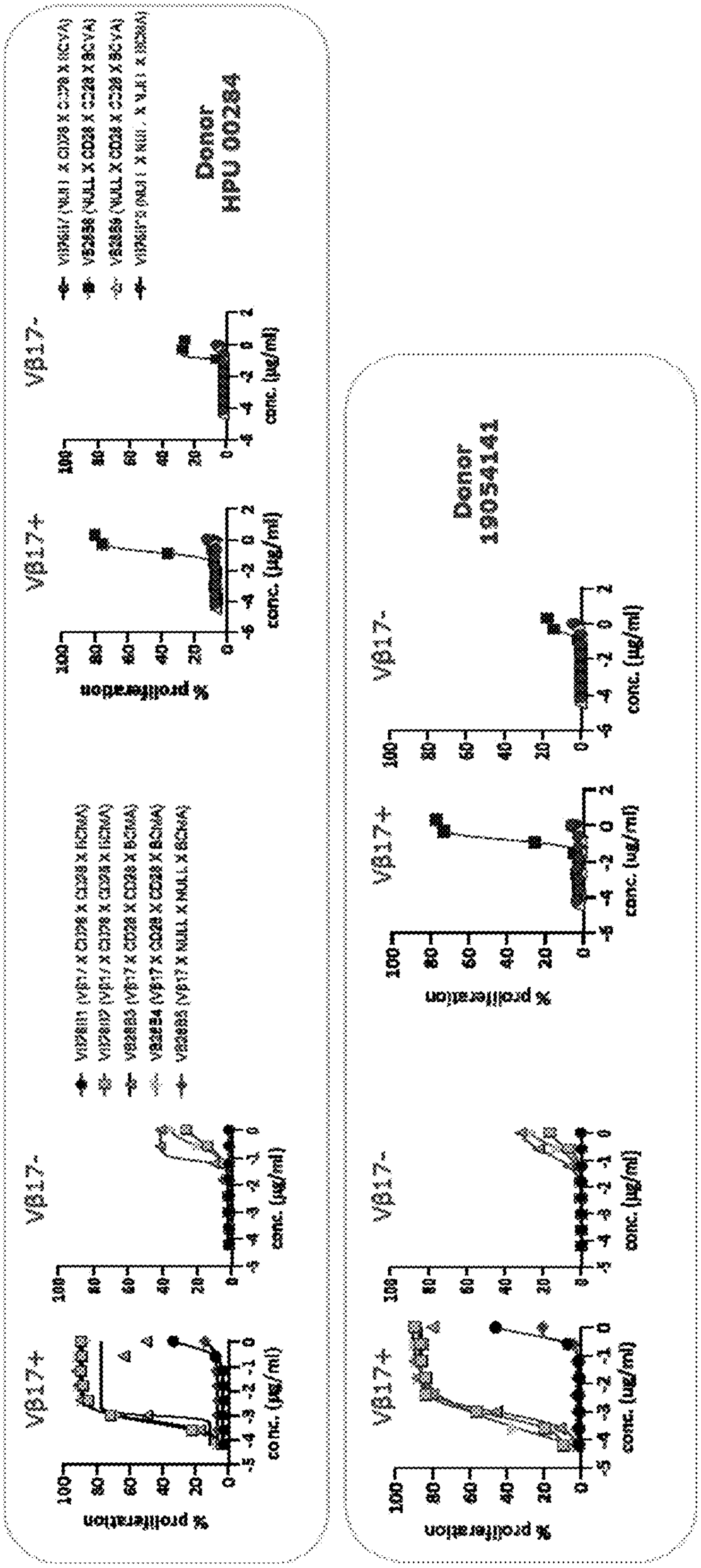
Figure 4F:
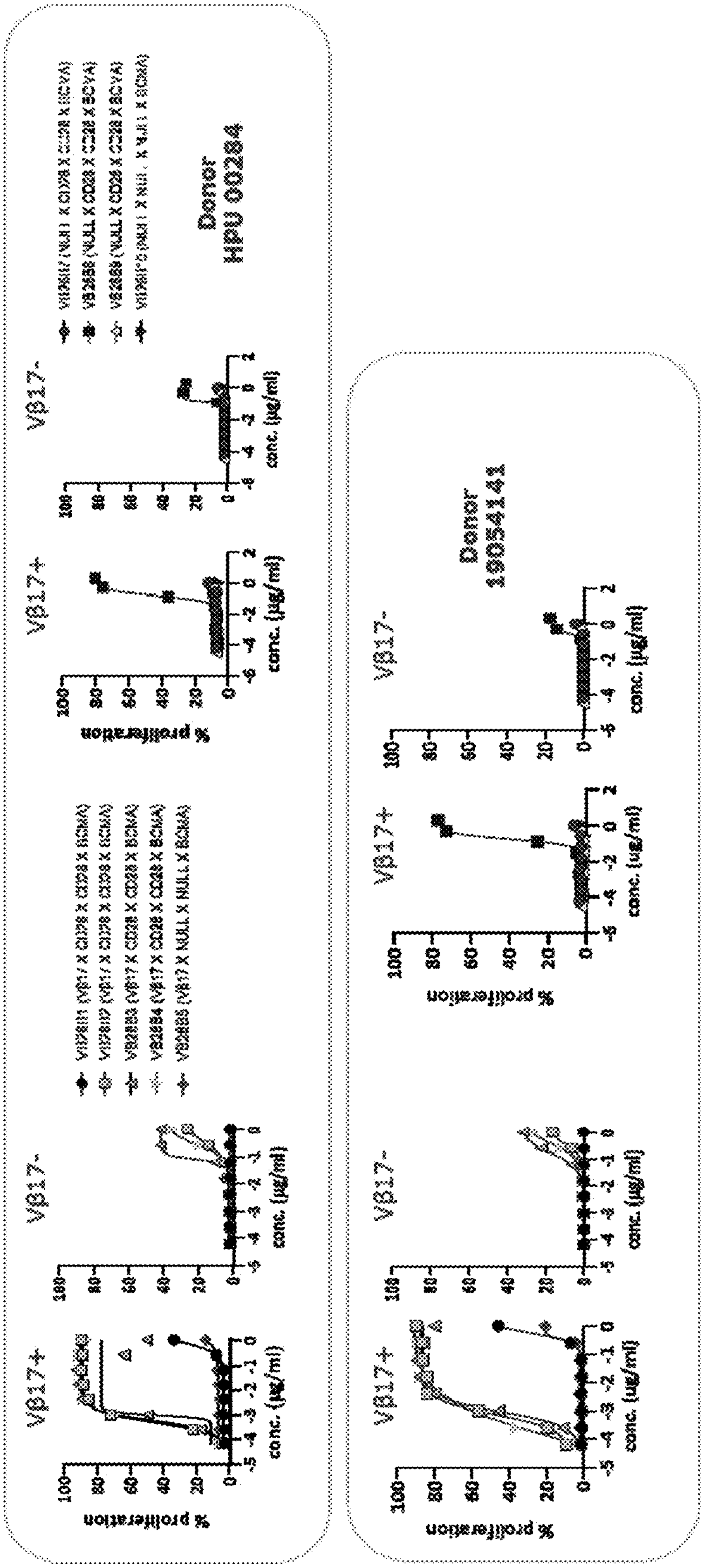
Figure 4G:
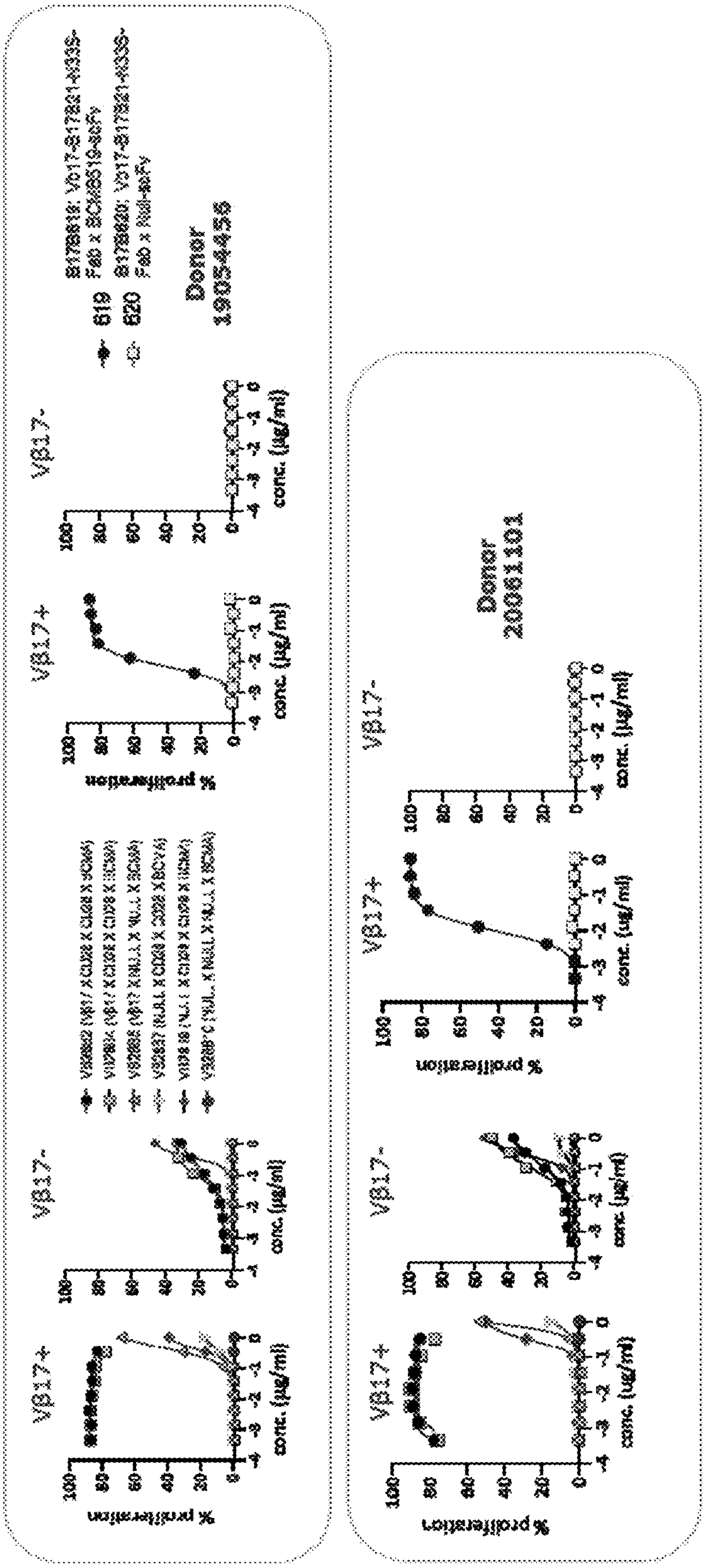

Example 6: Engagement of CD28 Potently Enhances the Activation of Vβ17 T Cells in the Presence of H929 Cells To investigate the effect of CD28 stimulation on Vβ17 T cells and the result of CD28 engagement on H929 cells, pan T cells were cultured with H929 cells at a 1:1 ET ratio of Vβ17 to H929 cells in the presence of the antibodies for 96 hours. Activation of Vβ17 T cells was observed in a dose dependent manner with the addition of Vβ17×BCMA antibody as indicated by the upregulation of CD25 (FIGS. 4A and 4B) and CD71 (FIGS. 4C and 4D) on Vβ17 T cells and an increase in the proliferation of Vβ17 T cells (FIGS. 4E, 4F and 4G). Two formats of Vβ17×BCMA antibodies were tested and activation with B17B619 antibody (Vβ17-Fab X BCMA-ScFv) was observed to stronger than the activation induced by VB28B5 antibody. Importantly the activation induced by Vβ17×CD28×BCMA antibodies was enhanced almost 100-fold as compared to the activation by Vβ17×BCMA antibody. This was true for VB28B2, VB28B3 and VB28B4 antibodies. VB28B1 antibody as before did not show any increase in the activation. Activation of Vβ17 negative T cells with the trispecific antibodies was also observed albeit at much lower levels than the Vβ17+ cells. Strong dose dependent activation of Vβ17+ cells was also observed with Null×CD28×BCMA antibody with the C28B103 binder indicating the agonistic activity of this CD28 clone. Interestingly activation of the Vβ17− cells with this clone of the null×CD28×BCMA antibody was lower than that of the Vβ17+ cells suggesting that Vβ17+ T cells may be inherently more activated than Vβ17− T cells. Among the other two CD28 binders, CD28B19 containing antibody VB28B2 and its VB17 null control VB28B7 was observed to be the best for inducing specific activation of Vβ17 T cells only. Vβ17×BCMA antibody as expected did not show any activation of Vβ17− T cells.

Example 7: Engagement of CD28 does not Induce Exhaustion of Vβ17 T Cells

Figure 5A:
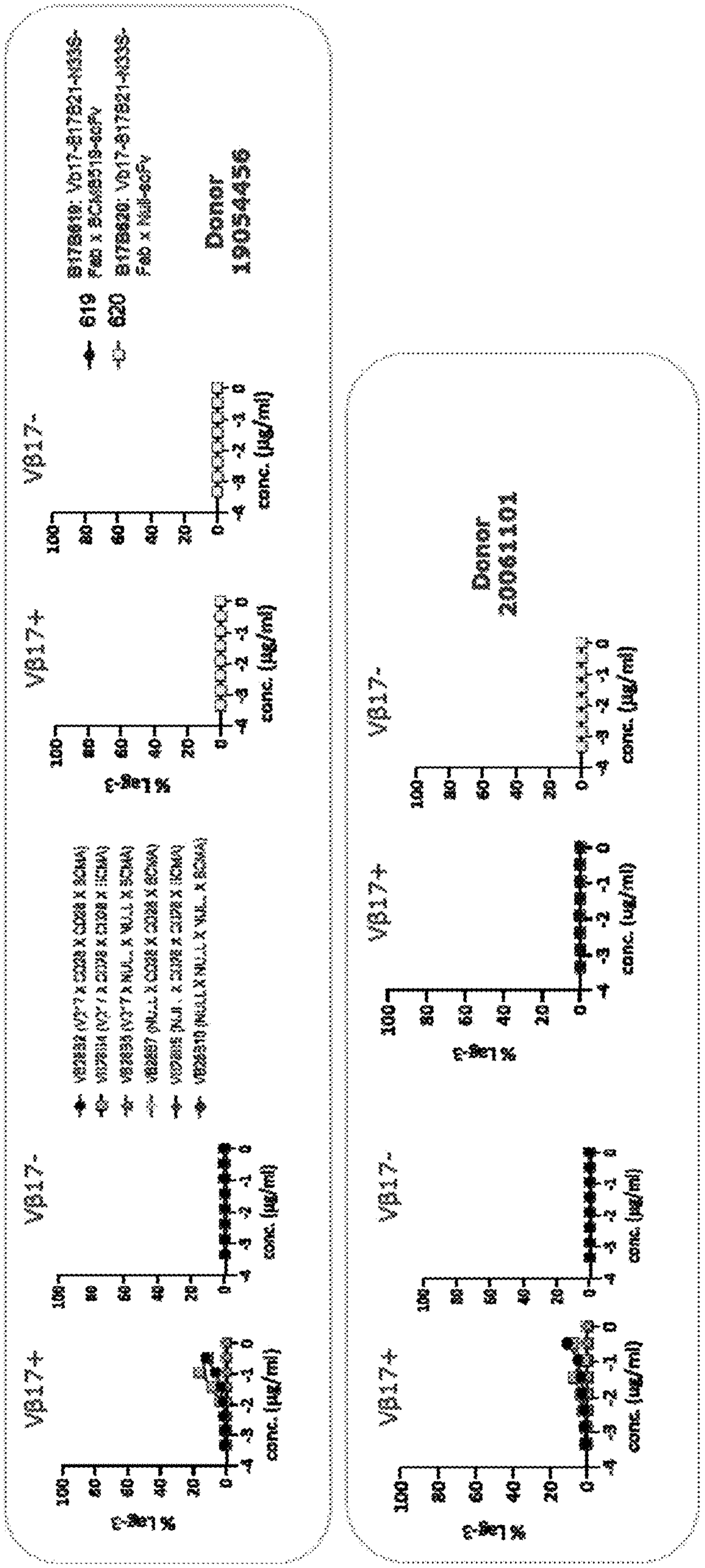
FIGS. 5A-5C show engagement of CD28 does not induce exhaustion of Vβ17 T cells.
Figure 5B:
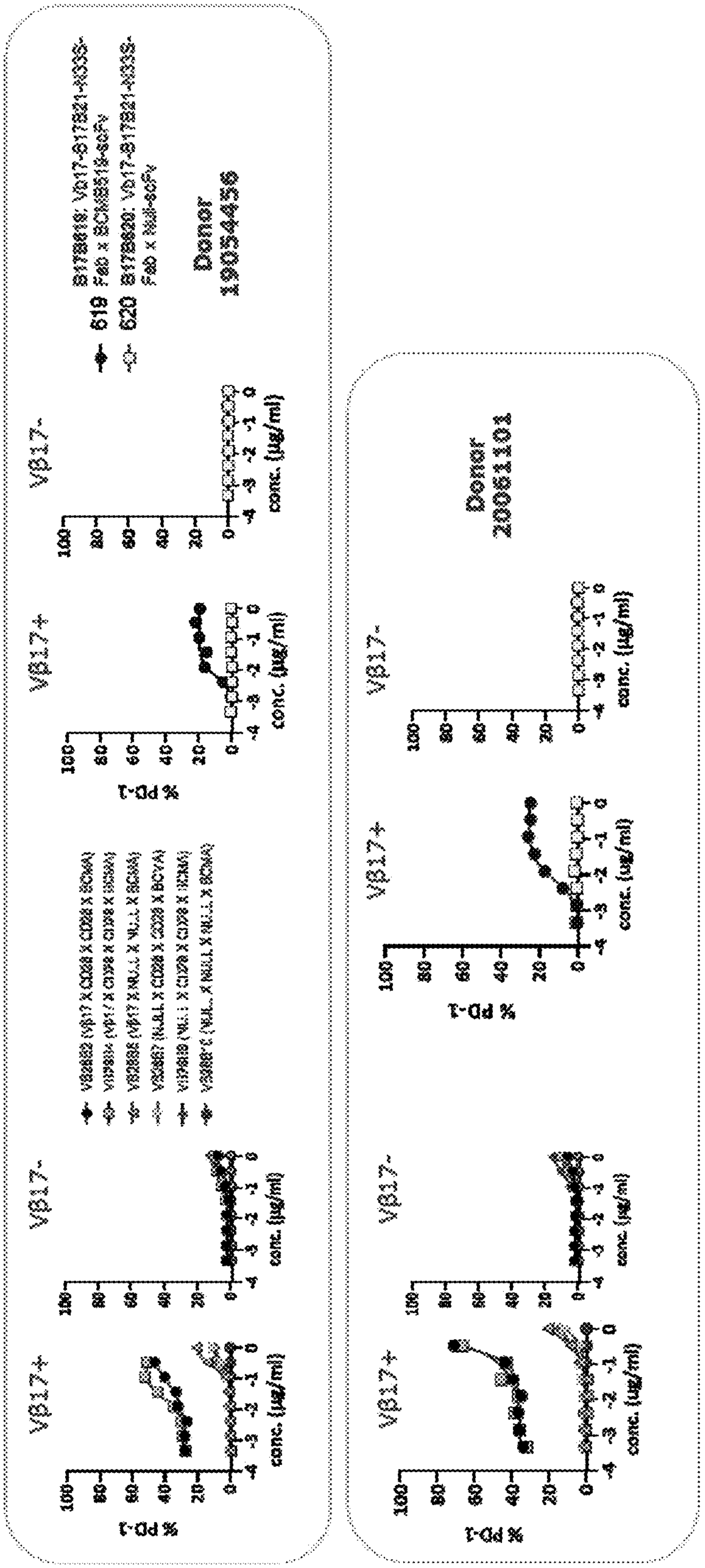
Figure 5C:
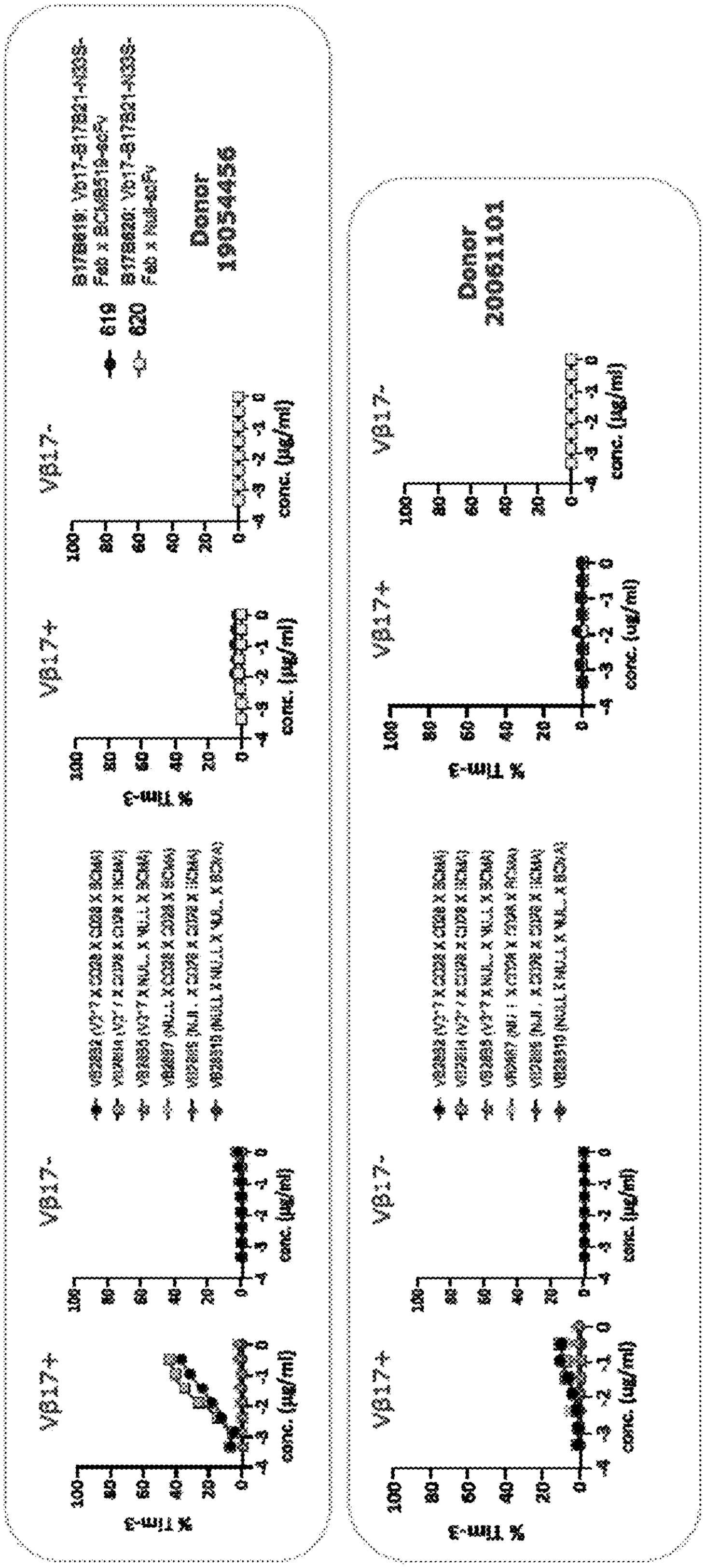

To test whether the increased activation induced by the engagement of CD28 on T cells would result in higher exhaustion of the Vβ17 T cells, pan T cells were cocultured with H929 cells in the presence of the Vβ17×CD28×BCMA antibodies or Vβ17×BCMA antibodies and their Null arm controls. To identify exhausted cells, TIM3, LAG3 and PD1 markers were used although PD1 upregulation is also a sign of T cell activation. PD1 was found to be upregulated on Vβ17+ T cells in the presence of both the Vβ17×BCMA antibodies and the Vβ17×CD28×BCMA antibodies (See FIG. 5B). As was observed with the activation markers, percentage of PD1+VB17 T cells was higher with Vβ17×CD28×BCMA antibodies as compared to Vβ17×BCMA antibody. LAG3 and TIM3 were observed to be induced only on a small fraction of the Vβ17 T cells and no upregulation was seen on the Vβ17− T cells (See FIGS. 5A and 5C). Overall, only 20% of the Vβ17 T cells were found to express TIM3 and LAG3.

Figure 6A:
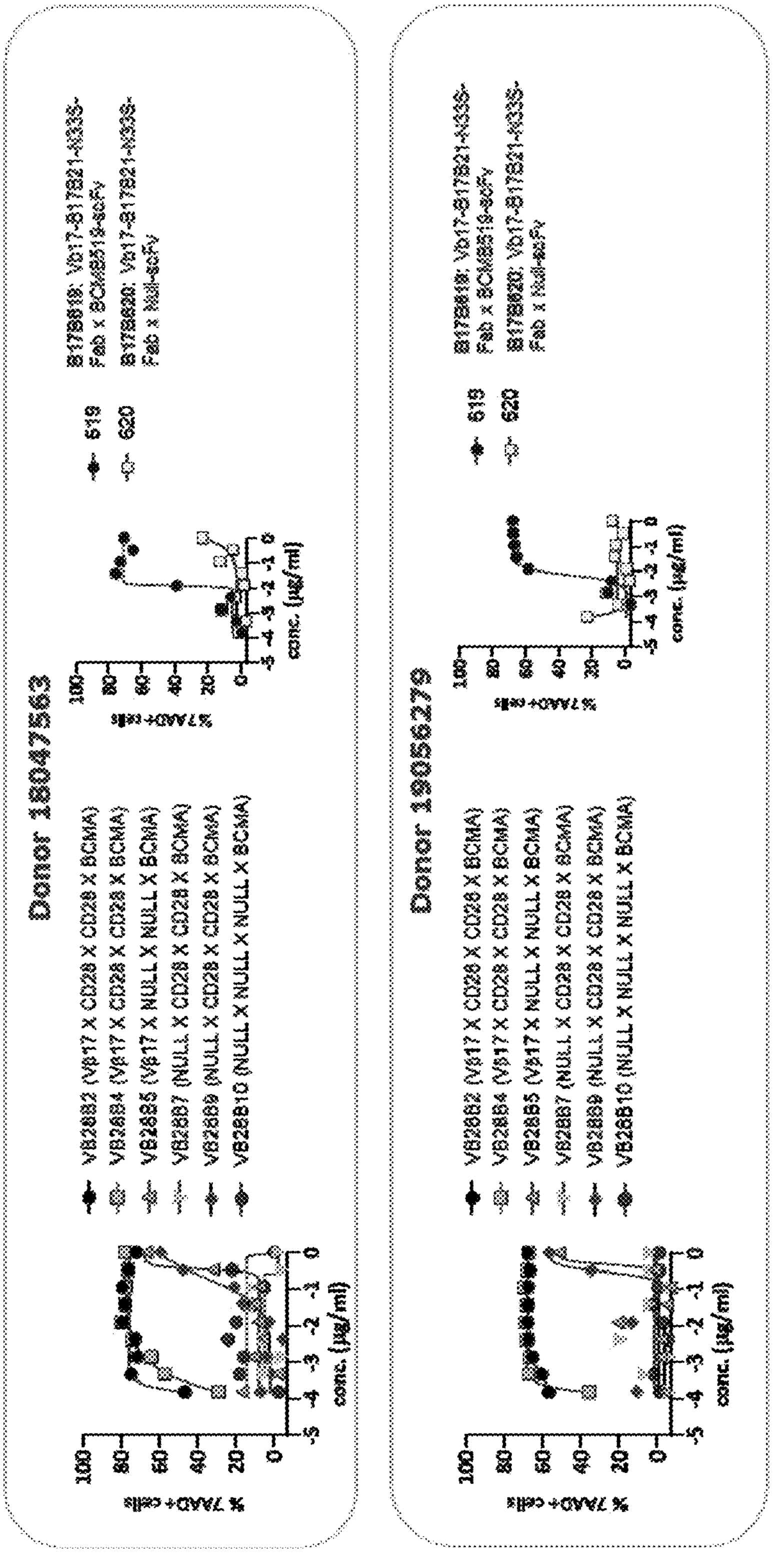
FIGS. 6A-6C show engagement of CD28 potently enhances the cytotoxicity induced by Vβ17 T cells.
Figure 6B:
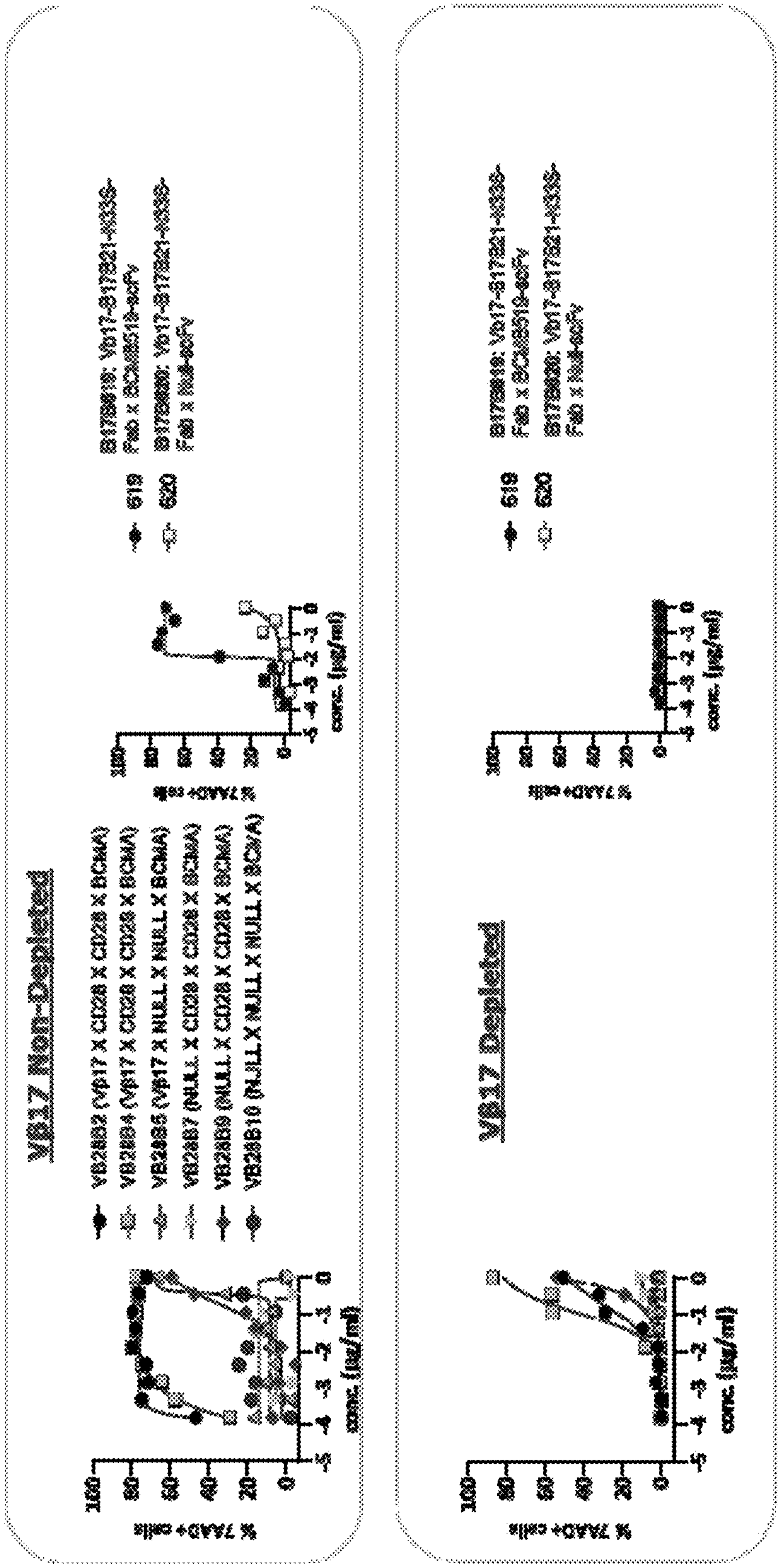
Figure 6C:
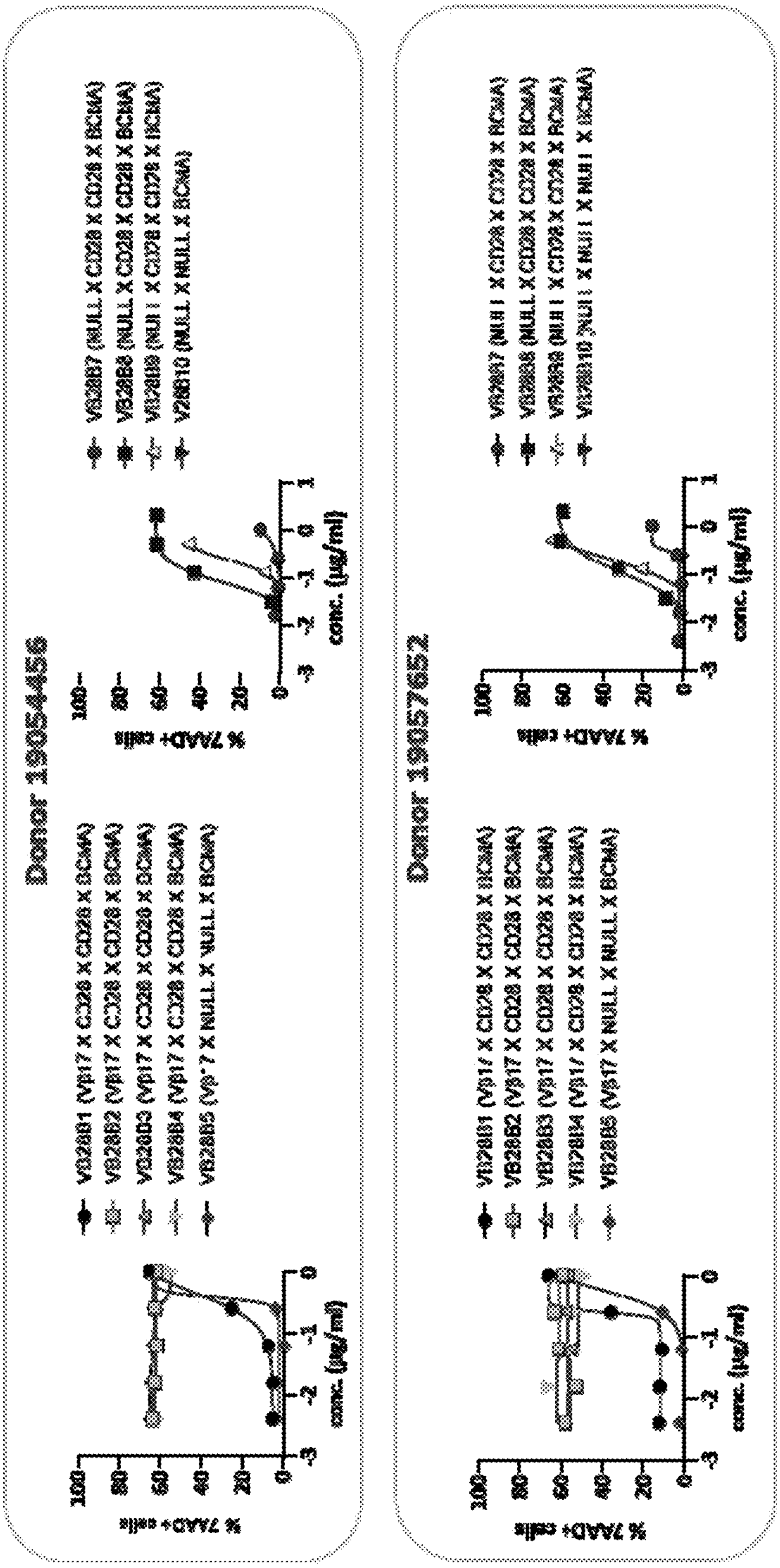
Figure 7A:
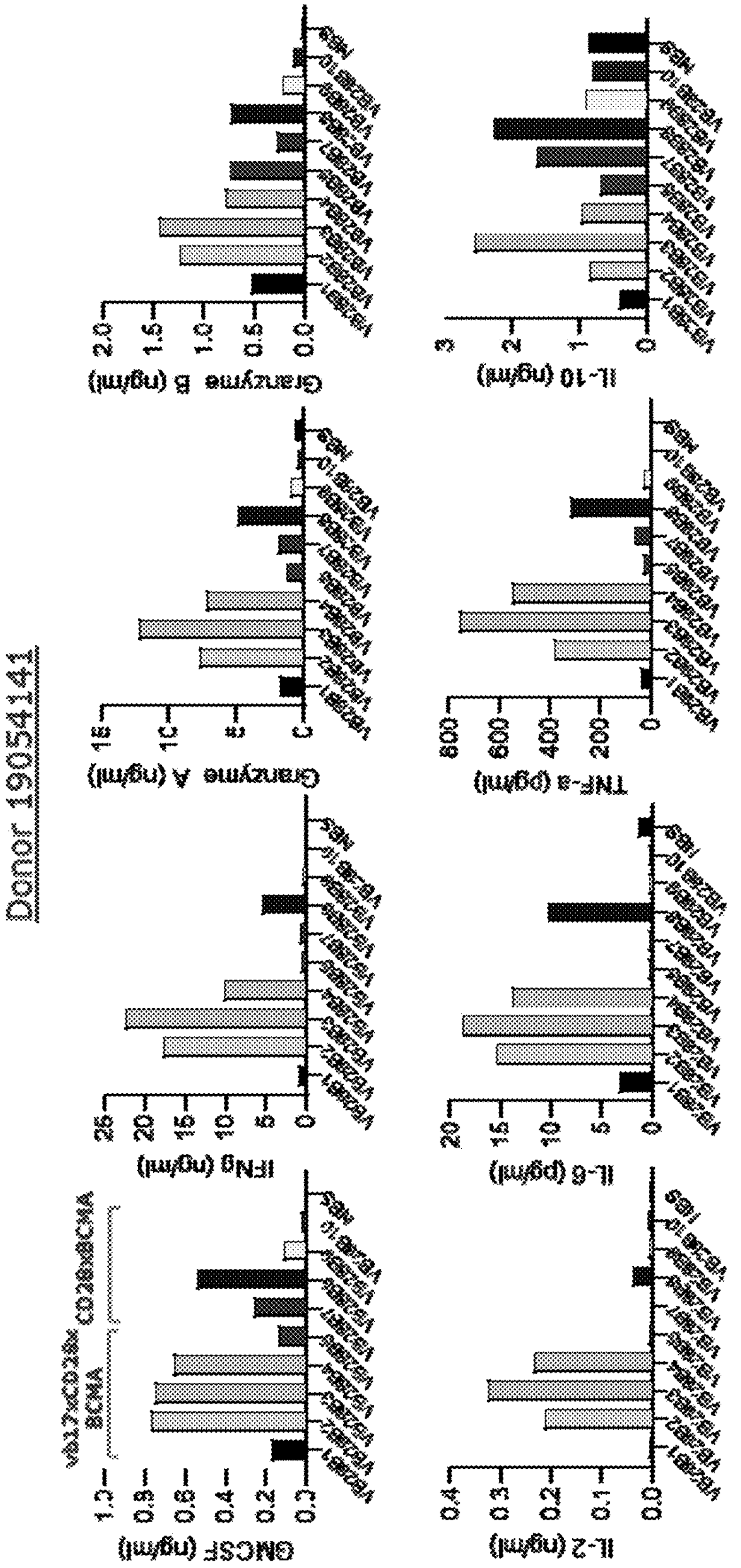
FIGS. 7A-7D show engagement of CD28 potently enhances the cytokine secretion.
Figure 7B:
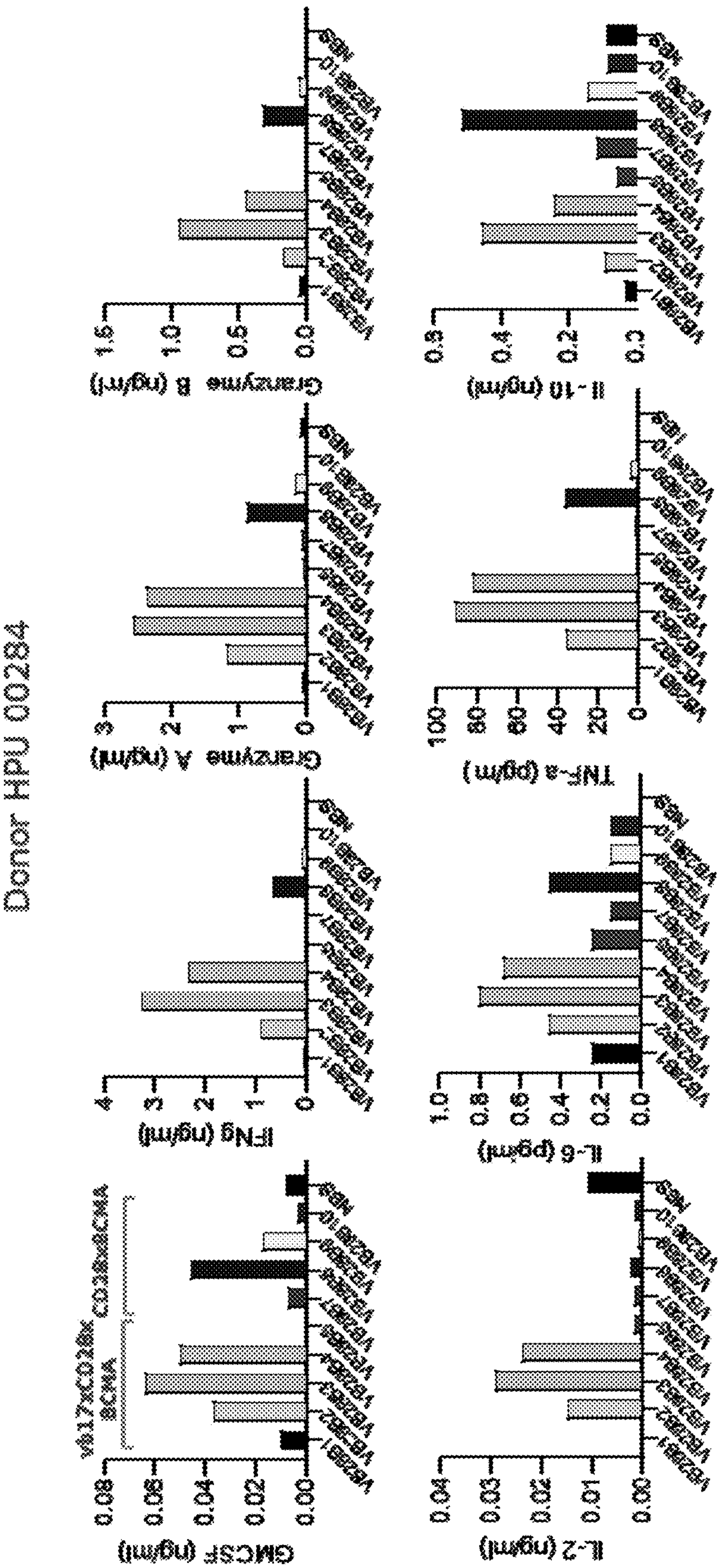
Figure 7C:
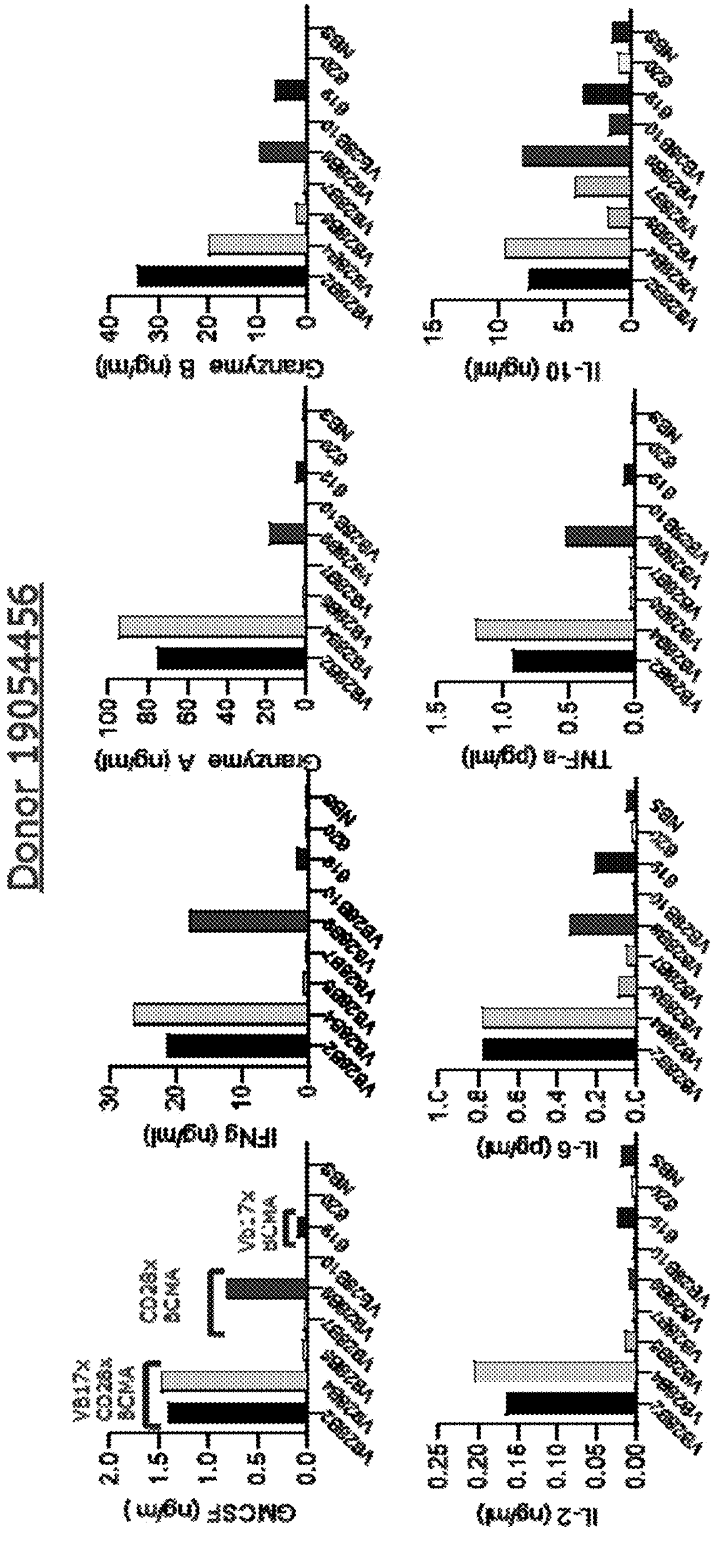
Figure 7D:
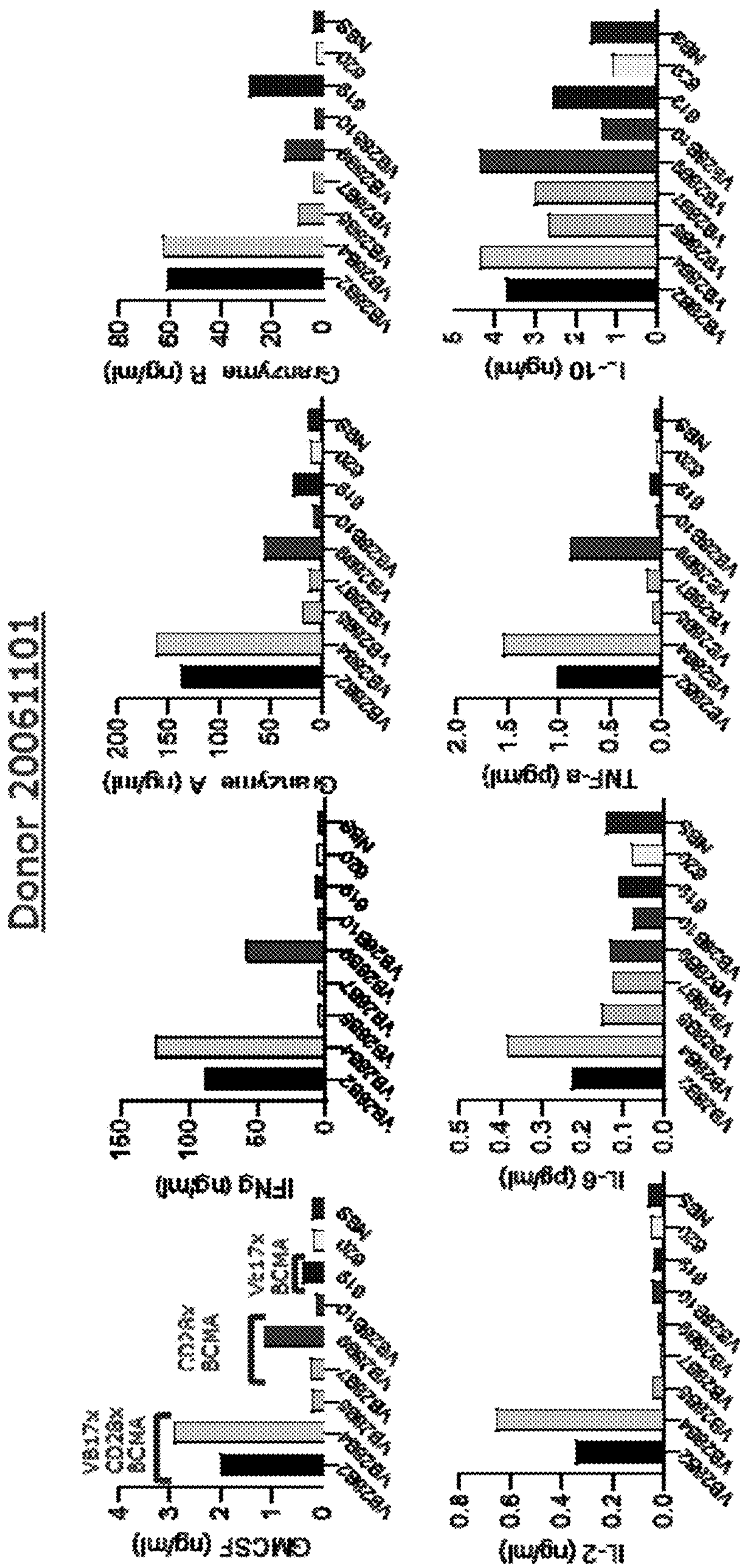

Example 8: Engagement of CD28 Potently Enhances the Cytotoxicity Induced by VB17 T Cells To examine if the increased activation of the Vβ17 T cells in the presence of the Vβ17×CD28×BCMA antibodies also resulted in an increase in the functional activity of the Vβ17 T cells, cytotoxicity assays using H929 cells were set up (See FIGS. 6A, 6B and 6C). Vβ17×BCMA antibodies induced H929 target cell death in a dose dependent manner with an EC50 of ~0.01 μg/ml. This cytotoxicity was very strongly enhanced by the Vβ17×CD28×BCMA antibodies by about 100-fold. VB28B7 antibody (null×CD28×BCMA) did not show any cytotoxicity thus showing the specificity of the increased cytotoxic response. VB28B8 and VB28B9 (null×CD28×BCMA) antibodies which had shown activation of the Vβ17 T cells in the absence of the Vβ17 arm also showed cytotoxicity against H929 cells albeit at lower levels than Vβ17×CD28×BCMA antibodies. To show the specificity of the cytotoxic response induced by the Vβ17×CD28×BCMA antibodies, cytotoxic activity of Vβ17 T cells depleted Pan T cells was examined. Depletion of the Vβ17 T cells resulted in almost complete abrogation of the cytotoxic activity of the Vβ17×CD28×BCMA antibodies. Activity of the Vβ17×BCMA antibody was completely lost with the depletion of the Vβ17 T cells.

Example 9: Engagement of CD28 Potently Enhances the Cytokine Secretion

Consistent with the enhancement of T cell activation and cytotoxicity, Vβ17×CD28×BCMA bispecifics also showed superior cytokine release in comparison to Vβ17×BCMA antibodies and Null×CD28×BCMA antibodies (See FIGS. 7A, 7B, 7C and 7D). VB28B1 antibody as expected did not show an increased cytokine release since this antibody showed poor CD28 binding and no Vβ17 T cell activation or cytotoxicity against H929 target cells. VB28B8 and VB29B9 antibodies also showed potent cytokine release although the levels were lower than the Vβ17×CD28×BCMA antibodies. This was in line with the activation profile of Vβ17 T cells observed with these antibodies.

Example 10: Expression of Costimulatory Ligands on BCMA Expressing H929 Cell Lines To check for expression of costimulatory ligands on multiple myeloma cell lines, multiple myeloma cell lines MM1.R and H929 were stained with anti-human CD28 (purified anti human CD28, cat #555725, BD Pharmingen) for 30 minutes followed by staining with goat anti-mouse IgG (cat #405307, Biolegend). For 41BBL expression, cells were stained with anti-human CD137 antibody (cat #311506) for 30 minutes on ice as per the manufacturer's protocol. All staining was done post Fc block. Following the staining, cells were acquired on the Novocyte flow cytometer. Cells were gated on FSC/SSC, followed by live cell gating and CD28 expression and 41BB expression was plotted as histograms. As shown in FIG. 8, both tested multiple myeloma cell lines, MM1.R and H929 were found to express CD28 while no expression of 4IBBL was observed on either of the cell lines. This is in line with previous reports that have shown CD28 expression on primary myeloma plasma cells.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

What is claimed is:

1. An antibody that binds to CD28 comprising:

(1) (i) a VH comprising the amino acid sequence of SEQ ID NO:31; and (ii) a VL comprising the amino acid sequence of SEQ ID NO:32;

(2) (i) a VH comprising the amino acid sequence of SEQ ID NO:65; and (ii) a VL comprising the amino acid sequence of SEQ ID NO:66;

(3) (i) a VH comprising the amino acid sequence of SEQ ID NO:99; and (ii) a VL comprising the amino acid sequence of SEQ ID NO:100;

(4) (i) a VH comprising the amino acid sequence of SEQ ID NO:133; and (ii) a VL comprising the amino acid sequence of SEQ ID NO: 134.

2. The antibody of claim 1, wherein the antibody is a bispecific antibody or a multispecific antibody.

3. A multispecific antibody, wherein the multispecific antibody comprises: a first binding domain that binds to CD28 and a second binding domain that binds to a second target that is not CD28, wherein the first binding domain that binds to CD28 comprises:

(1) (i) a VH comprising the amino acid sequence of SEQ ID NO:31; and (ii) a VL comprising the amino acid sequence of SEQ ID NO:32;

(2) (i) a VH comprising the amino acid sequence of SEQ ID NO:65; and (ii) a VL comprising the amino acid sequence of SEQ ID NO:66;

(3) (i) a VH comprising the amino acid sequence of SEQ ID NO:99; and (ii) a VL comprising the amino acid sequence of SEQ ID NO:100;

(4) (i) a VH comprising the amino acid sequence of SEQ ID NO:133; and (ii) a VL comprising the amino acid sequence of SEQ ID NO: 134.

4. An antibody that binds to CD28 comprising:

(1) (i) a VH comprising a CDR1, CDR2, and CDR3 of SEQ ID NOs: 1, 2, and 3, respectively; and (ii) a VL comprising a CDR1, CDR2, and CDR3 of SEQ ID NOs: 4, 5, and 6, respectively;

(2) (i) a VH comprising a CDR1, CDR2, and CDR3 of SEQ ID NOs: 35, 36, and 37, respectively; and (ii) a VL comprising a CDR1, CDR2, and CDR3 of SEQ ID NOs: 38, 39, and 40, respectively;

(3) (i) a VH comprising a CDR1, CDR2, and CDR3 of SEQ ID NOs: 69, 70, and 71, respectively; and (ii) a VL comprising a CDR1, CDR2, and CDR3 of SEQ ID NOs: 72, 73, and 74, respectively;

(4) (i) a VH comprising a CDR1, CDR2, and CDR3 of SEQ ID NOs: 103, 104, and 105, respectively; and (ii) a VL comprising a CDR1, CDR2, and CDR3 of SEQ ID NOs: 106, 107, and 108, respectively;

(5) (i) a VH comprising a CDR1, CDR2, and CDR3 of SEQ ID NOs: 7, 8, and 9, respectively; and (ii) a VL comprising a CDR1, CDR2, and CDR3 of SEQ ID NOs: 10, 11, and 12, respectively;

(6) (i) a VH comprising a CDR1, CDR2, and CDR3 of SEQ ID NOs: 41, 42, and 43, respectively; and (ii) a VL comprising a CDR1, CDR2, and CDR3 of SEQ ID NOs: 44, 45, and 46, respectively;

(7) (i) a VH comprising a CDR1, CDR2, and CDR3 of SEQ ID NOs: 75, 76, and 77, respectively; and (ii) a VL comprising a CDR1, CDR2, and CDR3 of SEQ ID NOs: 78, 79, and 80, respectively;

(8) (i) a VH comprising a CDR1, CDR2, and CDR3 of SEQ ID NOs: 109, 110, and 111, respectively; and (ii) a VL comprising a CDR1, CDR2, and CDR3 of SEQ ID NOs: 112, 113, and 114, respectively;

(9) (i) a VH comprising a CDR1, CDR2, and CDR3 of SEQ ID NOs: 13, 14, and 15, respectively; and (ii) a VL comprising a CDR1, CDR2, and CDR3 of SEQ ID NOs: 16, 17, and 18, respectively;

(10) (i) a VH comprising a CDR1, CDR2, and CDR3 of SEQ ID NOs: 47, 48, and 49, respectively; and (ii) a VL comprising a CDR1, CDR2, and CDR3 of SEQ ID NOs: 50, 51, and 52, respectively;

(11) (i) a VH comprising a CDR1, CDR2, and CDR3 of SEQ ID NOs: 81, 82, and 83, respectively; and (ii) a VL comprising a CDR1, CDR2, and CDR3 of SEQ ID NOs: 84, 85, and 86, respectively;

(12) (i) a VH comprising a CDR1, CDR2, and CDR3 of SEQ ID NOs: 115, 116, and 117, respectively; and (ii) a VL comprising a CDR1, CDR2, and CDR3 of SEQ ID NOs: 118, 119, and 120, respectively;

(13) (i) a VH comprising a CDR1, CDR2, and CDR3 of SEQ ID NOs: 19, 20, and 21, respectively; and (ii) a VL comprising a CDR1, CDR2, and CDR3 of SEQ ID NOs: 22, 23, and 24, respectively;

(14) (i) a VH comprising a CDR1, CDR2, and CDR3 of SEQ ID NOs: 53, 54, and 55, respectively; and (ii) a VL comprising a CDR1, CDR2, and CDR3 of SEQ ID NOs: 56, 57, and 58, respectively;

(15) (i) a VH comprising a CDR1, CDR2, and CDR3 of SEQ ID NOs: 87, 88, and 89, respectively; and (ii) a VL comprising a CDR1, CDR2, and CDR3 of SEQ ID NOs: 90, 91, and 92, respectively;

(16) (i) a VH comprising a CDR1, CDR2, and CDR3 of SEQ ID NOs: 121, 122, and 123, respectively; and (ii) a VL comprising a CDR1, CDR2, and CDR3 of SEQ ID NOs: 124, 125, and 126, respectively;

(17) (i) a VH comprising a CDR1, CDR2, and CDR3 of SEQ ID NOs: 25, 26, and 27, respectively; and (ii) a VL comprising a CDR1, CDR2, and CDR3 of SEQ ID NOs: 28, 29, and 30, respectively;

(18) (i) a VH comprising a CDR1, CDR2, and CDR3 of SEQ ID NOs: 59, 60, and 61, respectively; and (ii) a VL comprising a CDR1, CDR2, and CDR3 of SEQ ID NOs: 62, 63, and 64, respectively;

(19) (i) a VH comprising a CDR1, CDR2, and CDR3 of SEQ ID NOs: 93, 94, and 95, respectively; and (ii) a VL comprising a CDR1, CDR2, and CDR3 of SEQ ID NOs: 96, 97, and 98, respectively; and

(20) (i) a VH comprising a CDR1, CDR2, and CDR3 of SEQ ID NOs: 127, 128, and 129, respectively; and (ii) a VL comprising a CDR1, CDR2, and CDR3 of SEQ ID NOs: 130, 131, and 132, respectively.

5. The antibody of claim 4, wherein the antibody is a bispecific antibody or a multispecific antibody.

* * * * *